(12) United States Patent
Ghosh et al.

(10) Patent No.: US 9,670,225 B2
(45) Date of Patent: Jun. 6, 2017

(54) HIV-1 PROTEASE INHIBITORS AND USES THEREOF

(71) Applicants: Purdue Research Foundation, West Lafayette, IN (US); Hiroaki Mitsuya, Kumamoto (JP)

(72) Inventors: Arun K. Ghosh, West Lafayette, IN (US); Venkateswara Rao Kalapala, Pradesh (IN); Hiroaki Mitsuya, Kumamoto (JP)

(73) Assignees: Purdue Research Foundation, West Lafayette, IN (US); National University Corporation Kumamoto University, Kumamoto (JP)

( * ) Notice: Subject to any disclaimer, the term of this patent is extended or adjusted under 35 U.S.C. 154(b) by 0 days.

(21) Appl. No.: 15/311,806

(22) PCT Filed: May 15, 2015

(86) PCT No.: PCT/US2015/031181
§ 371 (c)(1),
(2) Date: Nov. 16, 2016

(87) PCT Pub. No.: WO2015/175994
PCT Pub. Date: Nov. 19, 2015

(65) Prior Publication Data
US 2017/0088555 A1      Mar. 30, 2017

Related U.S. Application Data

(60) Provisional application No. 61/994,462, filed on May 16, 2014.

(51) Int. Cl.
*C07D 493/08* (2006.01)

(52) U.S. Cl.
CPC .................... *C07D 493/08* (2013.01)

(58) Field of Classification Search
None
See application file for complete search history.

(56) References Cited

U.S. PATENT DOCUMENTS

| 8,501,961 B2 * | 8/2013 | Ghosh | C07D 273/01 548/453 |
| 2009/0312318 A1 * | 12/2009 | Desai | C07D 493/04 514/233.8 |
| 2013/0158094 A1 * | 6/2013 | Ghosh | C07D 493/04 514/437 |

FOREIGN PATENT DOCUMENTS

WO    WO-2015175994 A1    11/2015

OTHER PUBLICATIONS

"International Application Serial No. PCT/US2015/031181, International Search Report mailed Aug. 11, 2015", 2 pgs.
"International Application Serial No. PCT/US2015/031181, Written Opinion mailed Aug. 11, 2015", 3 pgs.
Nakamura, et al., "Inhibitory Effects of Polyethers on Human Immunodeficiency Virus Replication", Antimicrob. Agents Chemother, (1992), 492-494.
Wlodawer, A, et al., "Inhibitors of HIV-1 protease: a major success of structure-assisted drug design", Annual Review of Biophysics & Biomolecular Structure, 27, (1998), 249-284.

* cited by examiner

Primary Examiner — Karl J Puttlitz
(74) Attorney, Agent, or Firm — Schwegman Lundberg & Woessner, P.A.

(57) ABSTRACT

Various embodiments of the present invention are directed to compounds of the formula (I) or a pharmaceutically acceptable salt, polymorph, prodrug, solvate or clathrate thereof, wherein $X^1$, $X^2$, $X^3$, $R^1$, $R^2$, $R^{11}$, and n are defined herein. These compounds are useful as inhibitors of HIV-1 protease and, as a result, are useful in the treatment of HIV infection.

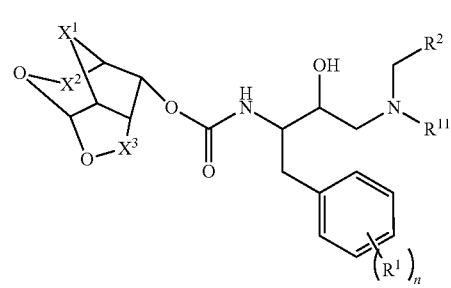

(I)

20 Claims, No Drawings

HIV-1 PROTEASE INHIBITORS AND USES THEREOF

CROSS-REFERENCE TO RELATED APPLICATIONS

This application is a U.S. National Stage Filing under 35 U.S.C. §371 from International Application No. PCT/US2015/031181, filed on May 15, 2015, and published as WO 2015/175994 on Nov. 19, 2015, which claims the benefit of priority to U.S. Provisional Appl. Ser. No. 61/994,462, filed May 16, 2014, which applications are incorporated by reference as if fully set forth herein.

STATEMENT OF GOVERNMENT SUPPORT

This invention was made with government support under grant GM053386 awarded by the National Institutes of Health. The government has certain rights in the invention.

BACKGROUND OF THE INVENTION

The AIDS epidemic is one of the most challenging problems in medicine in the 21st century. Among many strategies to combat this disease, highly active antiretroviral therapy (HAART) with HIV protease inhibitors (PIs) in combination with reverse transcriptase inhibitors (RTIs) continues to be the first line treatment for control of HIV infection. Although such combination therapy has improved quality of life, enhanced HIV management, and halted the progression of the disease, there remain many challenges to treating this devastating disease, including decreasing both the toxicity and complexity of these treatment regimens. In addition, there is a growing population of patients that is developing multi-drug resistant strains of HIV. And there is ample evidence that these strains can be further transmitted.

Even though HAART has had a major impact on the AIDS epidemic in industrially advanced nations, it has not achieved the eradication of human immunodeficiency virus type 1 (HIV 1), in part due to the viral reservoirs remaining in blood and infected tissues. The limitation of antiviral therapy of AIDS is also exacerbated by complicated regimens, the development of drug-resistant HIV-1 variants, and a number of inherent adverse effects. Further, efforts to bring about the optimal benefits of HAART have met with a number of challenges, including (i) drug-related toxicities; (ii) partial restoration of immunologic functions once individuals developed AIDS; (iii) development of various cancers as a consequence of survival prolongation; (iv) flame-up of inflammation in individuals receiving HAART or immune re-construction syndrome (IRS); and (v) increased cost of antiviral therapy. Such limitations of HAART are exacerbated by the development of drug-resistant HIV-1 variant.

There is presently a paucity of antiretroviral drugs or agents that are not only substantially specific for HIV-1, but also devoid of toxicity or side effects in the therapy of AIDS.

SUMMARY OF THE INVENTION

Embodiments of the present invention are directed to potent HIV-1 protease inhibitors or aspartyl protease inhibitors for the treatment of AIDS and HIV infections. HIV-1 protease inhibitors can be critical components of antiretroviral treatment of HIV/AIDS. HIV-1 protease inhibitors can also be components of antiretroviral treatment of HIV/AIDS in a monotherapy regimen, wherein the HIV-1 protease inhibitors or aspartyl protease inhibitors of the various embodiments of the present invention are administered alone; that is, in the absences of, e.g., RTIs.

The HIV-1 protease inhibitors or aspartyl protease inhibitors of the various embodiments of the present invention represent a conceptually new class of HIV-1 protease inhibitors containing unprecedented substitution patterns that result in compounds that are surprisingly and unexpectedly nearly 100-fold more potent than, e.g., darunavir in cell culture assay. In some embodiments, the HIV-1 protease inhibitors or aspartyl protease inhibitors of the various embodiments of the present invention can have significant antiviral activity against darunavir-resistant HIV-1 variants.

DETAILED DESCRIPTION OF THE INVENTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "organic group" as used herein refers to but is not limited to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, (CH$_2$)$_{0-2}$P(O)OR$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)C(O)OR, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen (in examples that include other carbon atoms) or a carbon-based moiety (e.g., alkyl, cycloalkyl, heterocycloalkyl, aryl, and heteroaryl), and wherein the carbon-based moiety can itself be further substituted.

The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents, J, that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, (CH$_2$)$_{0-2}$P(O)OR$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)C(O)OR, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted with J; or wherein two R groups bonded to a nitrogen atom or to adjacent nitrogen atoms can together with the nitrogen atom or atoms form a heterocyclyl, which can be mono- or independently multi-substituted with J.

The term "alkyl" as used herein refers to substituted or unsubstituted straight chain and branched alkyl groups and cycloalkyl groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH=CH—, —CH=CHCH$_2$—, and the like. Examples of branched alkenyl groups include, but are not limited to, —CH=C(CH$_3$)— and the like.

The term "alkylene" as used herein refers to substituted or unsubstituted straight chain and branched divalent alkylene groups and cycloalkylene groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$) or, in some embodiments, from 1 to 4 carbon atoms ($C_1$-$C_4$), from 1 to 5 carbon atoms ($C_1$-$C_5$), from 2 to 5 carbon atoms ($C_2$-$C_5$) or from 3 to 4 carbon atoms ($C_3$-$C_4$). Examples of straight chain alkylene groups include those with from 1 to 8 carbon atoms such as methylene (—CH$_2$—), ethylene (—CH$_2$CH$_2$—), n-propylene (—CH$_2$CH$_2$CH$_2$—), n-butylene (—CH$_2$(CH$_2$)$_2$CH$_2$—) and the like. Examples of branched alkylene groups include, but are not limited to, isopropylidene (CH$_2$CH(CH$_3$)) and the like. Examples of cycloalkylene groups include, but are not limited to, cyclopropylidene, cyclobutylidene, cyclopentylidene and the like.

The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_8$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "cycloalkylalkyl" as used herein refers to substituted or unsubstituted alkyl groups as defined herein in which a hydrogen or carbon bond of an alkyl group as defined herein is replaced with a bond to a cycloalkyl group as defined herein. Representative cycloalkylalkyl groups include, but are not limited to, cyclopentylalkyl.

The term "alkylcycloalkyl" as used herein refers to substituted or unsubstituted cycloalkyl groups as defined herein in which a hydrogen of a cycloalkyl group as defined herein is replaced with a bond to an alkyl group as defined herein. Representative alkylcycloalkyl groups include, but are not limited to, alkylcyclopropyl.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "heterocyclylcarbonyl" is an example of an acyl group that is bonded to a substituted or unsubstituted heterocyclyl group, as the term "heterocyclyl" is defined herein. An example of a heterocyclylcarbonyl group is a prolyl group, wherein the prolyl group can be a D- or an L-prolyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups. Examples of indolinonyl groups include groups having the general formula:

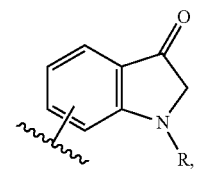

wherein R is as defined herein.

Examples of isoindolinonyl groups include groups having the general formula:

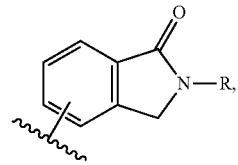

wherein R is as defined herein.

Examples of benzoxazolinyl groups include groups having the general formula:

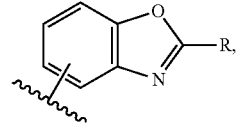

wherein R is as defined herein.

Examples of benzthiazolinyl groups include groups having the general formula:

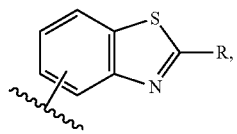

wherein R is as defined herein.

In some embodiments, the group R in benzoxazolinyl and benzthiazolinyl groups is an N(R)$_2$ group. In some embodiments, each R is hydrogen or alkyl, wherein the alkyl group is substituted or unsubstituted. In some embodiments, the alkyl group is substituted with a heterocyclyl group (e.g., with a pyrrolidinyl group).

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heterocyclylalkyloxy" as used herein refers to alkyl groups as defined herein in which a hydrogen or carbon bond of an alkyl group as defined herein is replaced with a bond to a heterocyclyl group as defined herein and the alkyl group is attached to an oxygen. Representative heterocyclylalkyloxy groups include, but are not limited to, —O—(CH$_2$)$_q$heterocyclyl, wherein q is an integer from 1 to 5. In some embodiments, heterocyclylalkyloxy groups include —O—(CH$_2$)$_q$morpholinyl such as —O—CH$_2$CH$_2$-morpholine.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR 3$^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —CF(CH$_3$)$_2$ and the like.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Various embodiments of the present invention are directed to a compound of the formula (I):

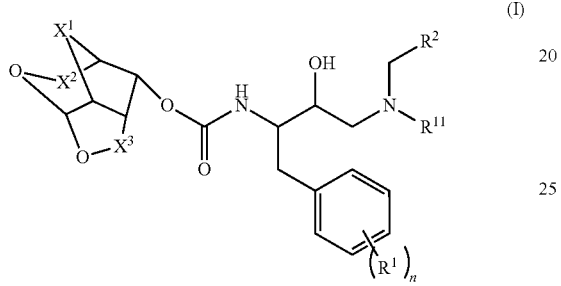

(I)

or a pharmaceutically acceptable salt, polymorph, prodrug, solvate or clathrate thereof, wherein: $X^1$ is alkylene, —O—, —CH$_2$NR$^4$— or —NHR$^4$—; $X^2$ and $X^3$ are each, independently alkylene; n is an integer from 0 to 3; $R^1$ is alkoxy, hydroxyalkyl, halo or heterocyclylalkyloxy; $R^2$ is alkyl, haloalkyl, aryl, arylalkyl, cycloalkylalkyl, heterocyclylcarbonyl, heterocyclyl, heterocyclylalkyl or —C(R$^7$R$^8$)-alkylene-R$^9$; $R^{11}$ is —SO$_2$R$^3$, —N(R$^{12}$)SO$_2$R$^3$, —N(R$^{12}$)C(O)R$^3$, —N(R$^{12}$)C(O)CH(R$^{12}$)N(R$^{12}$)C(O)R$^{13}$, —C(O)N(R$^{12}$)$_2$, —C(O)-alkylene-X$^4$—R$^{10}$ (wherein $X^4$ is S, O or NR$^6$, wherein $R^6$ is H, alklyl, cycloalkyl or alkylaryl) or —C(O)R$^{10}$; $R^3$ is aryl or heteroaryl; $R^4$ is alkyl, aryl or heteroaryl; $R^7$ and $R^8$ are each, independently hydrogen, alkyl, aryl, arylalky, heteroaryl, heteroarylalkyl or, $R^7$ and $R^8$, together with the carbon atom to which they are attached, form a cycloalkyl or a heterocyclyl group; $R^9$ is hydrogen, OR$^{10}$, OC(O)N(R$^{10}$)$_2$, CN, NO$_2$, CF$_3$, OCF$_3$, N(R$^{10}$)$_2$, SR$^{10}$, SO$_2$R$^{10}$, SO$_2$N(R$^{10}$)$_2$, SO$_3$R, C(O)R$^{10}$, C(O)OR$^{10}$, OC(O)R$^{10}$, C(O)N(R$^{10}$)$_2$, (CH$_2$)$_{0\text{-}2}$N(R$^{10}$)C(O)R$^{10}$ or (CH$_2$)$_{0\text{-}2}$N(R$^{10}$)C(O)OR$^{10}$; $R^{10}$ is hydrogen, alkyl, acyl, cycloalkyl, aryl, aralkyl, heterocyclyl, heteroaryl, or heteroarylalkyl; $R^{12}$ is hydrogen, alkyl, alkylaryl, heterocyclyl or the two $R^{12}$ groups on an N(R$^{12}$)$_2$, together with the nitrogen atom to which they are attached, form a heterocyclyl group; and $R^{13}$ is hydrogen, alkyl, —N(R$^{12}$)$_2$ or —OR$^{12}$. In some embodiments, $R^2$ and $R^{11}$, together with the —CH$_2$N— that connects them, form a heterocyclyl or substituted heterocyclyl group.

All diastereomers of the compounds of the formula (I) are contemplated herein. In various other embodiments of the present invention are directed to a compound of the formula (Ia)-(Ih):

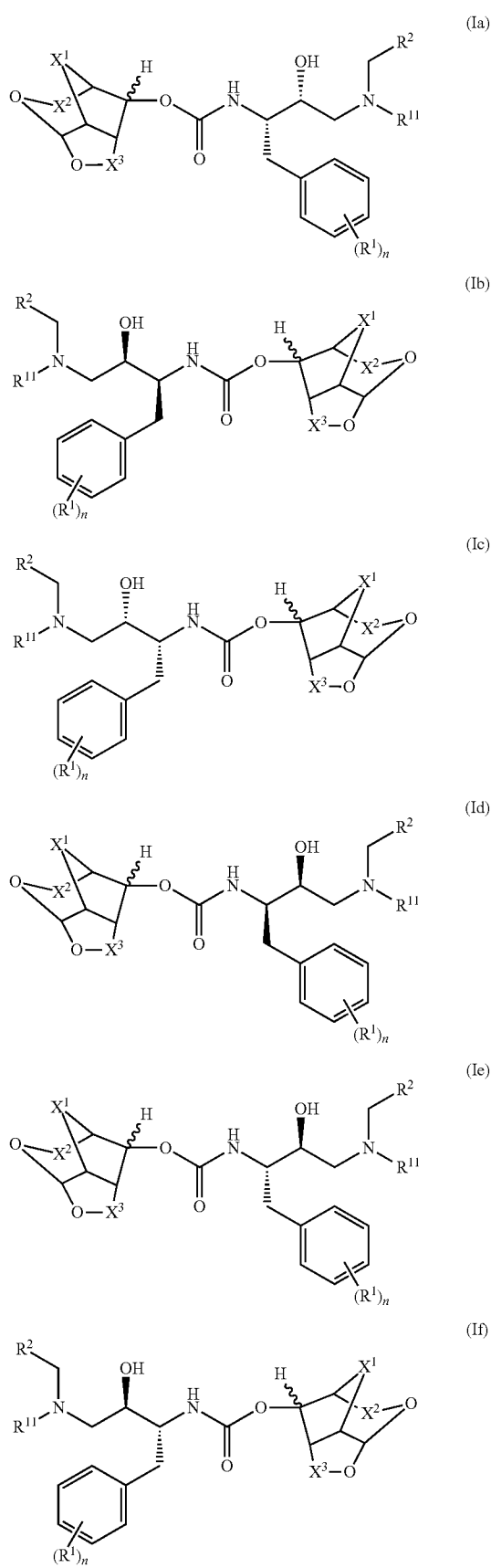

-continued

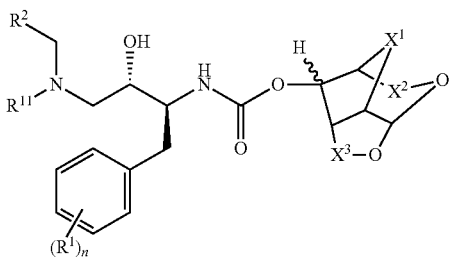

(Ig)

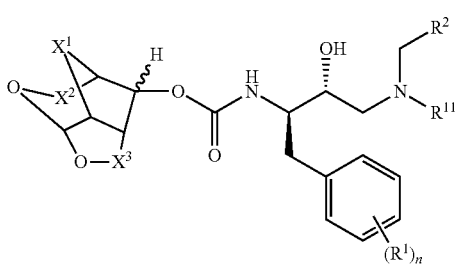

(Ih)

or a pharmaceutically acceptable salt, polymorph, prodrug, solvate or clathrate thereof, wherein $X^1$, $X^2$, $X^3$, $R^1$, $R^2$, $R^{11}$, and n are defined herein. In some embodiments, $X^1$ in the compounds of the formula (I) and (Ia)-(Ih) is alkylene, for example, $C_1$-$C_4$ alkylene, including —$CH_2$— and —$CH_2CH_2$—. In some embodiments, $X^2$ in the compounds of the formula (I) and (Ia)-(Ih) is alkylene, for example, $C_1$-$C_4$ alkylene, including —$CH_2$— and —$CH_2CH_2$—. In some embodiments, $X^3$ in the compounds of the formula (I) and (Ia)-(Ih) is alkylene, for example, $C_1$-$C_4$ alkylene, including —$CH_2$— and —$CH_2CH_2$—. In some embodiments, $X^1$, $X^2$, and $X^3$ in the compounds of the formula (I) and (Ia)-(Ih) is —$CH_2$—. In other embodiments, $X^1$ is —$CH_2$—; $X^2$ is —$CH_2$—; and $X^3$ is —$CH_2CH_2$—. In still other embodiments, $X^1$ is —$CH_2$—; $X^2$ is —$CH_2CH_2$—; and $X^3$ is —$CH_2$—. In still other embodiments, $X^1$ is —$CH_2CH_2$—; $X^2$ is —$CH_2$—; and $X^3$ is —$CH_2$—.

In some embodiments, n is 0 such that the phenyl ring to which $R^1$ is attached is unsubstituted.

In some embodiments, $R^2$ is alkyl (e.g., $C_1$-$C_6$ alkyl). In other embodiments, $R^2$ is a heterocyclyl group that can be substituted. In some embodiments, the heterocyclyl group is pyrrolidinyl or azetidinyl group. When, substituted, the heterocyclyl group can be substituted with alkyl (e.g., $C_1$-$C_6$ alkyl). In still other embodiments, $R^2$ is a —$C(R^7R^8)$-alkylene-$R^9$ group, wherein the alkylene is a $C_1$-$C_5$ alkylene, such as a $C_2$-$C_5$ alkylene or a $C_3$-$C_4$ alkylene. In some embodiments, $R^9$ is —$OC(O)N(R^{10})_2$ or —$(CH_2)_{0-2}N(R^{10})C(O)OR^{10}$, wherein $R^{10}$ is defined herein.

In some embodiments, $R^2$ is aryl that can be substituted. When substituted, the aryl group can be substituted with a heterocyclyl group, such as a heteroaryl group. In some embodiments, the heteroaryl group is a pyridinyl group.

In some embodiments, $R^{11}$ is —$SO_2R^3$, wherein $R^3$ is aryl. In some embodiments, the aryl is substituted. In some embodiments, the aryl of $R^3$ is substituted with an alkenyl group, a cycloalkyl group or a heterocyclyl group, each of which, in turn can be substituted. In some embodiments, the heterocyclyl group is a heteroaryl group. Examples of heterocyclyl groups that can be substituents on the aryl of $R^3$ include one or more groups selected from the group consisting of 4,5-dihydrooxazolyl, oxaxolyl, oxadiazolyl, indolyl, and isoindolyl. When substituted, the heterocyclyl group can be substituted with one or more groups selected from the group consisting of alkyl (e.g., $C_1$-$C_6$ alkyl), —C(O)R, —$CF_3$, -alkylene-$NR_2$, —$NR_2$, and —OR, wherein R is defined herein. Examples of cycloalkyl groups that can be substituents on the aryl of $R^3$ include cyclopropyl, cyclobutyl, and cyclopentyl groups. When substituted, the cycloalkyl group can be substituted with one or more groups selected from the group consisting of —CN, —OR, -alkylene-$NR_2$, —$NR_2$ or —$C(O)N(R)_2$, wherein R is defined herein. When substituted, the alkenyl group (e.g., $C_1$-$C_6$ alkenyl) can be substituted with alkyl, -alkyl-$NR_2$ or —$C(O)N(R)_2$.

In some embodiments, $R^{11}$ is —$N(R^{12})C(O)CH(R^{12})N(R^{12})C(O)R^{13}$, wherein $R^{12}$ and $R^{13}$ are defined herein. In some embodiments each $R^{12}$ is hydrogen. In other embodiments, $R^{13}$ is $OR^{12}$, wherein $R^{12}$ is alkyl (e.g., $C_1$-$C_6$ alkyl) or heterocyclyl, such as tetrahydrofuranyl.

In other embodiments, $R^{11}$ is —$N(R^{12})SO_2R^3$ or —$N(R^{12})C(O)R^3$, wherein $R^3$ and $R^{12}$ are defined herein. In some embodiments, $R^{12}$ is hydrogen or alkyl. In some embodiments, $R^3$ is an aryl group or a heteroaryl group. In some embodiments, the heteroaryl group is a benzoxazolyl or benzthiazolyl, each of which can be substituted.

In some embodiments, $R^{11}$ is —$C(O)N(R^{12})_2$, wherein each $R^{12}$ is, independently, hydrogen, alkyl (e.g., $C_1$-$C_6$ alkyl), aryl, heterocyclyl or the two $R^{12}$ groups, together with the nitrogen atom to which they are attached, form a heterocyclyl group. In some embodiments, the two $R^{12}$ groups, together with the nitrogen atom to which they are attached, form a heterocyclyl group, such as a piperidinyl group, which can be substituted.

In some embodiments, Fe is $C_1$-$C_6$ alkoxy, hydroxy-$C_1$-$C_6$-alkyl, halo or $C_1$-$C_6$-heterocyclyl-$C_1$-$C_6$-alkyloxy. Non-limiting examples of $R^1$ groups include —$OCH_3$ (e.g., at the 3- or 4-position of the aromatic ring), —$CH_2OH$ (e.g., at the 3- or 4-position of the aromatic ring), fluoro (e.g., at the 3- or 4-position of the aromatic ring or at the 3 and 5 position of the aromatic ring, such that the ring is 3,5-difluorosubstituted), —O—$CH_2CH_2$morpholine (e.g., at the 3- or 4-position of the aromatic ring).

In some embodiments $R^2$ is $C_1$-$C_6$ alkyl, halo-$C_1$-$C_6$-alkyl, $C_6$-$C_{10}$-aryl-$C_1$-$C_6$-alkyl, $C_3$-$C_6$-cycloalkyl-$C_1$-$C_6$-alkyl, $C_3$-$C_6$-heterocyclylcarbonyl or $C_3$-$C_6$-heterocyclyl-$C_1$-$C_6$-alkyl. Non-limiting examples of $R^2$ groups include —$CH(CH_3)_2$, —$CF(CH_3)_2$, —$CH_2$cyclopentyl, C(Me)cyclopropyl, C(Me)cyclobutyl, C(Me)cyclopentyl, C(Me)tetrahydrofuranyl, —$CH_2$prolyl, and —$CH_2$tetrahydrofuranyl (e.g., —$CH_2$tetrahydrofuran-2-yl).

In some embodiments, $R^3$ is substituted $C_6$-$C_{10}$ aryl. In some embodiments, $R^3$ is substituted phenyl, substituted, in some instances, with at least one of amino (e.g., —$NH_2$), $C_1$-$C_6$ alkoxy (e.g., —$OCH_3$), hydroxy-$C_1$-$C_6$-alkyl (e.g., —$CH_2OH$) and halo (e.g., fluoro).

In some embodiments, $R^3$ is a substituted phenyl group having the formula:

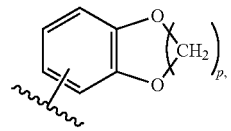

wherein p is an integer from 1 to 2.

In some embodiments, the substituted aryl groups represented by $R^3$ herein can be selected from the group consisting of:

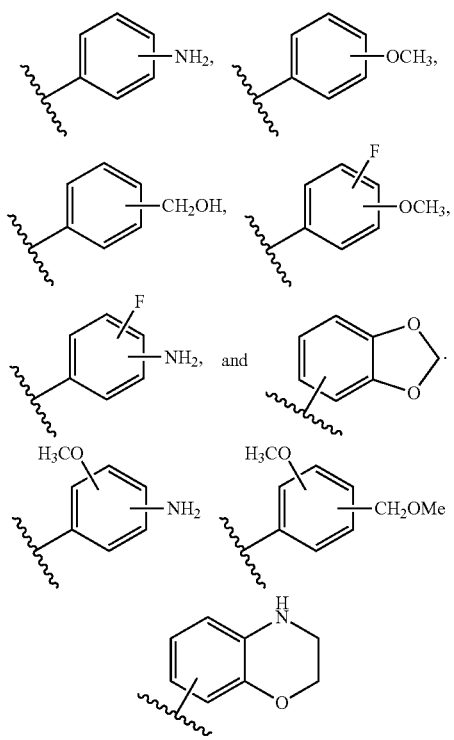

In other embodiments, the substituted aryl groups represented by $R^3$ herein can be selected from the group consisting of:

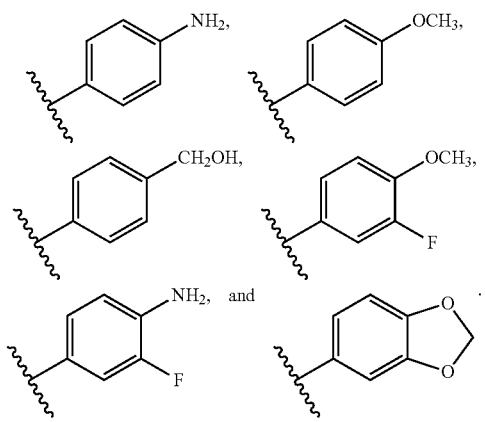

In some embodiments, $R^3$ is substituted $C_6$-$C_8$ heteroaryl. In some embodiments, $R^3$ is a substituted $C_6$-$C_8$ heteroaryl having the formula:

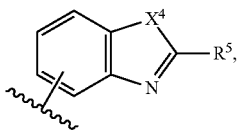

wherein $R^5$ is $C_1$-$C_6$ alkylamino or $C_3$-$C_6$ cycloalkyl-$C_3$-$C_6$ heterocycloamino; and $X^4$ is S, O or $NR^6$, wherein $R^6$ is H, alklyl, cycloalkyl or alkylaryl. Non-limiting examples of $R^5$ include —NHCH$_3$, —NHCH(CH$_3$)$_2$, —NHcyclopropyl, —NHCH$_2$CH(CH$_3$)$_2$, —NHC(CH$_3$)$_3$, and

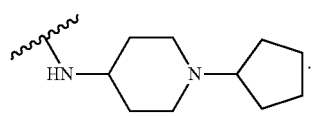 [SMILES: *NC1CCN(C2CCCC2)CC1]

In some embodiments, $R^3$ is substituted $C_6$-$C_8$ heteroaryl. In some embodiments, the substituents on the $C_6$-$C_8$ heteroaryl can be alkyl (e.g., $C_1$-$C_6$ alkyl, such as methyl), —OR, wherein R is defined herein (e.g., $C_1$-$C_6$ alkyl-O—, such as CH$_3$—O—, and $C_6$-$C_{10}$ aryl, such as phenyl-O—), or halo (e.g., Cl or F). In some embodiments, $R^3$ is a substituted $C_6$-$C_8$ heteroaryl having the formula:

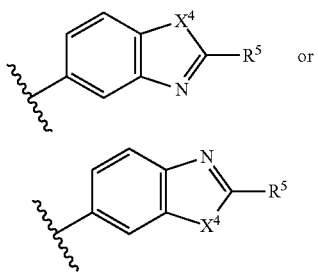

wherein $R^5$ is $C_1$-$C_6$ alkylamino or $C_3$-$C_6$ cycloalkyl-$C_3$-$C_6$ heterocycloamino; and $X^4$ is S, O or $NR^6$, wherein $R^6$ is H, alklyl, cycloalkyl or alkylaryl.

Examples of the compounds of the formula (I) and (Ia)-(Ih) include, but are not limited to:

A

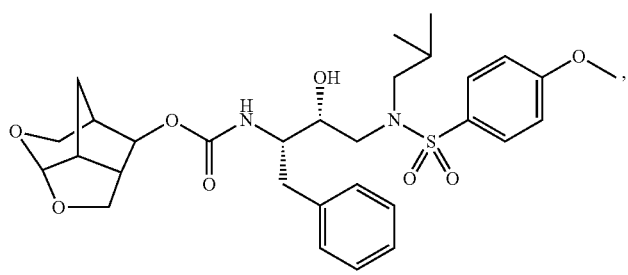

-continued
B
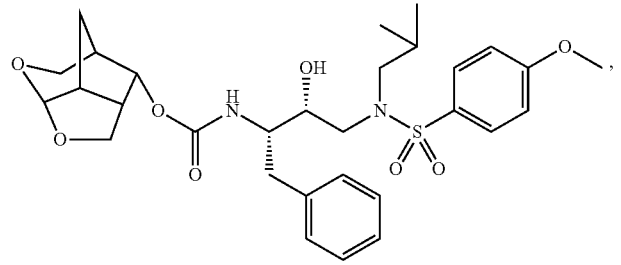
C
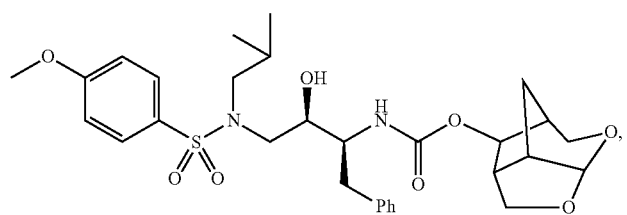
D
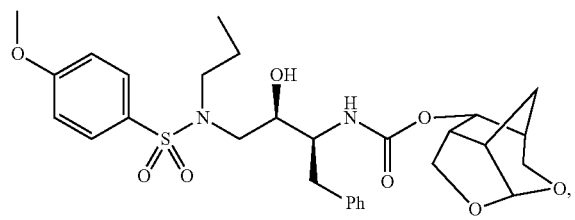
E
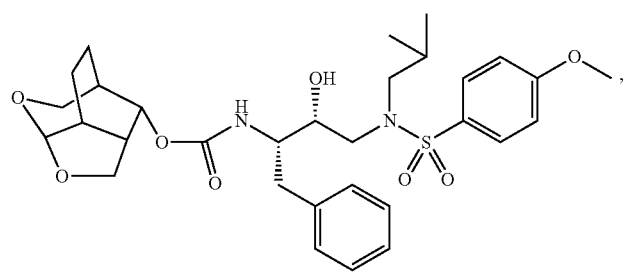
F
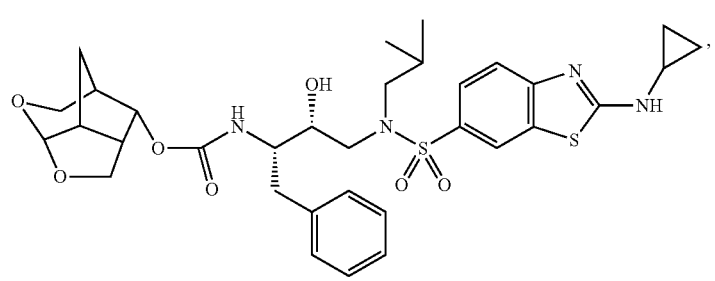
G
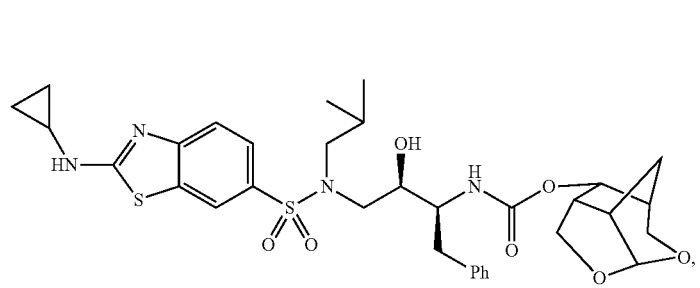

H
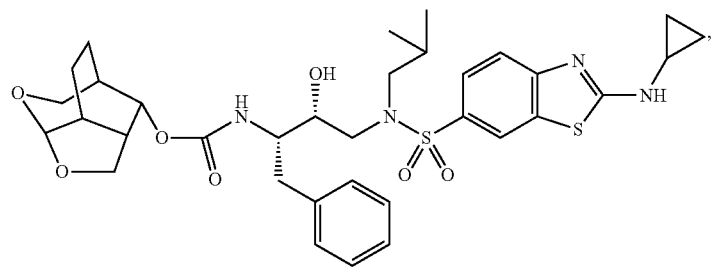
I
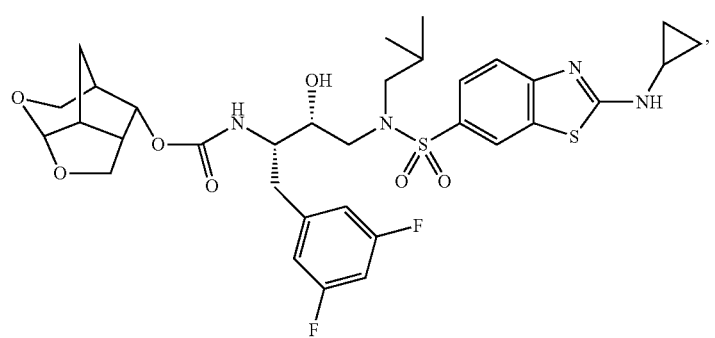
J
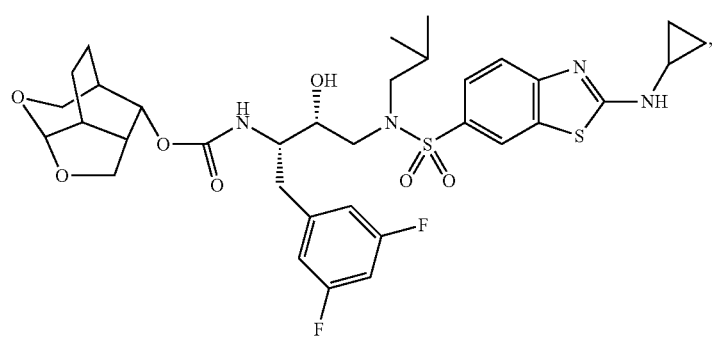
K
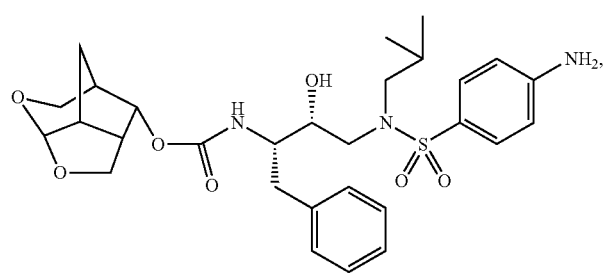
L
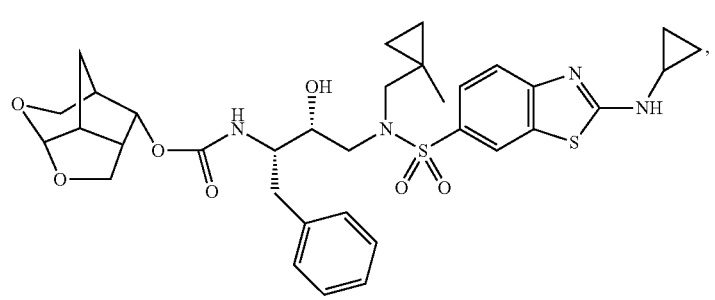

-continued
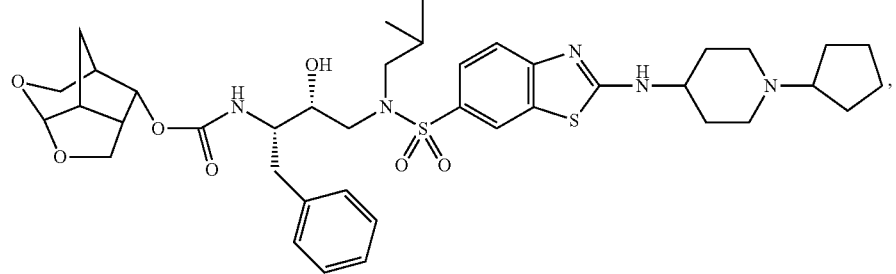
M
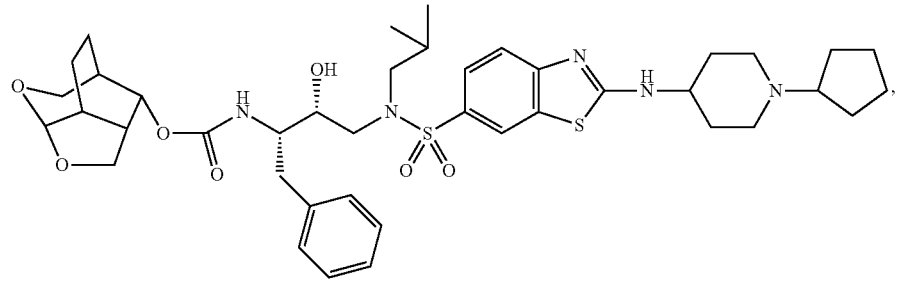
N
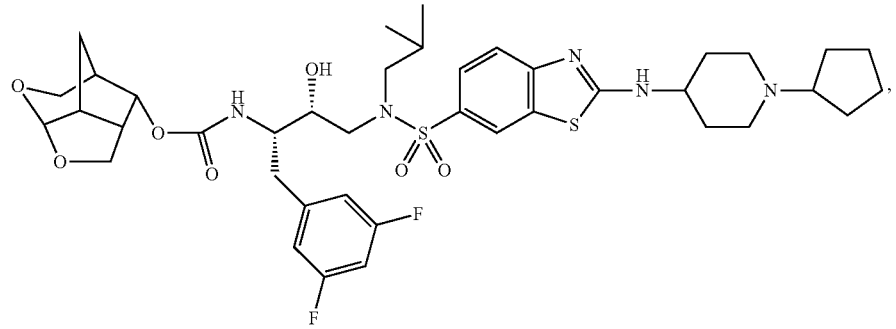
O
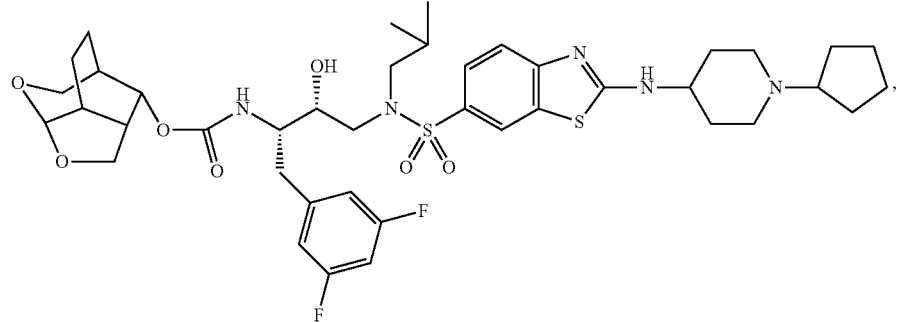
P
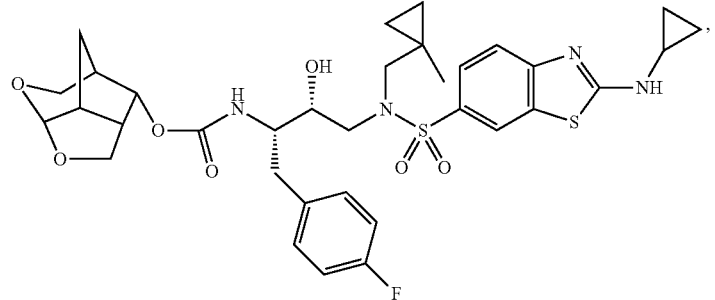
Q

-continued
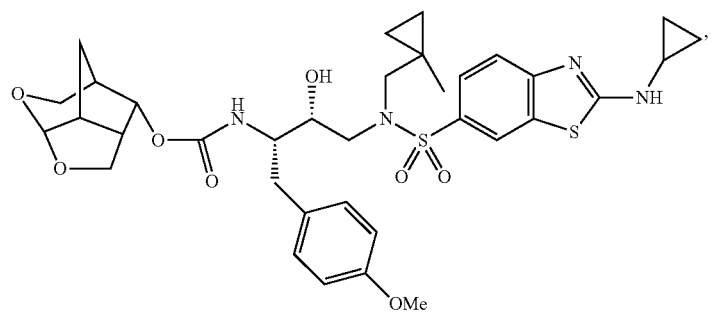
R
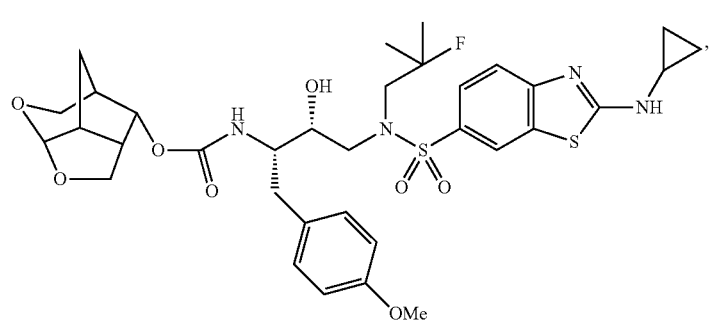
S
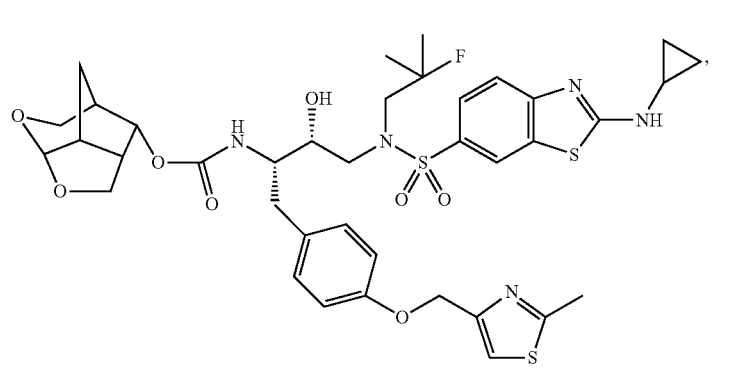
T
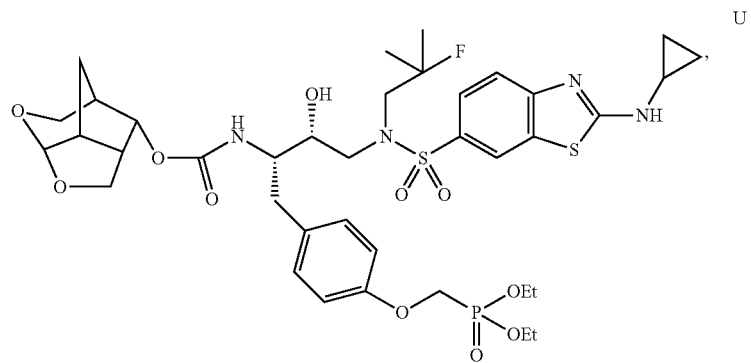
U

-continued
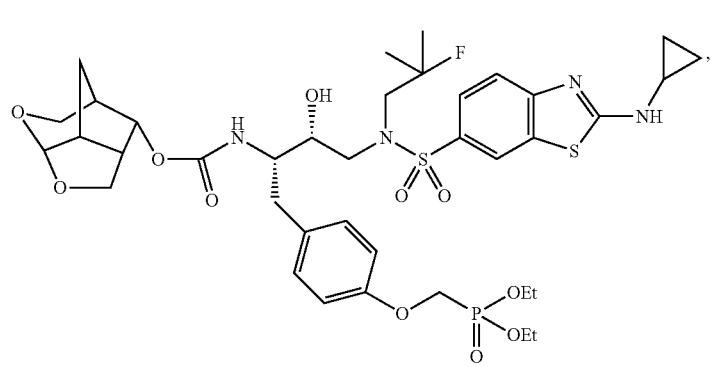
V
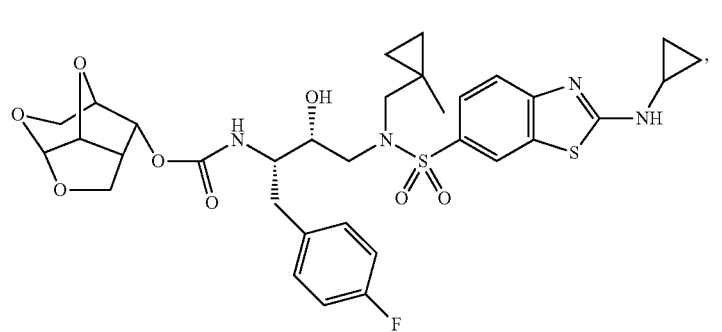
W
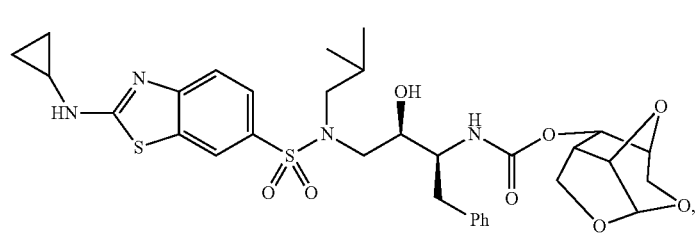
X
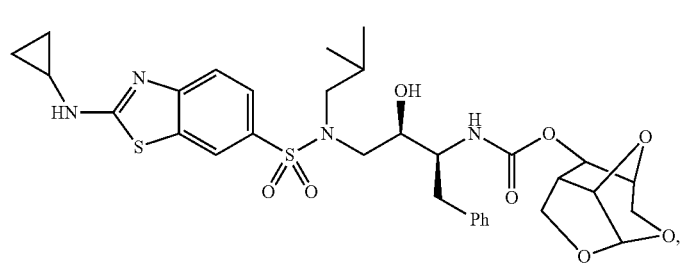
Y
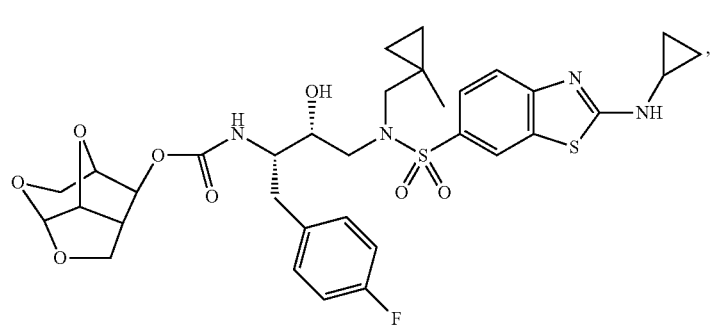
Z

-continued
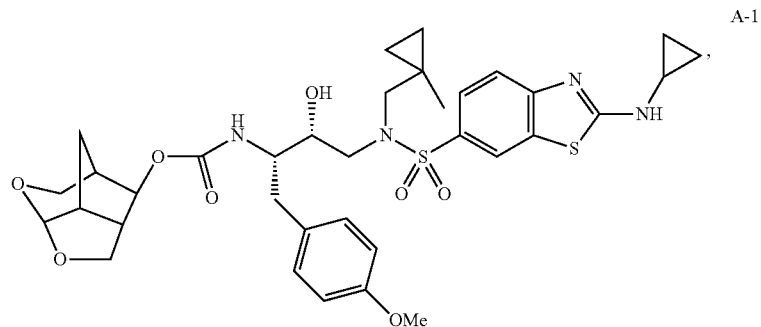
A-1
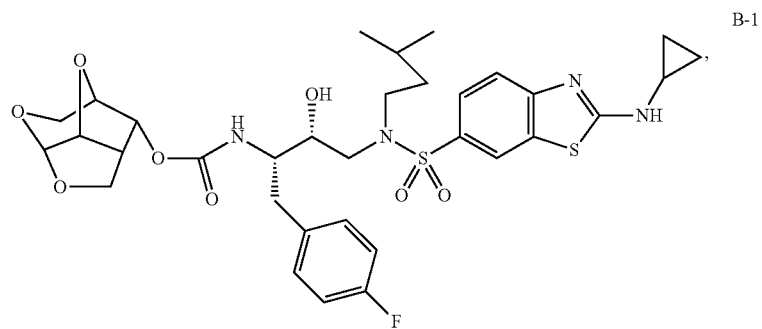
B-1
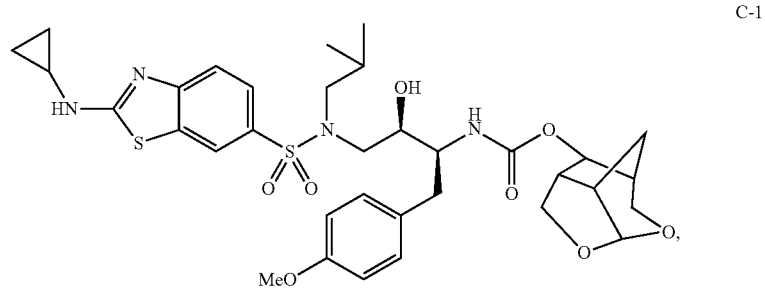
C-1
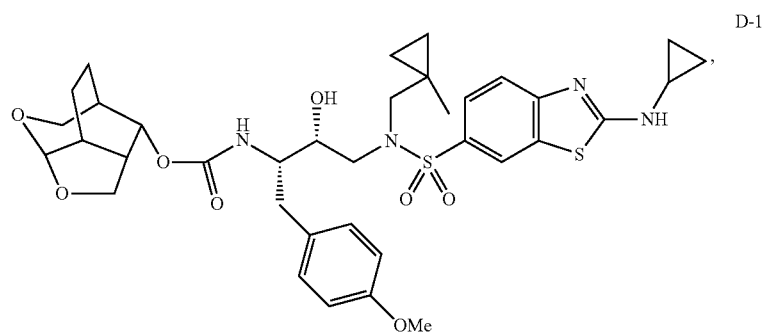
D-1
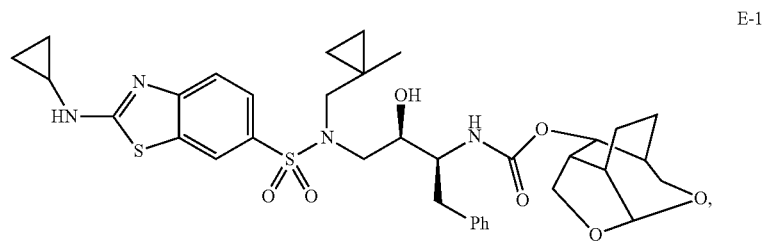
E-1

F-1
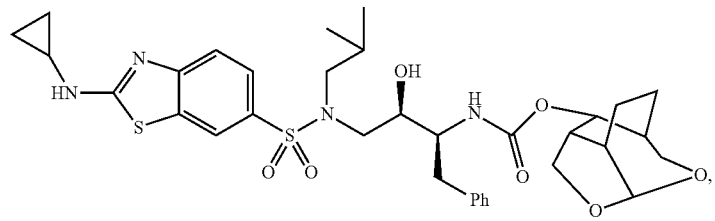
G-1
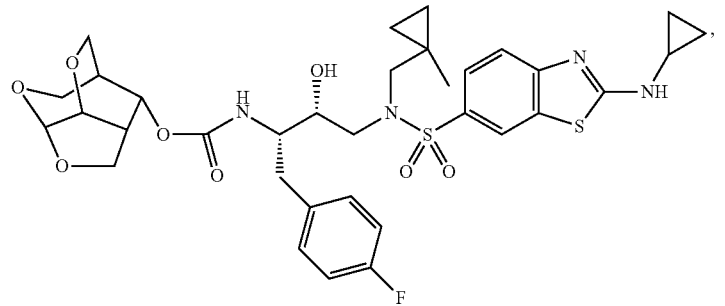
H-1
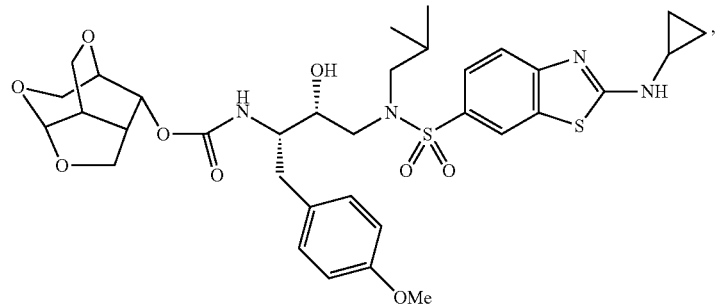
I-1
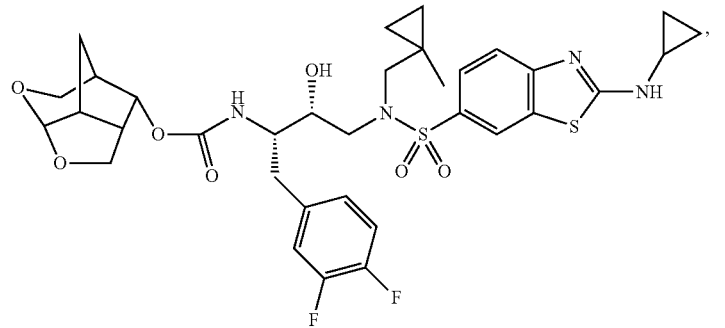
J-1
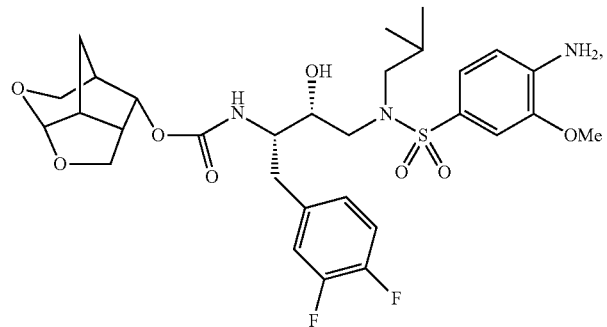

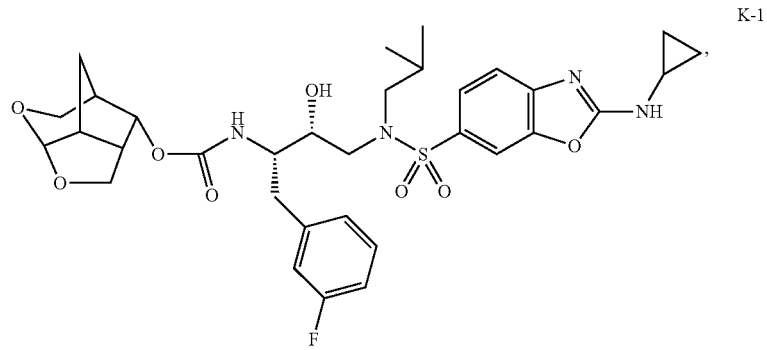
K-1
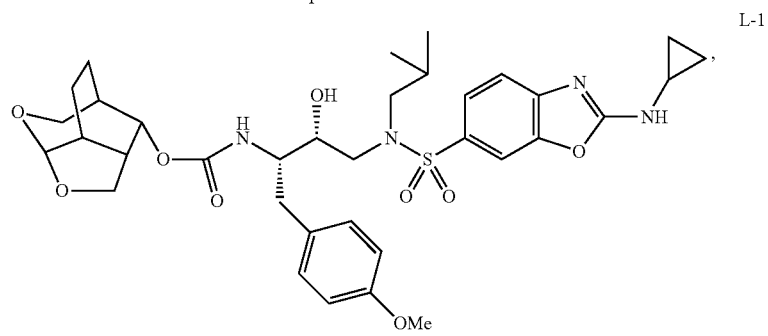
L-1
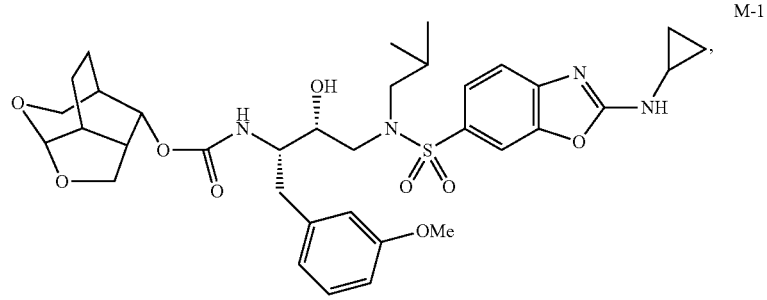
M-1
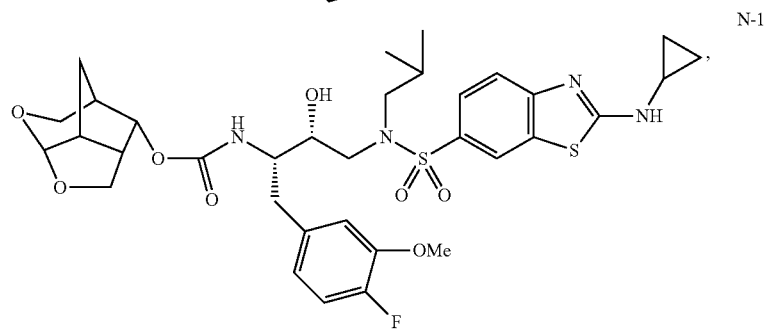
N-1
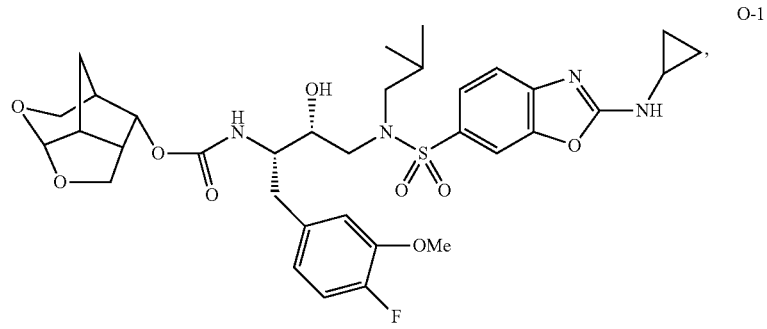
O-1
or a pharmaceutically acceptable salt, polymorph, prodrug, solvate or clathrate thereof.

Embodiments of the present invention also contemplate a compound of the formula:
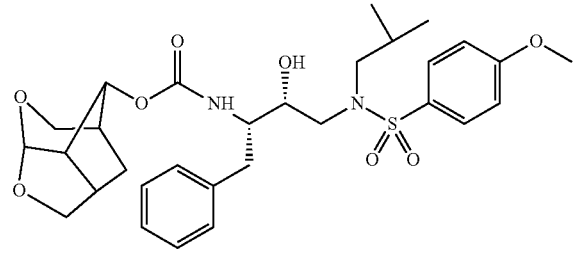 [SMILES: COc1ccc(S(=O)(=O)N(CC(C)C)C[C@@H](O)[C@H](Cc2ccccc2)NC(=O)OC2C3COC4OCC(C3)C42)cc1]
or a pharmaceutically acceptable salt, polymorph, prodrug, solvate or clathrate thereof.
Examples of the compounds of the formula (I), (Ia)-(Ih) also include, but are not limited to:
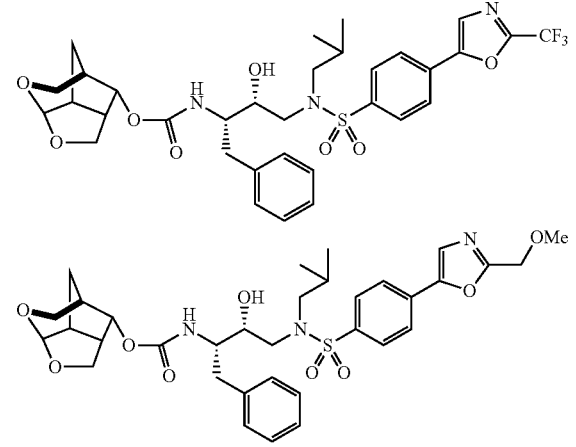
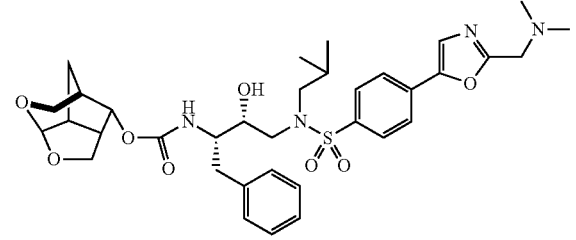
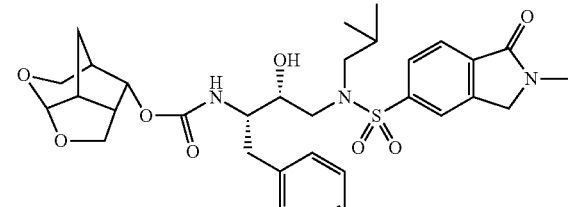
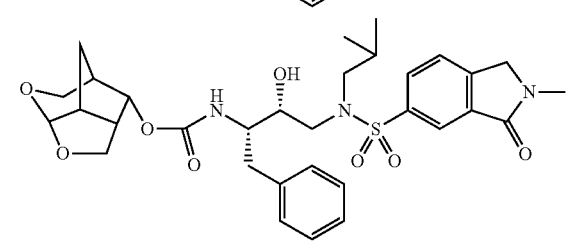
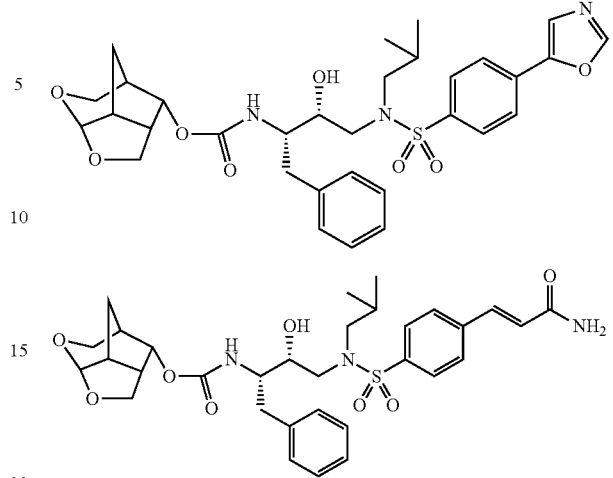

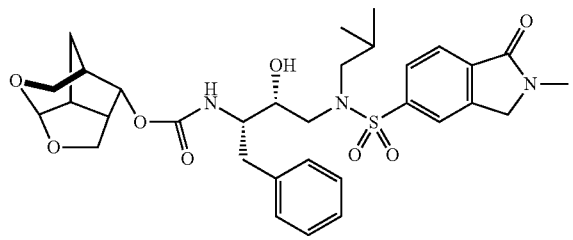
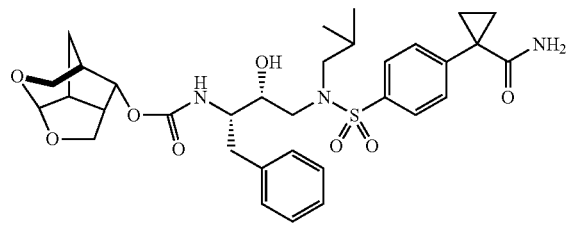
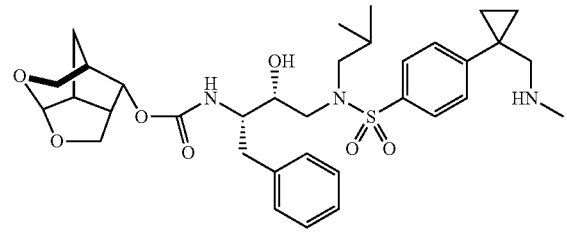
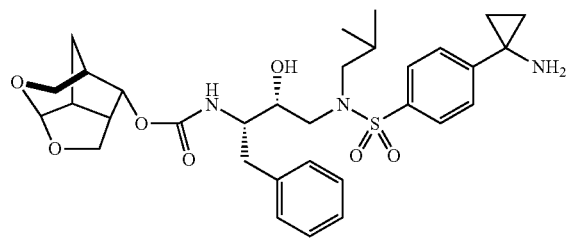
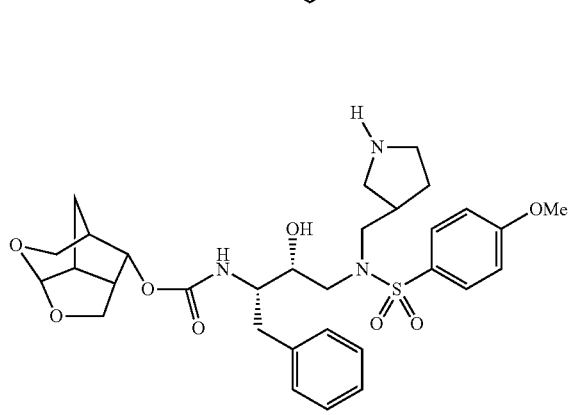
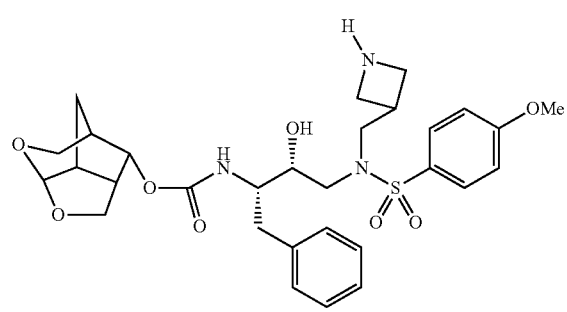
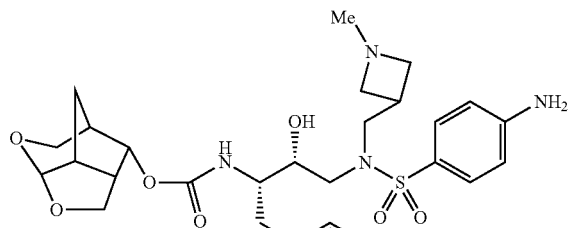
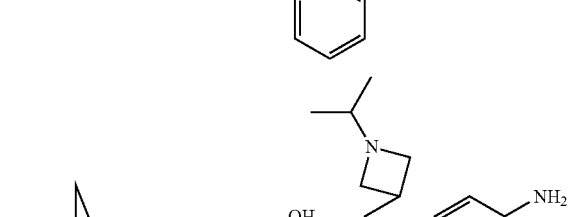
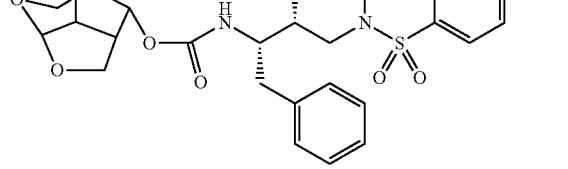
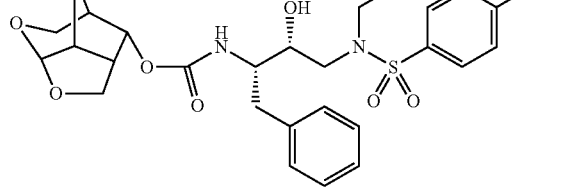
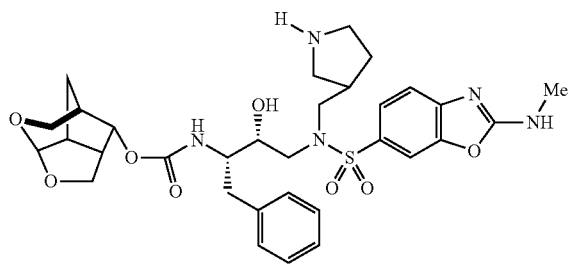
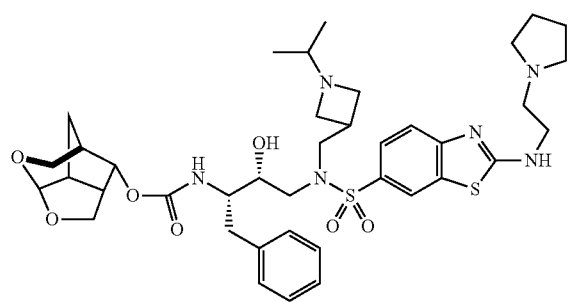

35
-continued
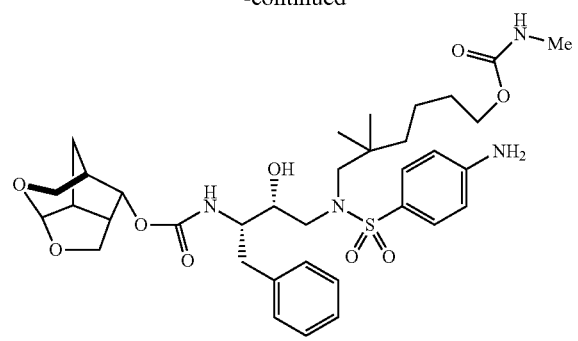
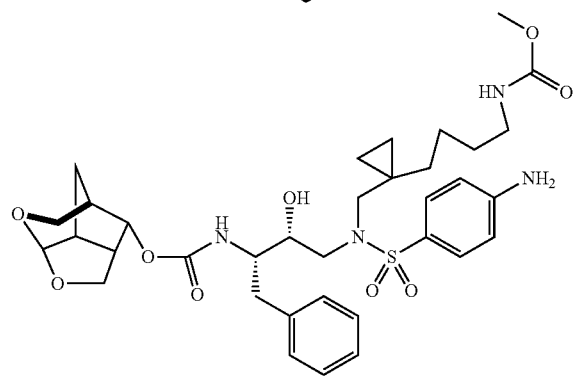
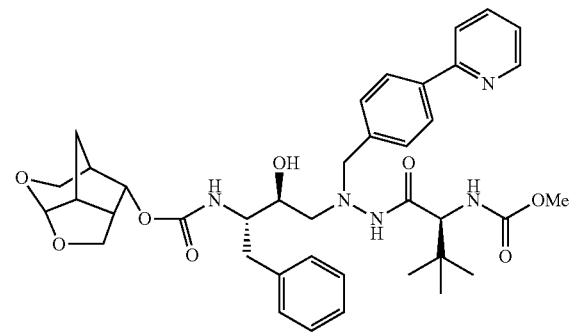
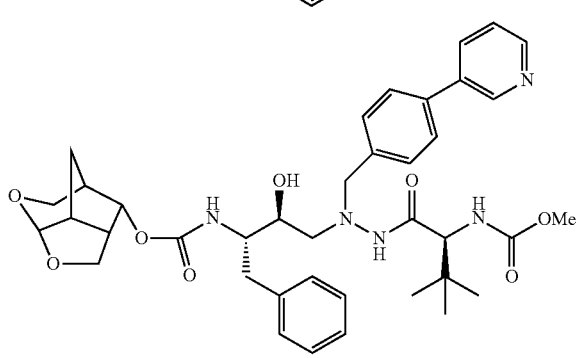
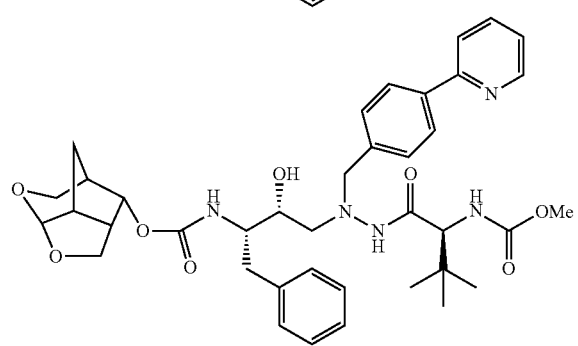
36
-continued
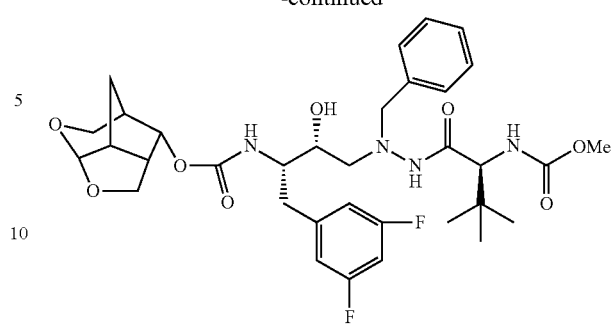
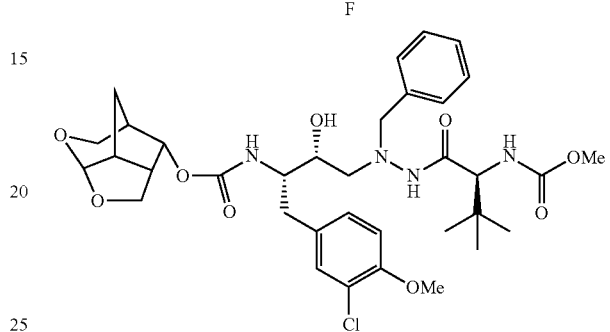
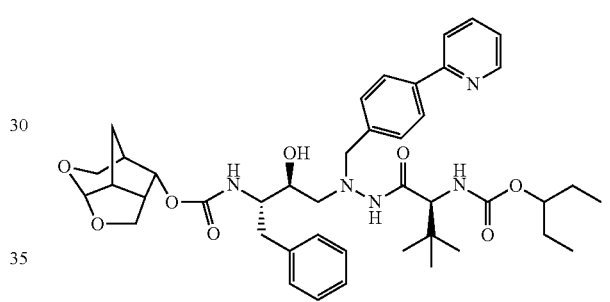
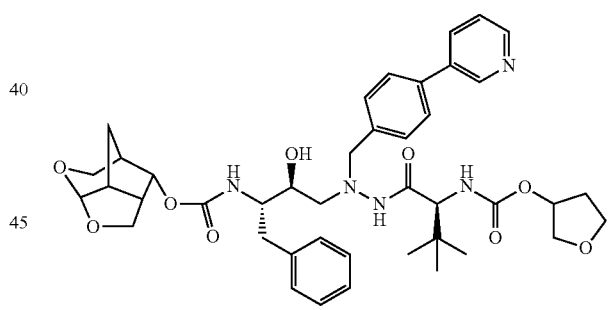
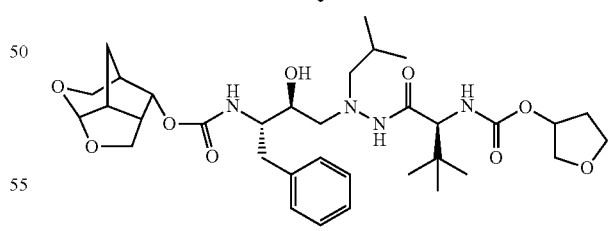
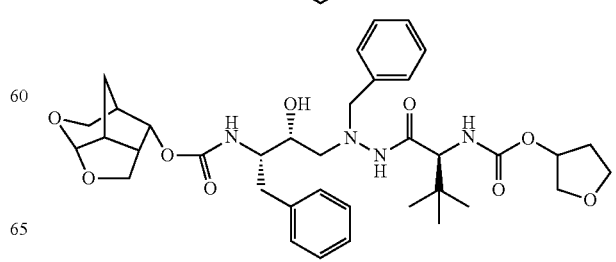

37
-continued
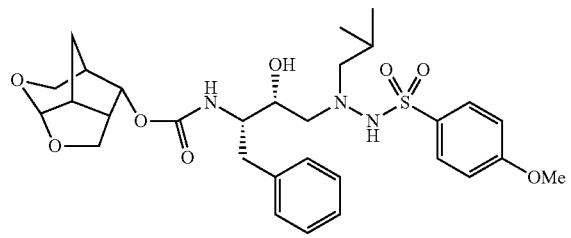
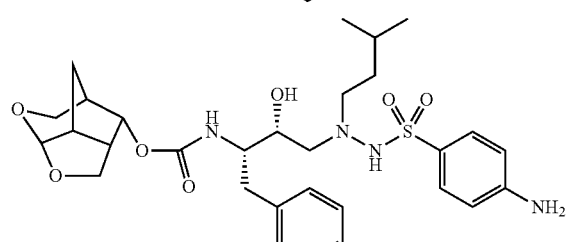
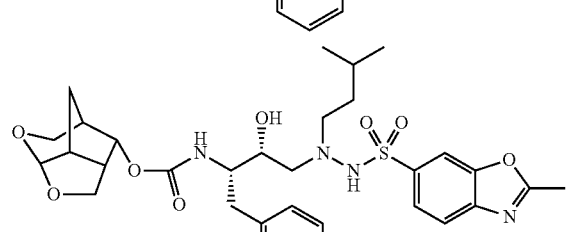
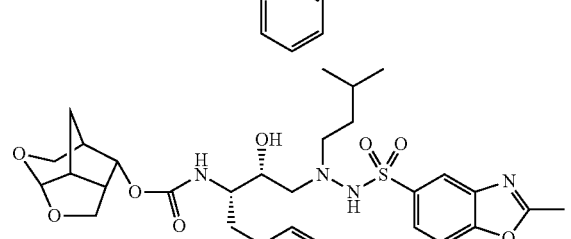
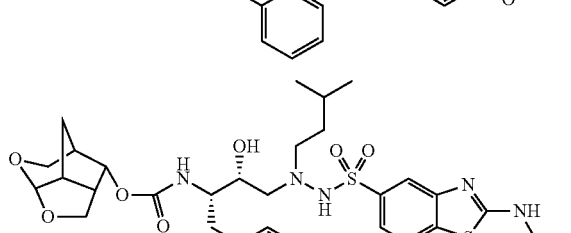
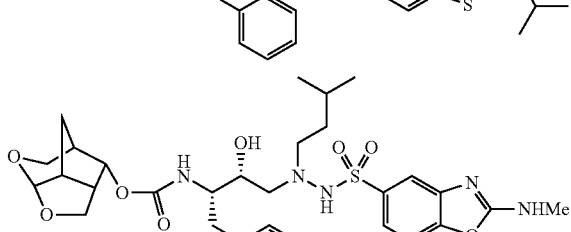
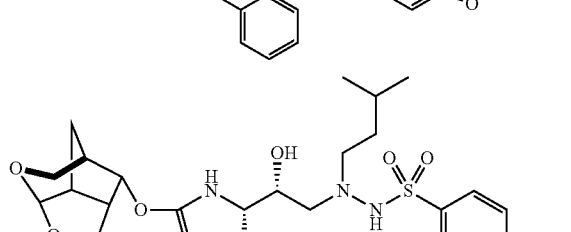
38
-continued
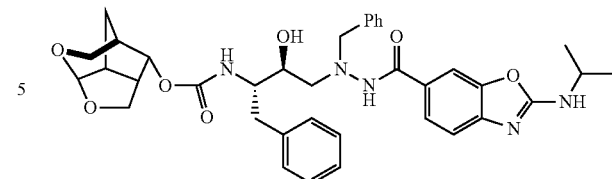
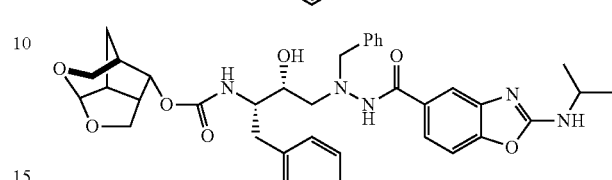
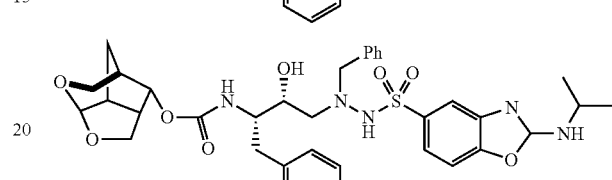
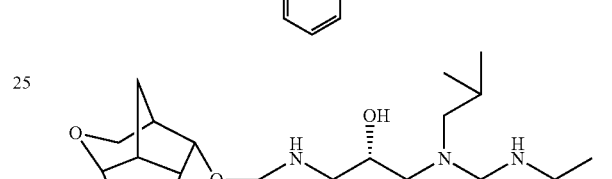
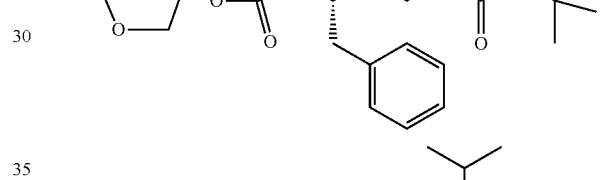
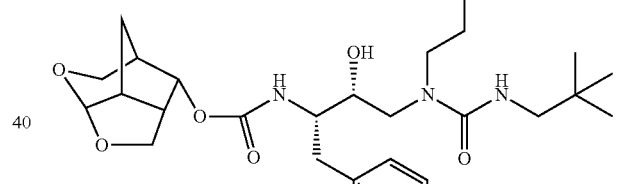
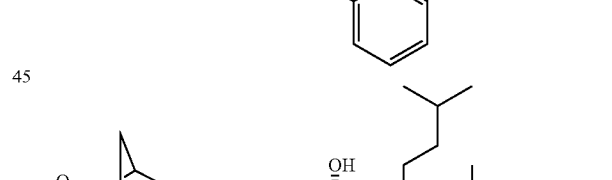
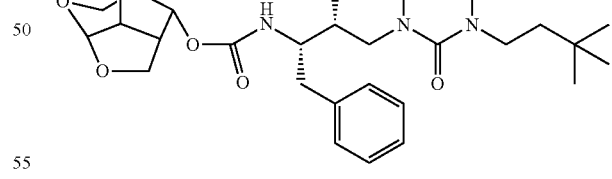
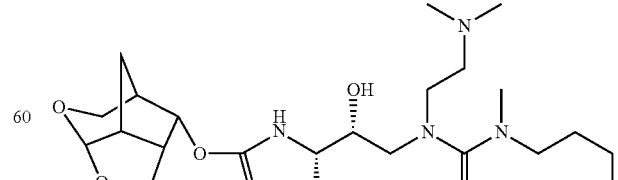

-continued

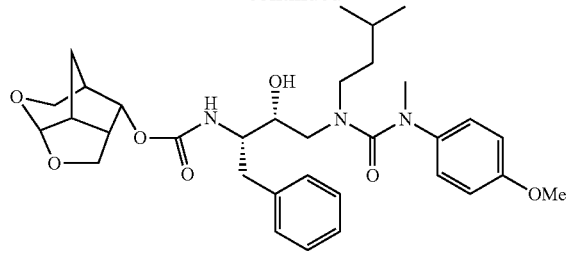
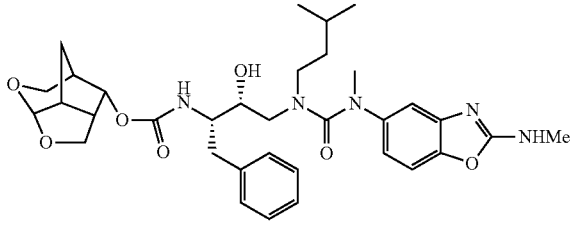
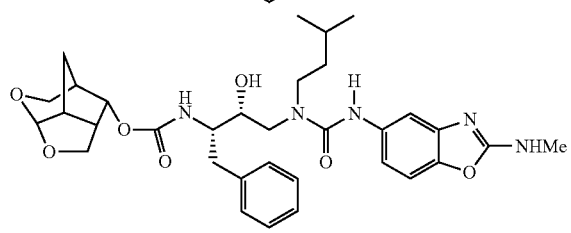
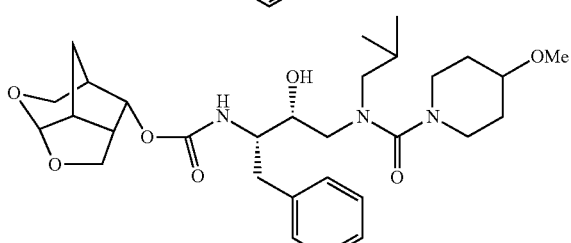
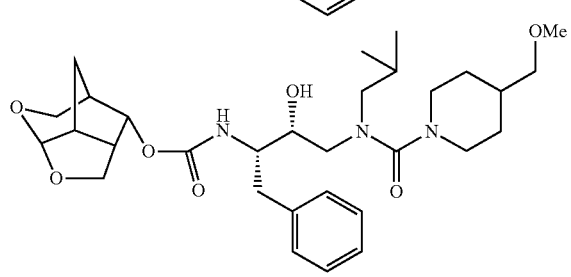
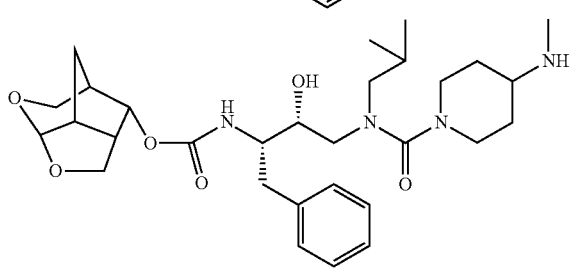
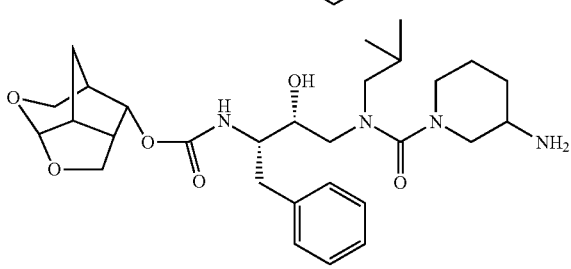

-continued

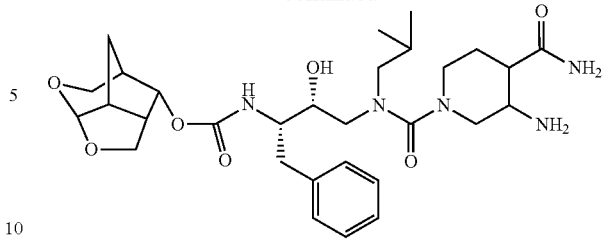
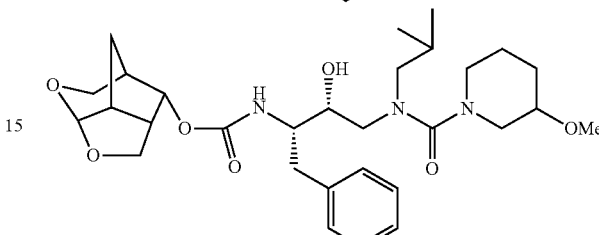
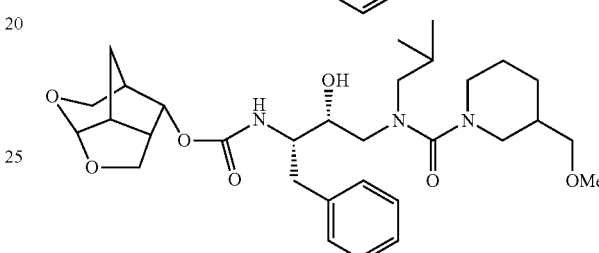
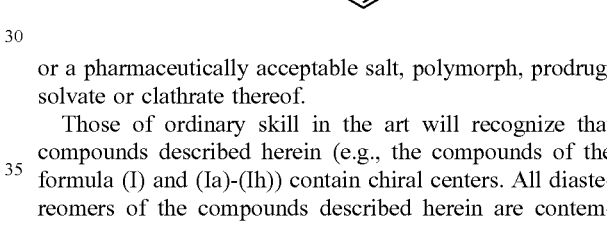

or a pharmaceutically acceptable salt, polymorph, prodrug, solvate or clathrate thereof.

Those of ordinary skill in the art will recognize that compounds described herein (e.g., the compounds of the formula (I) and (Ia)-(Ih)) contain chiral centers. All diastereomers of the compounds described herein are contemplated herein, as well as racemates. Thus, for example, the compounds of formula (I) and (Ia)-(Ih) are contemplated herein, as well as racemates.

Various embodiments of the present invention also contemplate pharmaceutical compositions comprising one or more compounds of the various embodiments of the present invention (e.g. a compound of the formula (I) and (Ia)-(Ih)) and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multilayer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the present invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

In some embodiments, the various embodiments of the present invention contemplate compositions comprising a therapeutically effective amount of one or more compounds of the various embodiments of the present invention (e.g. a compound of the formula (I) and (Ia)-(Ih)). In some embodiments, the compositions are useful in a method for treating an HIV (e.g., HIV-1) infection or AIDS, the method comprising administering a therapeutically effective amount of one or more compounds of any preceding claim to a patient in need thereof. In some aspects, the various embodiments of the present invention contemplate a compound of the formula (I) and (Ia)-(Ih) for use as a medicament for treating a patient in need of relief from an HIV infection or AIDS.

The term "therapeutically effective amount" as used herein, refers to that amount of one or more compounds of the various embodiments of the present invention (e.g. a compound of the formula (I) and (Ia)-(Ih)) that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

In some embodiments, the compounds of the various embodiments of the present invention have an HIV-1 protease inhibition constant ($K_i$) of from about 1 fM to about 200 nM (e.g., about 100 fM to about 200 nM, about 100 fM to about 100 pM, about 250 fM to about 100 pM, about 500 fM to about 5 pM, about 5 pM to about 100 pM, about 50 pM to about 250 pM, about 500 pM to about 100 nM or about 300 pM to about 75 nM).

In other embodiments, the compounds of the various embodiments of the present invention have an antiviral activity in vitro against a wild-type laboratory strain, HIV-$1_{LAI}$ with half-maximal inhibitory concentration ($IC_{50}$) of from about 1 fM to about 200 nM (e.g., about 100 fM to about 200 nM, about 100 fM to about 100 pM, about 250 fM to about 100 pM, about 500 fM to about 5 pM, from about 10 pM to about 50 nM, about 10 pM to about 500 pM, about 100 pM to about 750 pM, about 500 pM to about 1 nM or about 500 pM to about 50 nM).

In still other embodiments, the compounds of the various embodiments of the present invention have a darunavir-resistant HIV-1 variants (e.g., NL4-3R, $DRV_RP20$, $DRV_RP30$, and $DRV_RP51$) antiviral $IC_{50}$ of from about 200 fM to about 100 nM (e.g., from about 200 fM to about 600 fM, about 200 fM to about 50 pM, about 500 fM to about 500 pM, about 300 fM to about 1 pM). In yet other embodiments, the compounds of the various embodiments of the present invention have a darunavir-resistant HIV-1 variants (e.g., NL4-3R, $DRV_RP20$, $DRV_RP30$, and $DRV_RP51$) $IC_{50}$ of from about 50 pM to about 50 nM (e.g., from about 100 pM to about 50 nM or about 500 pM to about 10 nM). In still other embodiments, the compounds of the various embodiments of the present invention have a darunavir-resistant HIV-1 protease (e.g., NL4-3R, $DRV_RP20$, $DRV_RP30$, and $DRV_RP51$) antiviral $IC_{50}$ of from about 1 nM to about 100 nM (e.g., from about 10 nM to about 75 nM or about 10 nM to about 75 nM).

EXAMPLES

The present invention can be better understood by reference to the following examples which are offered by way of illustration. The present invention is not limited to the examples given herein.

The compounds of the various embodiments can be synthesized as described in the following examples.

(R)-Diphenyl(pyrrolidin-2-yl)methanol (6) was prepared from D-proline following the literature procedure. Periasamy, M.; Kanth, J. V. B. *Tetrahedron Lett.* 1993, 49, 5127. Treatment of (R)-diphenyl(pyrrolidin-2-yl)methanol (6) with tri-o-tolylboroxine 7, prepared from the corresponding boronic acid, under reflux in toluene gave catalytic precursor 1, which has been stored under argon as a molar solution in toluene (Scheme 1). Mukherjee, S.; Scopton, A. P.; Corey, E. J. *Org. Lett.* 2010, 12, 1836.

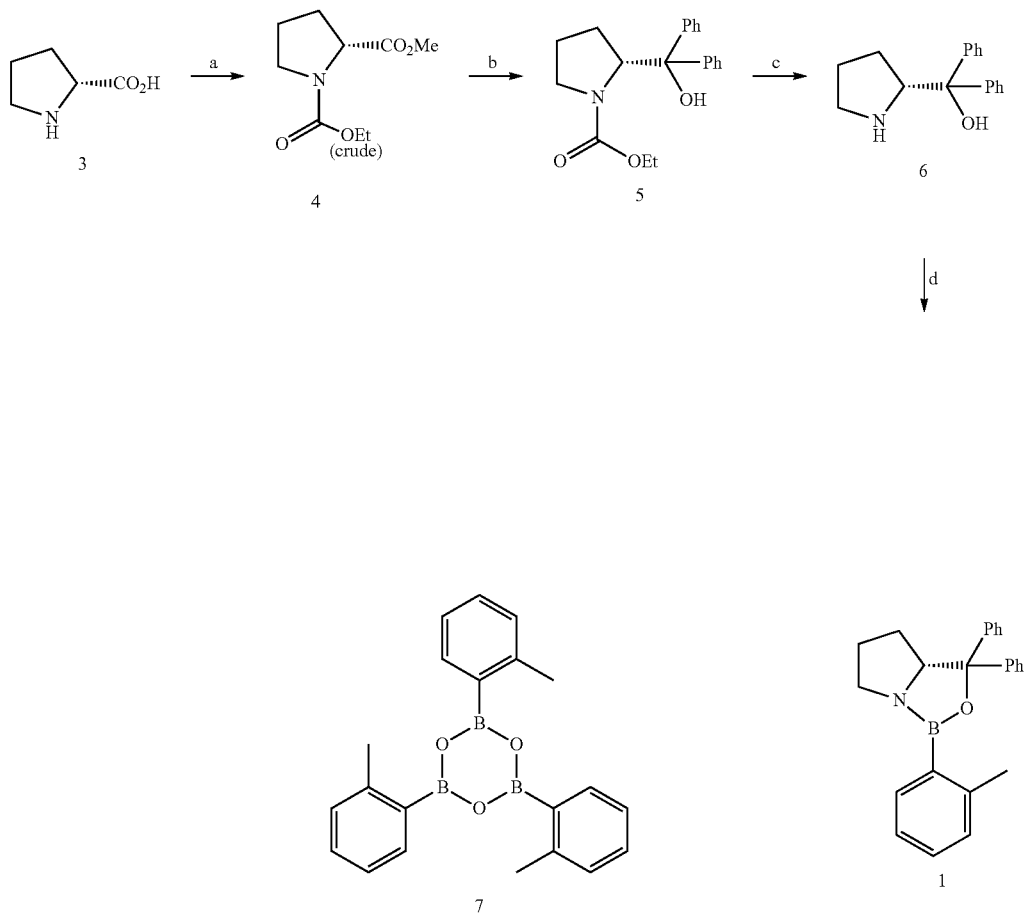

a) MeOH, EtOCOCl, K$_2$CO$_3$, 0-23° C., 16 h;
b) THF, PhMgBr, 0° C., 3 h;
c) MeOH, KOH, reflux, 48 h;
d) Toluene, 7, reflux, 20 h Catalyst precursor 2 has been prepared from L-proline following the similar procedure.

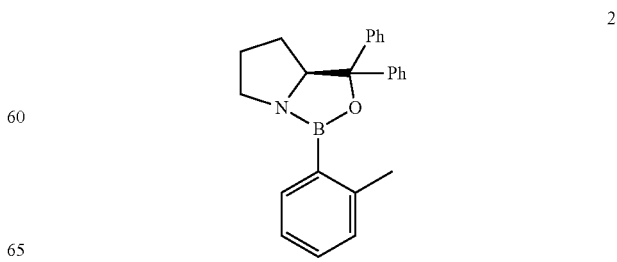

Synthesis of Ligand (15):

Diels-Alder reaction of vinyl boronate 8 with cyclopentadiene using Corey's protocol[3], followed by hydroboration of the resulting adduct using $H_2O_2$ and $KHCO_3$ provided alcohol 9 in 80% yield over two steps $\{[\alpha]_D = -141.5$ (c 1.04, $CHCl_3)\}$. Treatment of compound 9 with TBSOTf in the presence of 2,6-lutidine afforded compound 10 in 95% yield. Reduction of ester group of compound 10 with LAH, followed by a one-pot oxidative cleavage of olefin using a protocol developed by Nicolaou and co-workers, then treatment of resulting compound with DIBALH afforded compounds 11a and 11b as mixture (2:1 ratio) of diastereomers. This mixture was treated with TFA to obtain compound 12 in 74% yield. TBS deprotection of compound 12 using TBAF afforded alcohol 13 in 92% yield (Scheme 2).

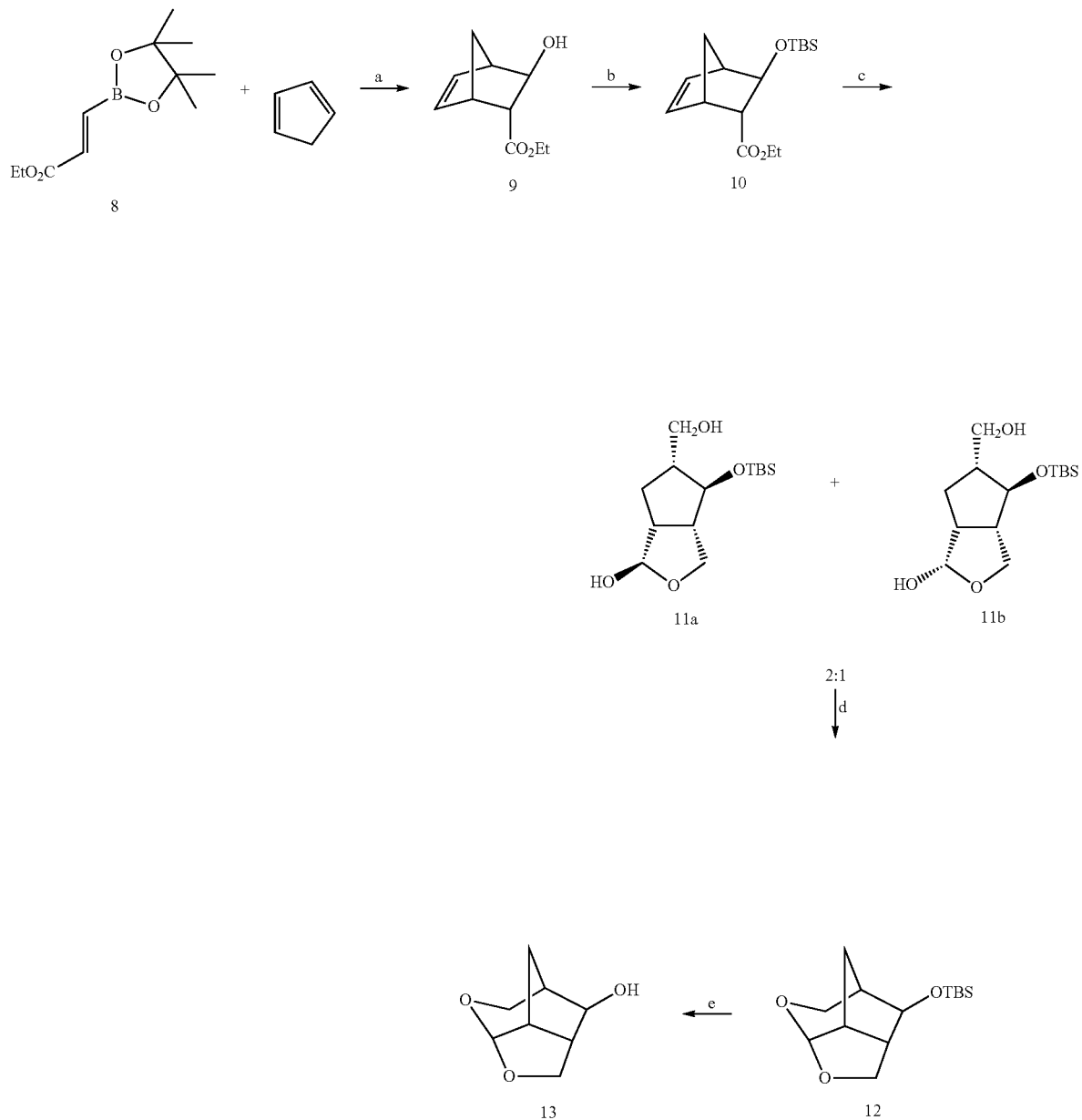

Scheme 2 a) 1. $CH_2Cl_2$, 1 (25 mol%), $Tf_2NH$ (20 mol%), -78° C., (2+5) h; 2. THF:EtOH (3:1), $KHCO_3$, $H_2O_2$, 0° C., 4.5 h; 80% (for 2 steps);
b) $CH_2Cl_2$, TBSOTf, 2,6-lutidine, 0-23° C., 45 min, 95%;
c) 1. THF, LAH, 0-23° C., 75 min; 2. Acetone:$H_2O$ (10:1), 2,6-lutidine, NMO, $OsO_4$, 23° C., 24 h & PhI(OAc)$_2$, 23° C., 15 h; 3.$CH_2Cl_2$, DIBALH, 0° C., 4 h, 62% (for 3 steps);
d) $CH_2Cl_2$, TFA, 0° C., 15 min & 23° C., 15 h, 74%;
e) THF, TBAF, 0-23° C., 2 h, 92%

Reaction of alcohol 13 with Dess-Martin periodinane followed by reduction of the resulting ketone with NaBH$_4$ provided epimeric alcohol 15 in 76% yields over two steps (Scheme 3).

Scheme 3

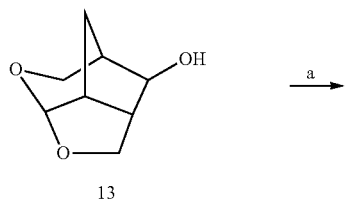

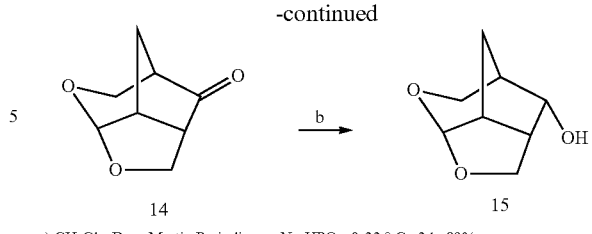

a) CH$_2$Cl$_2$, Dess-Martin Periodinane, Na$_2$HPO$_4$, 0-23 °C., 3 h, 89%;
b) MeOH, NaBH$_4$, 0° C., 45 min, 85%;

Synthesis of Ligand (Ent-15):

P2 ligand ent-15 has been prepared from vinyl boronate 8 and cyclopentadiene following the procedure as shown above.

Scheme 4

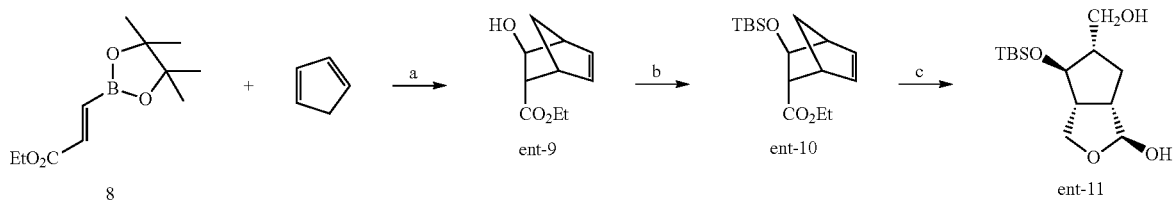

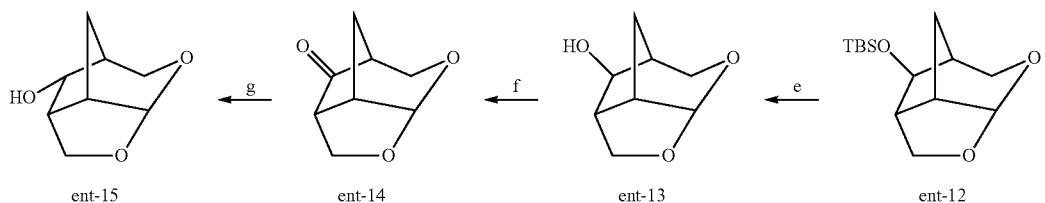

a) 1. CH$_2$Cl$_2$, 2 (25 mol%), Tf$_2$NH (20 mol%), -78° C., (2+5) h;
   2. THF:EtOH (3:1), KHCO$_3$, H$_2$O$_2$, 0° C., 4.5 h, 78%;
b) CH$_2$Cl$_2$, TBSOTf, 2,6-lutidine, 0-23° C., 45 min, 91%;
c) 1. THF, LAH, 0-23° C., 75 min;
   2. Acetone:H$_2$O (10:1), 2,6-lutidine, NMO, OsO$_4$, 23° C., 24 h & PhI(OAc)$_2$, 23° C., 15 h;
   3. CH$_2$Cl$_2$, DIBALH, 0° C., 4.5 h, 46% (for 3 steps);
d) CH$_2$Cl$_2$, TFA, 0-23° C., 15 h, 70%;
e) THF, TBAF, 0-23° C., 2 h, 88%;
f) CH$_2$Cl$_2$, Dess-Martin Periodinane, Na$_2$HPO$_4$, 0-23° C., 3 h, 86%;
g) MeOH, NaBH$_4$, 0° C., 45 min, 85%

Synthesis of Ligand 21:

Diels-Alder reaction of vinylboronate 8 with cyclohexadiene using Corey's protocol (with a slight modification) followed by hydroboration of the resulting adduct using $H_2O_2$ and $KHCO_3$ provided alcohol 16 in 79% yield over two steps $\{[\alpha]_D=-50.37$ (c 0.81, $CHCl_3)\}$. Mukherjee, S.; Corey, E. J. *Org. Lett.* 2010, 12, 1024. This alcohol 16 has been converted into P2 ligand 21 following the similar reaction sequence as shown in above. Treatment of alcohol 16 with TBSOTf in the presence of 2,6-lutidine afforded compound 17 in 89% yield. Reaction of compound 17 with LAH, followed by a one-pot oxidative cleavage of olefin using a protocol developed by Nicolaou and co-workers, then treatment of resulting compound with DiBALH afforded compound 18 (as a mixture of diastereomers) in 61% yield over three steps. Treatment of above mixture 18 with TFA provided compound 19 in 25% yield. TBS deprotection using TBAF followed by oxidation of the resulting alcohol using Dess-Martin periodinane afforded corresponding ketone 20 in 61% yield over two steps. Reduction of this ketone using $NaBH_4$ provided the epimeric alcohol 21 in 79% yield (Scheme 5).

Scheme 5

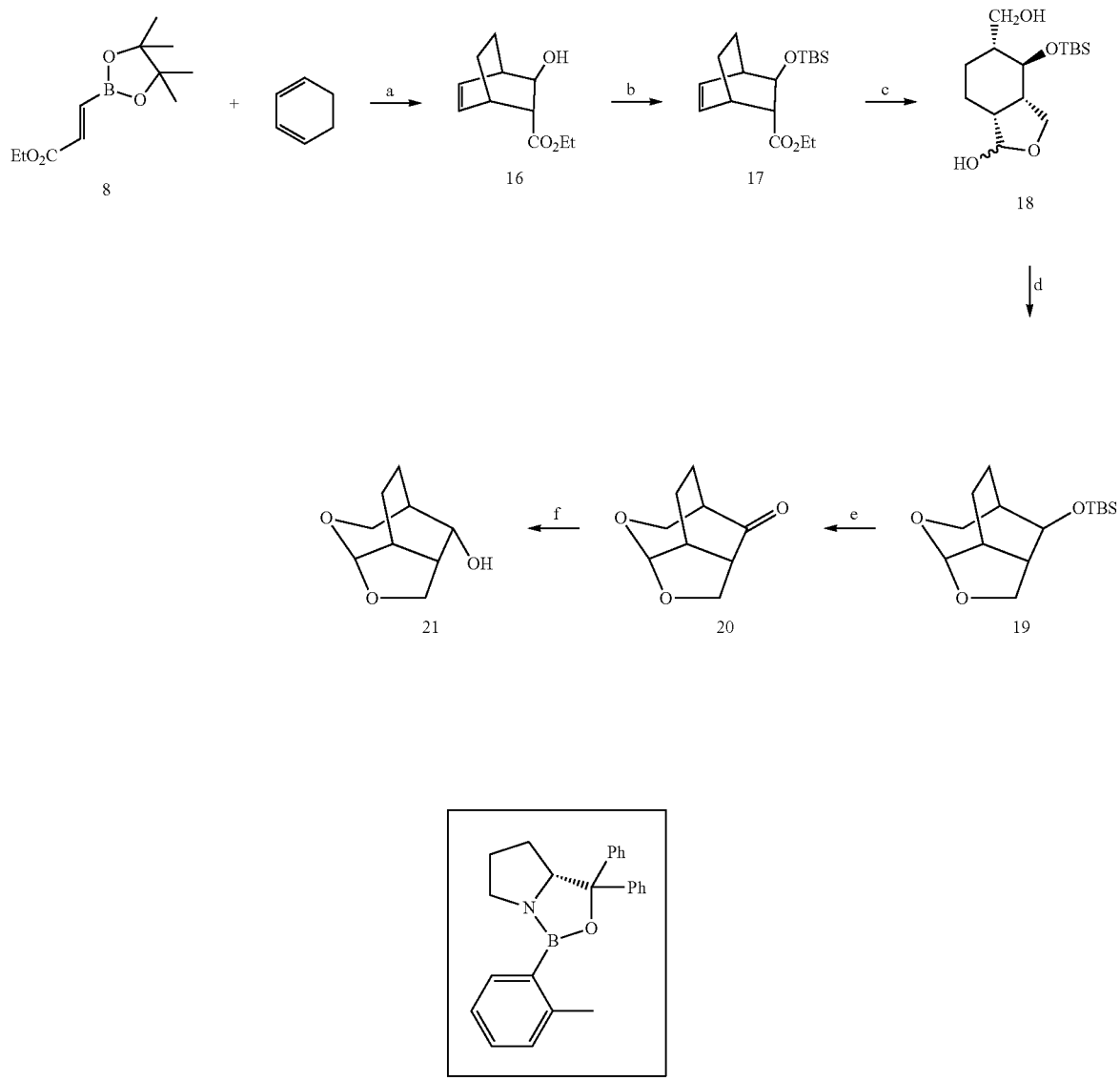

a) 1. $CH_2Cl_2$, 1 (25 mol%), $Tf_2NH$ (20 mol%), -78 to 23° C., 45 h (at 23° C.);
   2. THF:EtOH (3:1), $KHCO_3$, $H_2O_2$, 0° C., 4.5 h, 79% (for 2 steps);
b) $CH_2Cl_2$, TBSOTf, 2,6-lutidine, 0-23° C., 1 h, 89%;
c) 1. THF, LAH, 0-23° C., 75 min;
   2. Acetone:$H_2O$ (10:1), 2,6-lutidine, NMO, $OsO_4$, 23° C., 24 h & PhI(OAc)$_2$, 23° C., 14 h;
   3. $CH_2Cl_2$, DIBALH, 0° C., 4 h, 61% (for 3 steps);
d) $CH_2Cl_2$, TFA, 0° C., 15 min & 23° C., 18 h, 25%;
e) 1. THF, TBAF, 0-23° C., 2 h, 70%;
   2. $CH_2Cl_2$, Dess-Martin Periodinane, $Na_2HPO_4$, 0-23° C., 22 h, 87%;
f) MeOH, $NaBH_4$, 0° C., 1 h, 79%

Synthesis of Mixed Carbonates:

Mixed carbonates 22a, 22b, ent-22a, ent-22b and 22c were prepared by the treatment of respective alcohol with 4-nitrophenyl chloroformate in the presence of NMM or pyridine as described by us previously[4] to provide mixed carbonates in 83-95% yields (Scheme 6).

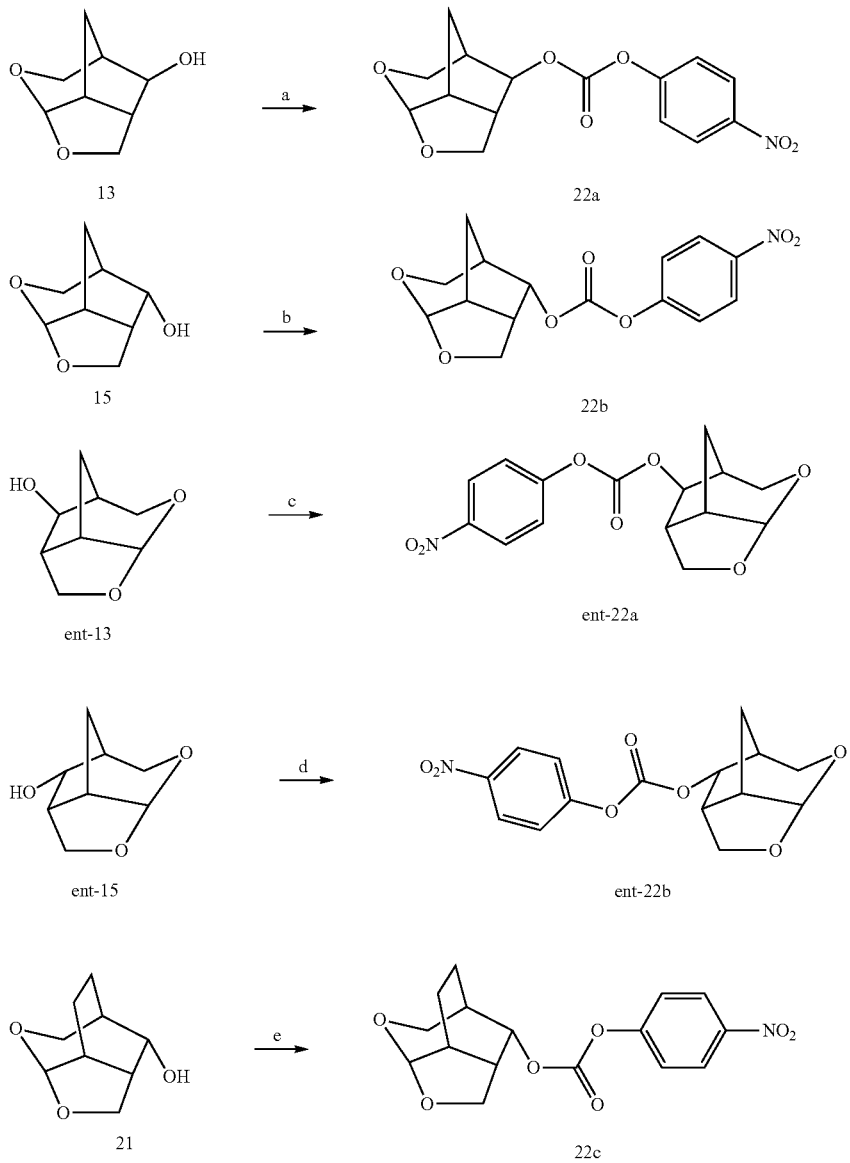

Scheme 6 a) $CH_2Cl_2$, 4-$NO_2$PhOCOCl, Pyridine, 0-23 °C., 1 h, 90%;
b) $CH_2Cl_2$, 4-$NO_2$PhOCOCl, Pyridine, 0-23° C., 2 h, 94%;
c) $CH_2Cl_2$, 4-$NO_2$PhOCOCl, NMM, 0-23° C., 1 h, 95%;
d) $CH_2Cl_2$, 4-$NO_2$PhOCOCl, Pyridine, 0-23° C., 2 h, 83%
e) $CH_2Cl_2$, Pyridine, 4-$NO_2$PhOCOCl, 0-23° C., 8 h, 93%;

Synthesis of HIV Protease Inhibitors:

Treatment of mixed carbonates 22a and 22b, ent-22a and ent-22b and 22c with known amine 23 in the presence of DIPEA provided inhibitors A-E in 77-93% yields (Scheme 7). See Ghosh, A. K.; Chapsal, B. D.; Parham, G. L.; Steffey, M.; Agniswamy, J.; Wang, Y.-F.; Amano, M.; Weber, I. T.; Mitsuya. H. J. Med. Chem. 2011, 54, 5890-5901.

Scheme 7
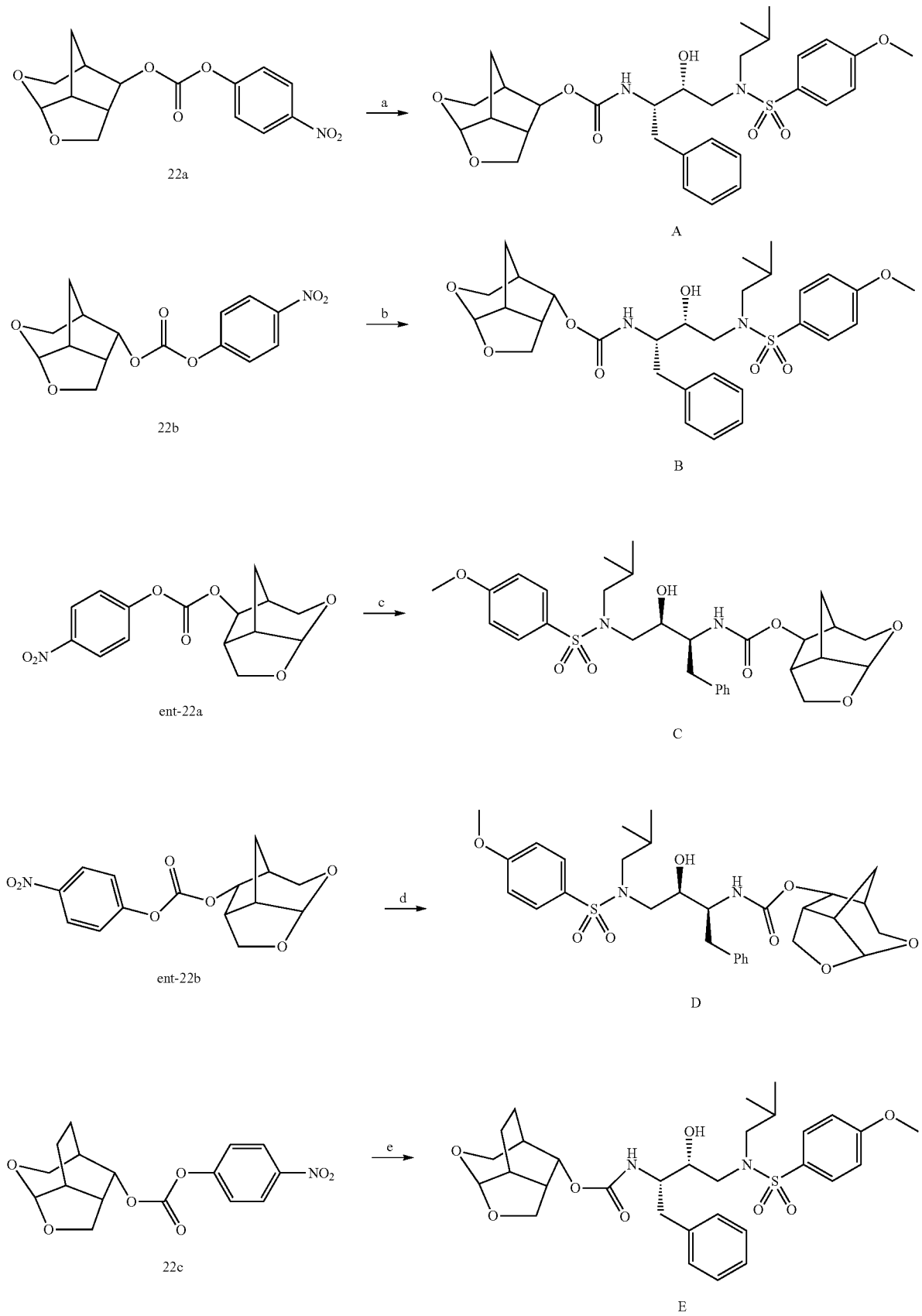

-continued

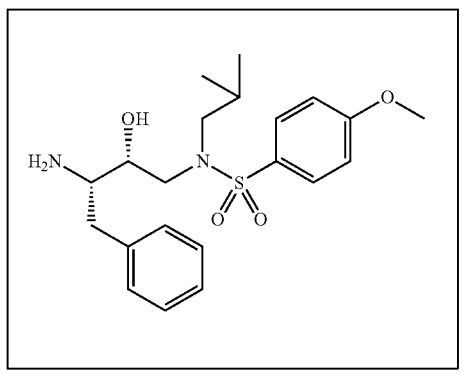

23 a) CH₃CN, 23, DIPEA, 23 °C., 5.5 d, 83%;
b) CH₃CN, 23, DIPEA, 23° C., 5.5 d, 89%;
c) H₃CN, 23, DIPEA, 23° C., 5.5 d, 81%;
d) CH₃CN, 23, DIPEA, 23° C., 5.5 d, 93%;
e) CH₃CN, 23, DIPEA, 23° C., 5 d, 77%

Inhibitors F-H were prepared from 22b, ent-22b and 22c by reacting with amine 24 Which was prepared by following similar procedure as 23 using 2-(cyclopropylamino)benzo[d]thiazole-6-sulfonyl chloride. See Ghosh, A. K.; Chapsal, B. D.; Parham, G. L.; Steffey, M.; Agniswamy, J.; Wang, Y.-F.; Amano, M.; Weber, I. T.; Mitsuya. H. *J. Med. Chem.* 2011, 54, 5890-5901. The reaction was carried out in the presence of DIPEA to provide inhibitors F-H (Yield 59-90%) (Scheme 8).

Scheme 8

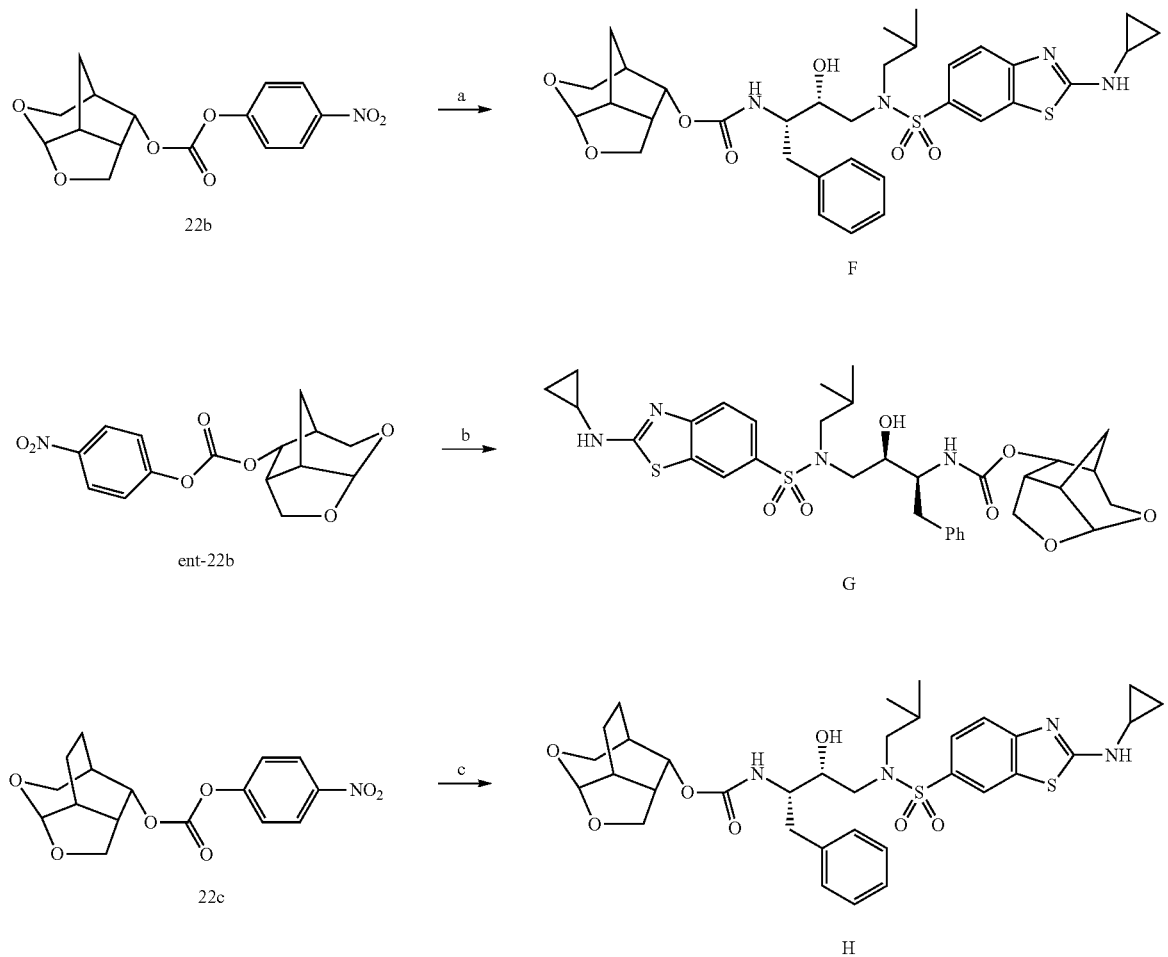

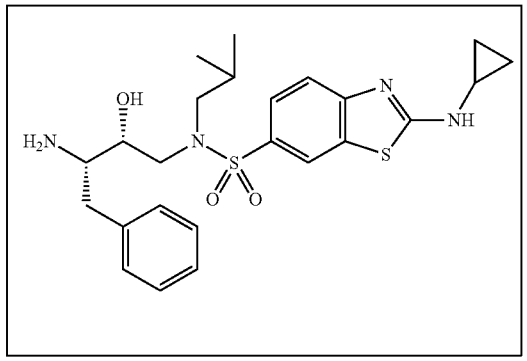

a) CH₃CN, 24, DIPEA, 23° C., 5.5 d, 90%;
b) CH₃CN, 24, DiPEA, 23° C., 5.5 d, 68%;
c) CH₃CN, 25, DIPEA, 23° C., 6 d, 59%;

We have prepared inhibitors I and J by the treatment of mixed carbonates 22b and 22c with amine 25 which was prepared from commercially available difluorophenyl alanine as the key starting material by following the similar procedure as amine 24. Inhibitor K was prepared by the reaction of amine 26 with mixed carbonate 22b (Scheme 9). See Ghosh, A. K.; Chapsal, B. D.; Parham, G. L.; Steffey, M.; Agniswamy, J.; Wang, Y.-F.; Amano, M.; Weber, I. T.; Mitsuya. H. *J. Med. Chem.* 2011, 54, 5890-5901.

Scheme 9

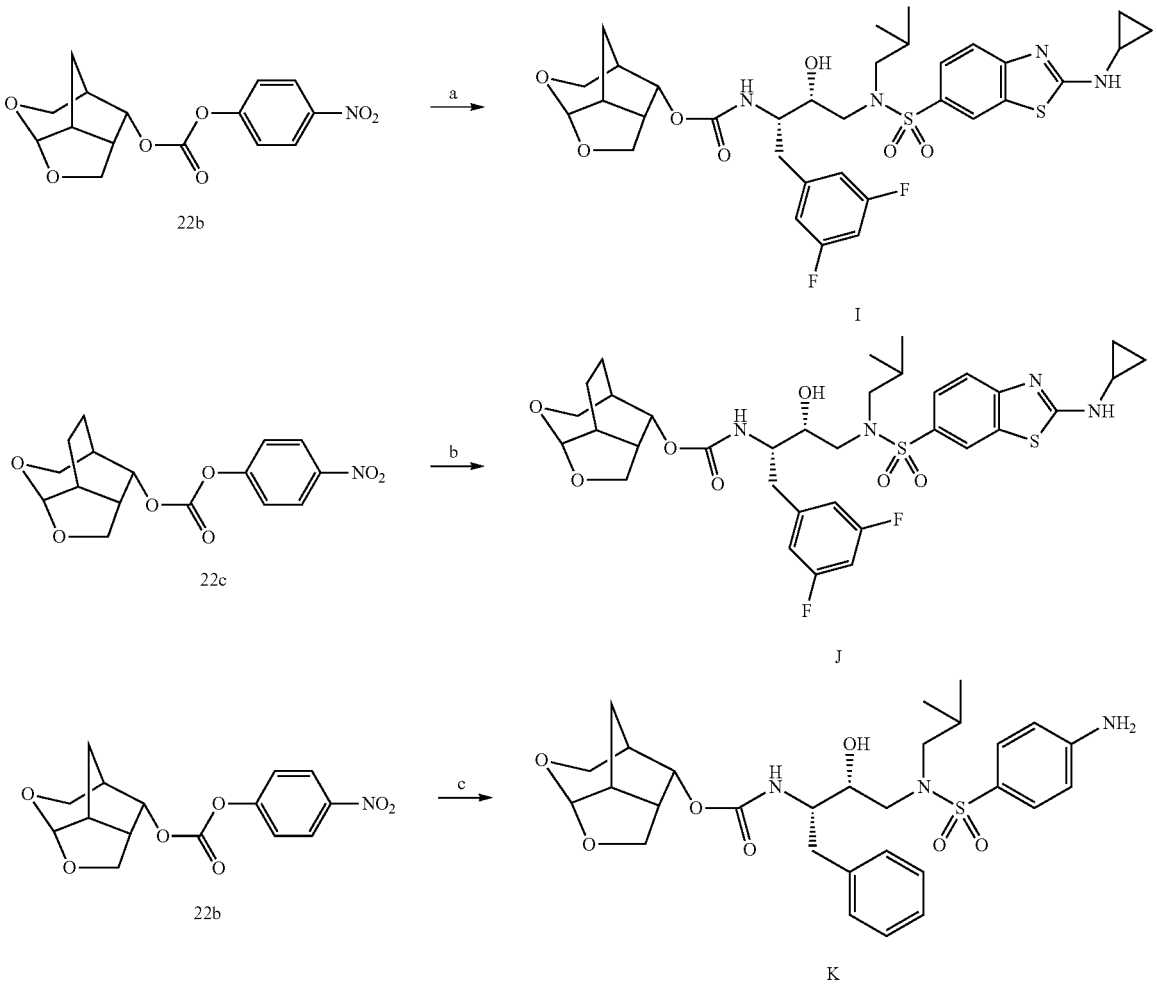

25

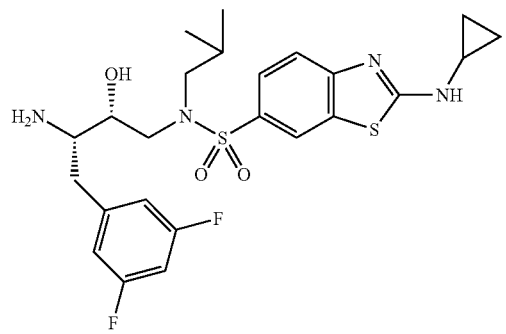

26

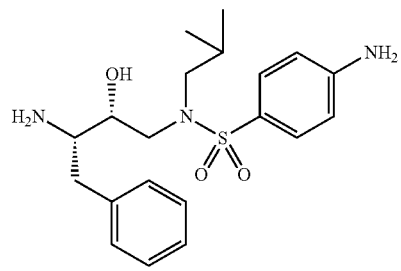

a) CH₃CN, 25, DIPEA, 23° C., 5.5 d, 79%;
b) CH₃CN, 25, DIPEA, 23° C., 6.5 d, 76%;
c) CH₃CN, 26, DIPEA, 23° C., 6 d, 80%;

Inhibitors M and N can be prepared by the treatment of mixed carbonates 22b and 22c with amine 27 as described previously (Scheme 10). See Ghosh, A. K.; Chapsal, B. D.; Parham, G. L.; Steffey, M.; Agniswamy, J.; Wang, Y.-F.; Amano, M.; Weber, I. T.; Mitsuya. H. *J. Med. Chem.* 2011, 54, 5890-5901; and Dierynck, I.; Van Marck, H.; Van Ginderen, M.; Jonckers, T. H. M.; Nalam, M. N. L.; Schiffer, C. A.; Raoof, A.; Kraus, G.; Picchio, G. *Antimicrob. Agents Ch.* 2011, 55, 5723-5731.

Scheme 10

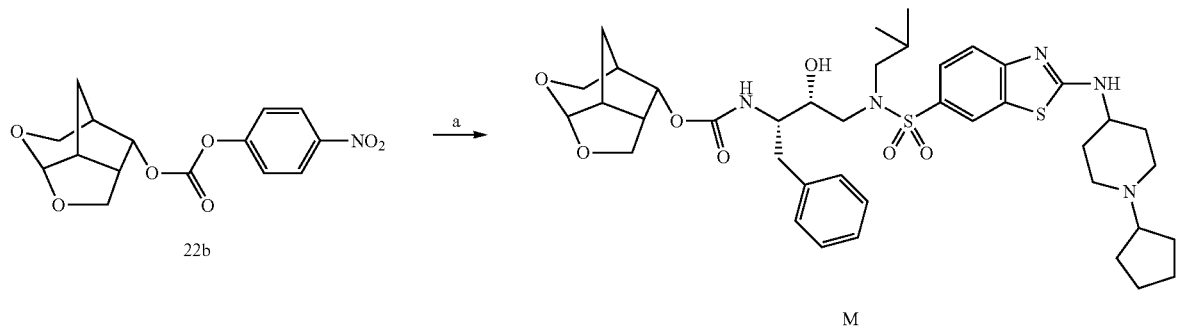

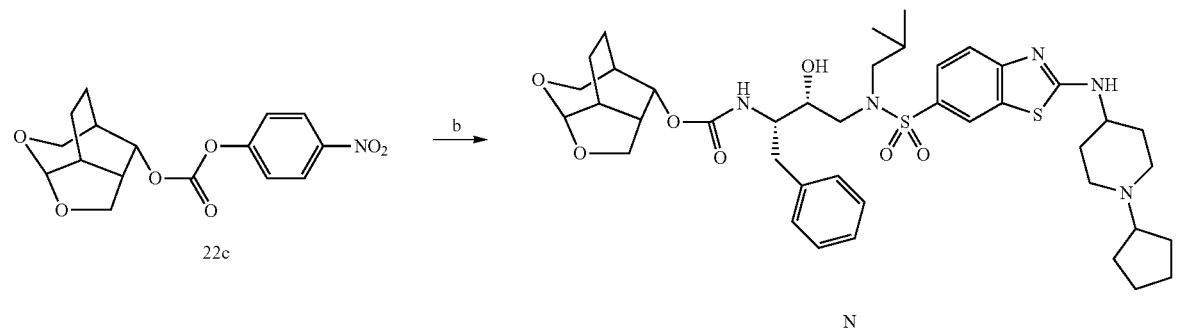

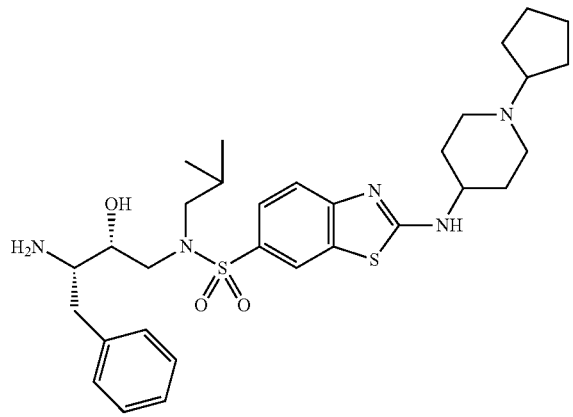

a) CH₃CN, 27, DIPEA, 23° C.,
b) CH₃CN, 27, DIPEA, 23° C.

Synthesis of Ligands:
Preparation of Compound 9:

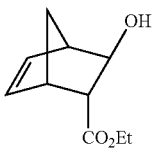

9

To an oven and flame dry two neck round bottom flask, was added a solution of oxazaborolidine 1 (1.25 mmol, 5 mL, 0.25M solution in Toluene). Solvent was removed carefully under reduced pressure and the resulting residue was dissolved in 2 mL absolute CH₂Cl₂ (distilled over CaH₂, degassed and dried over MS 4A). It was cooled to −25° C. and a solution of Tf₂NH (1 mmol, 0.281 g in 2 mL abs. CH₂Cl₂) was added. After stirring the resulting reaction mixture for 30 min at −25° C., solvent was removed carefully under reduced pressure at the same temperature. Now a solution of vinyl boronate 8 (5 mmol, 1.13 g in 3 mL abs CH₂Cl₂) was added to the resulting residue. Reaction mixture was cooled to −78° C. and cyclopentadiene (2.1 mL) was added over 2 h using syringe pump. After stirring for further 5 h at −78° C., reaction mixture was diluted with Et₂O, warm to room temperature and then filtered through celite. Filtrate was concentrated under reduced pressure and the resulting residue was purified by silica gel flash column chromatography (hexanes—10% ethyl acetate/hexanes) to obtain corresponding Diels-Alder adduct (contains some dieneophile and has been used in the next without further purification).

To a mixture of above Diels-Alder adduct and KHCO₃ (10 mmol, 5 mL, 2 M aqueous solution) in THF:EtOH (20 mL, 3:1), H₂O₂ (20 mmol, 2 mL, 30% wt solution in H₂O) was added slowly at 0° C. The resulting reaction mixture was stirred for 4.5 h at 0° C. and then quenched with aqueous Na₂S₂O₃ solution. Resulting mixture was extracted with ethyl acetate and combined extracts were washed with H₂O and brine. Combined organic layers were dried over anhydrous Na₂SO₄, filtered and solvent was removed under reduced pressure. The resulting residue was purified by silica gel flash column chromatography (25-30% ethyl acetate/hexanes) to obtain compound 9 in 80% yield over two steps (0.73 g).

¹H NMR (400 MHz, CDCl₃) δ 6.13 (dd, J=5.7, 2.7 Hz, 1H), 6.06 (dd, J=5.6, 3.3 Hz, 1H), 4.15-4.02 (m, 3H), 3.07 (brs, 1H), 2.78-2.73 (m, 1H), 2.66 (s, 1H), 2.61 (t, J=3.0 Hz, 1H), 1.88 (brd, J=8.7 Hz, 1H), 1.66-1.61 (m, 1H), 1.22 (t, J=7.1 Hz, 3H).

¹³C NMR (100 MHz, CDCl₃) δ 173.6, 137.2, 134.6, 75.5, 60.4, 55.0, 50.4, 46.3, 44.0, 14.2.

[α]$_D$=−141.5 (c 1.04, CHCl₃).

Preparation of Compound 10:

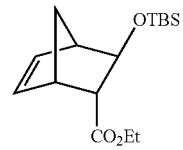

10

To a solution of alcohol 10 (4 mmol, 0.73 g) in CH₂Cl₂ (15 mL), 2,6-lutidine (12 mmol, 1.39 mL) and TBSOTf (6 mmol, 1.38 mL) were added at 0° C. and the resulting reaction mixture was stirred for 45 min at 23° C. Reaction was quenched with ice-cold 0.5N NaHSO₄ and extracted with CH₂Cl₂. Combined extracts were washed with brine, dried over anhydrous Na₂SO₄, filtered and solvent was removed under reduced pressure. The resulting residue was purified by silica gel flash column chromatography (4-6% diethyl ether/hexanes) to obtain compound 10 in 95% yield (1.13 g).

¹H NMR (400 MHz, CDCl₃) δ 6.13 (dd, J=5.7, 2.7 Hz, 1H), 6.04 (dd, J=5.6, 3.2 Hz, 1H), 4.13-4.04 (m, 2H), 4.04-4.01 (m, 1H), 3.03 (brs, 1H), 2.67-2.63 (m, 1H), 2.57 (dd, J=3.5, 2.3 Hz, 1H), 1.90 (brd, J=8.5 Hz, 1H), 1.60 (dABq, J=8.4, 3.3, 1.6 Hz, 1H), 1.23 (t, J=7.1 Hz, 3H), 0.88 (s, 9H), 0.07 (s, 3H), 0.06 (s, 3H).

¹³C NMR (100 MHz, CDCl₃) δ 173.7, 137.3, 134.4, 75.8, 60.1, 55.3, 51.2, 46.5, 44.0, 25.8, 17.9, 14.3, −4.9.

Preparation of Compound 11a and 11b:

To a solution of 10 (3.8 mmol, 1.13 g) in THF (15 mL), LAH (9.5 mmol, 0.36 g) was added at 0° C. Reaction mixture was warmed to 23° C. and stirred for 75 min at 23°

C. Reaction mixture was cooled back to 0° C., quenched with H₂O & 2N NaOH solution and then filtered. Filtrate was dried over anhydrous Na₂SO₄, filtered and solvent was removed under reduced pressure. The resulting compound alcohol was used in the next step without any further purification.

¹H NMR (400 MHz, CDCl₃) δ 6.14 (dd, J=5.7, 2.8 Hz, 1H), 6.02 (dd, J=5.7, 3.2 Hz, 1H), 3.59 (dd, J=10.5, 6.3 Hz, 1H), 3.36-3.25 (m, 2H), 2.80 (brs, 1H), 2.61-2.56 (m, 1H), 1.97-1.90 (m, 1H), 1.88 (dt, J=9.32, 1.53 Hz, 1H), 1.63 (dABq, J=8.3, 3.5, 1.7 Hz, 1H), 1.34 (brs, 1H), 0.87 (s, 9H), 0.05 (s, 3H), 0.04 (s, 3H).

¹³C NMR (100 MHz, CDCl₃) δ 137.3, 134.4, 75.6, 65.5, 53.2, 51.0, 46.7, 42.4, 25.8, 17.9, −4.6, −4.7.

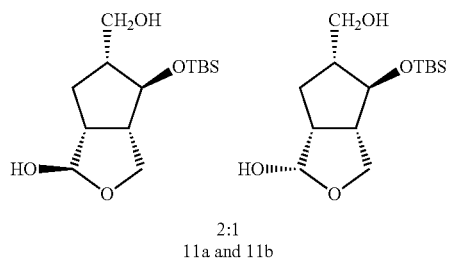 [SMILES: CC(C)(C)[Si](C)(C)O[C@@H]1[C@@H](CO)C[C@@H]2[C@H]1CO[C@H]2O ; CC(C)(C)[Si](C)(C)O[C@@H]1[C@@H](CO)C[C@@H]2[C@H]1CO[C@@H]2O]

2:1
11a and 11b

To a solution of above alcohol in acetone (32 mL) and H₂O (3.2 mL), 2,6-lutidine (7.6 mmol, 0.88 mL), NMO (5.7 mmol, 0.67 g) and OsO₄ (0.076 mmol, 0.48 mL, 4 wt. % in H₂O) were added at 23° C. After stirring the resulting reaction mixture for 24 h at 23° C., PhI(OAc)₂ (5.7 mmol, 1.84 g) was added and stirring was continued for further 15 h at the same temperature. Reaction was quenched with aqueous Na₂S₂O₃ solution and extracted with ethyl acetate. Combined extracts were washed with aqueous CuSO₄ solution, H₂O and brine. Organic layer was dried over anhydrous Na2SO4, filtered and solvent was removed under reduced pressure. The resulting residue was passed through silica gel flash column chromatography (20-25% ethyl acetate/hexanes) and was used directly in the next step.

To a solution of the above compound in CH₂Cl₂ (15 mL), DiBAL-H (7.2 mmol, 7.2 mL, 1M in in CH₂Cl₂) was added slowly at 0° C. and the resulting reaction mixture was stirred for 4 h 0° C. Reaction was quenched with sodium potassium tartrate and diluted with CH₂Cl₂. Resulting mixture was stirred until two layers were separated clearly. Organic layer was separated and aqueous layer was extracted with CH₂Cl₂. Combined extracts were washed with brine, dried over anhydrous Na₂SO₄, filtered and solvent was removed under reduced pressure. The resulting residue was purified by silica gel flash column chromatography (60% ethyl acetate/hexanes) to obtain lactols 11a and 11b in ≈2:1 diastereomeric ratio (62% yield over three steps, 0.675 g).

¹H NMR (400 MHz, CDCl₃) δ 5.36 (d, J=6.8 Hz, 0.5H), 5.20 (s, 1H), 4.16-4.06 (m, 2H), 3.97 (dd, J=8.9, 6.9 Hz, 0.5H), 3.92-3.77 (m, 3H), 3.69 (dd, J=10.6, 5.0 Hz, 1H), 3.64 (dd, J=8.4, 6.4 Hz, 1H), 3.59-3.48 (m, 1.5H), 2.77-2.53 (m, 3H), 2.53-2.35 (m, 3H), 2.08-1.93 (m, 2.5H), 1.82 (d, J=11.3 Hz, 0.5H), 0.86 & 0.856 (two singlets, 13.5H), 0.06, 0.04, 0.036&0.027 (four singlets, 9H).

¹³C NMR (100 MHz, CDCl₃) δ 104.0, 103.2, 86.1, 82.3, 73.1, 70.8, 64.7, 63.9, 52.5, 51.1, 50.8, 48.8, 45.3, 44.4, 29.5, 25.7, 25.4, 18.0, 17.8, −4.0, −4.7, −4.76, −4.79.

Preparation of Compound 12:

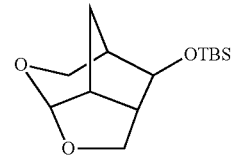

12

Trifluoroacetic acid (2.3 mL) was added to a solution above lactol mixture 11a & 11b (2.32 mmol, 0.67 g) in CH₂Cl₂ (60 mL) at 0° C. Resulting reaction mixture was stirred 15 min at 0° C. and 15 h at 23° C. Reaction was quenched with saturated NaHCO₃ and extracted with CH₂Cl₂. Combined extracts were washed with brine, dried over anhydrous Na₂SO₄, filtered and solvent was removed under reduced pressure. The resulting residue was purified by silica gel flash column chromatography (8-10% ethyl acetate/hexanes) to obtain compound 12 in 74% yield (0.462 g).

¹H NMR (400 MHz, CDCl₃) δ 5.36 (d, J=6.8 Hz, 1H), 4.11 (dd, J=9.0, 1.2 Hz, 1H), 3.97 (dd, J=8.9, 7.0 Hz, 1H), 3.87-3.79 (m, 2H), 3.51 (d, J=11.4 Hz, 1H), 2.74-2.67 (m, 1H), 2.42 (t, J=7.1 Hz, 1H), 2.06-1.92 (m, 2H), 1.83 (d, J=11.2 Hz, 1H), 0.86 (s, 9H), 0.04 (s, 3H), 0.03 (s, 3H).

¹³C NMR (100 MHz, CDCl₃) δ 104.0, 86.2, 73.1, 64.7, 52.5, 45.3, 44.4, 25.7, 25.4, 18.0, −4.75, −4.79.

Preparation of Compound 13:

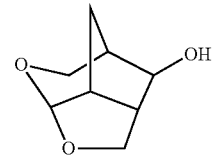

13

A solution of tetrabutylammonium fluoride (2.6 mmol, 2.6 mL, 1M solution in THF) was added to a solution of 12 (1.7 mmol, 0.46 g) in THF (10 mL) at 0° C. and the resulting reaction mixture was stirred for 2 h at 23° C. Solvent was removed under reduced pressure and the resulting residue was purified by silica gel flash column chromatography (70-80% ethyl acetate/hexanes) to obtain corresponding alcohol 13 in 92% yield (0.244 g).

¹H NMR (400 MHz, CDCl₃) δ 5.39 (d, J=6.8 Hz, 1H), 4.17 (dd, J=9.0, 1.2 Hz, 1H), 3.99 (dd, J=9.0, 6.9 Hz, 1H), 3.95 (s, 1H), 3.86 (dd, J=11.4, 8.5 Hz, 1H), 3.56 (d, J 15=11.5 Hz, 1H), 2.79-2.72 (m, 1H), 2.52-2.44 (m, 1H), 2.15-2.06 (m, 1H), 1.99 (dt, J=11.7, 4.3 Hz, 1H), 1.91 (d, J=11.7 Hz, 1H), 1.72 (s, 1H).

[α]_D=−24.48 (c 1.01, CHCl₃)

Preparation of Compound 15:

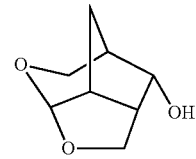

15

To a solution of alcohol 13 (0.64 mmol, 0.1 g) in CH$_2$Cl$_2$ (4 mL), Na$_2$HPO$_4$ (0.352 mmol, 50 mg) and Dess-Martin periodinane (0.83 mmol, 0.352 g) were added at 0° C. After stirring the reaction mixture for 3 h at 23° C., reaction was quenched with saturated NaHCO3 and aqueous Na$_2$S$_2$O$_3$ solutions respectively and then extracted with CH$_2$Cl$_2$. Combined extracts were washed with brine, dried over anhydrous Na$_2$SO$_4$, filtered and solvent was removed under reduced pressure. The resulting residue was purified by silica gel flash column chromatography (40% ethyl acetate/hexanes) to obtain corresponding ketone 14 in 89% yield (87.9 mg).

To a solution of the above ketone 14 (0.57 mmol, 87.9 mg) in MeOH (4 mL), NaBH$_4$ (2.85 mmol, 108 mg) was added at 0° C. Reaction mixture was stirred for 45 min at 0° C. Reaction was quenched with saturated NH$_4$Cl solution and diluted with ethyl acetate. Organic layer was separated and the aqueous layer was extracted with ethyl acetate. Combined extracts were washed with brine, dried over anhydrous Na$_2$SO$_4$, filtered and solvent was removed under reduced pressure. The resulting residue was purified by silica gel flash column chromatography (60-65% ethyl acetate/hexanes) to obtain alcohol 15 in 85% yield (75.6 mg).

$^1$H NMR (400 MHz, CDCl$_3$) δ 5.43 (d, J=6.4 Hz, 1H), 4.42 (d, J=9.4 Hz, 1H), 4.23 (dd, J=8.8, 5.7 Hz, 1H), 4.06 (d, J=11.4 Hz, 1H), 3.74 (dd, J=9.0, 6.3 Hz, 1H), 3.64 (dd, J=11.4, 7.8 Hz, 1H), 2.72-2.55 (m, 2H), 2.23 (ABq, J=12.0, 5.5 Hz, 1H), 1.98 (brs, 1H), 1.80 (d, J=12.0 Hz, 1H), 1.44 (dt, J=12.0, 3.9 Hz, 1H).

$^{13}$C NMR (100 MHz, CDCl$_3$) δ 104.2, 72.3, 68.0, 59.2, 45.1, 42.8, 39.2, 23.7

$[α]_D$=−9.27 (c 1.03, CHCl$_3$)

Enantiomeric ligand ent-15 was prepared using chiral catalyst 2 by following the same sequence of reaction as ligand 15

Ent-9:

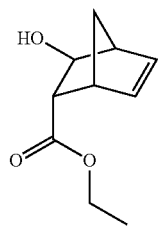

ent-9

Yield: 78%
$[α]_D$=+132.07 (c 0.69, CHCl$_3$) {Reported $[α]_D^{23}$=+137.0 (c 2.00, CHCl$_3$)}

Ent-10:

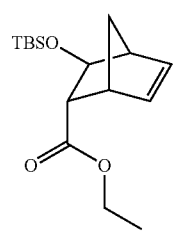

ent-10

Yield: 91%

Ent-11:

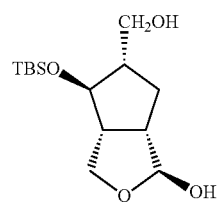

ent-11

To a solution of ent-10 (1.35 mmol, 0.4 g) in THF (7 mL), LAH (3.4 mmol, 0.13 g) was added at 0° C. Reaction mixture was warmed to 23° C. and stirred for 75 min at 23° C. Reaction mixture was cooled back to 0° C., quenched with H$_2$O & 2N NaOH solution and then filtered. Filtrate was dried over anhydrous Na$_2$SO$_4$, filtered and solvent was removed under reduced pressure. The resulting alcohol was used in the next step without any further purification.

To a solution of above alcohol in acetone (12 mL) and H$_2$O (1.2 mL), 2,6-lutidine (2.7 mmol, 0.31 mL), NMO (2.03 mmol, 0.24 g) and OsO$_4$ (0.027 mmol, 0.17 mL, 4 wt. % in H$_2$O) were added at 23° C. After stirring the resulting reaction mixture for 24 h at 23° C., PhI(OAc)$_2$ (2.03 mmol, 0.65 g) was added and stirring was continued for further 15 h at the same temperature. Reaction was quenched with aqueous Na$_2$S$_2$O$_3$ solution and extracted with ethyl acetate. Combined extracts were washed with aqueous CuSo$_4$ solution, H$_2$O and brine. Organic layer was dried over anhydrous Na2SO4, filtered and solvent was removed under reduced pressure. The resulting residue was passed through silica gel flash column chromatography (20-25% ethyl acetate/hexanes) and was used directly in the next step.

To a solution of the above compound in CH$_2$Cl$_2$ (6 mL), DiBAL-H (1.8 mmol, 1.8 mL, 1M in CH$_2$Cl$_2$) was added slowly at 0° C. and the resulting reaction mixture was stirred for 4.5 h 0° C. Reaction was quenched with sodium potassium tartrate and diluted with CH$_2$Cl$_2$. Resulting mixture was stirred until two layers were separated clearly. Organic layer was separated and aqueous layer was extracted with CH$_2$Cl$_2$. Combined extracts were washed with brine, dried over anhydrous Na$_2$SO$_4$, filtered and solvent was removed under reduced pressure. The resulting residue was purified by silica gel flash column chromatography (60% ethyl acetate/hexanes) to obtain desired compound ent-11 in 46% yield (over three steps, 0.18 g) (contains some minor impurity).

$^1$H NMR (400 MHz, CDCl$_3$) δ 5.19 (s, 1H), 4.15-4.08 (m, 1H), 3.84 (dd, J=9.0, 1.6 Hz, 1H), 3.68 (dd, J=10.6, 4.9 Hz, 1H), 3.62 (dd, J=8.5, 6.3 Hz, 1H), 3.54 (dd, J=10.6, 5.7 Hz, 1H), 3.44 (brs, 1H), 2.70 (ABq, J=18.2, 9.5 Hz, 1H), 2.64-2.56 (m, 1H), 2.15 (br, 1H), 2.06-1.95 (m, 2H), 0.86 (s, 9H), 0.05 (s, 3H), 0.04 (s, 3H).

$^{13}$C NMR (100 MHz, CDCl$_3$) δ103.2, 82.2, 70.8, 63.9, 51.1, 50.8, 48.8, 29.5, 25.7, 17.8, −4.0, −4.7.

Ent-12:

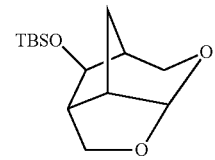

ent-12

Yield: 70%

Ent-13:

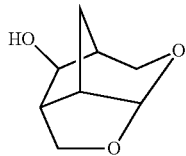

ent-13

Yield: 88%; [α]$_D$=+23.7 (c 0.57, CHCl$_3$)
Ent-14:

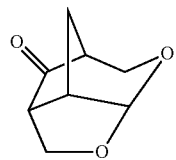

ent-14

Yield: 86%
$^1$H NMR (400 MHz, CDCl$_3$) δ 5.69 (d, J=7.0 Hz, 1H), 4.34 (d, J=8.8 Hz, 1H), 3.94-3.86 (m, 2H), 3.81 (d, J=11.2 Hz, 1H), 3.12-3.05 (m, 1H), 2.66 (t, J=6.7 Hz, 1H), 2.51-2.43 (m, 1H), 2.21 (d, J=12.0 Hz, 1H), 2.00 (dt, J=12.1, 4.4 Hz, 1H).
$^{13}$C NMR (100 MHz, CDCl$_3$) δ 200.8, 104.3, 72.0, 63.4, 49.7, 46.8, 42.9, 23.4
Ent-15:

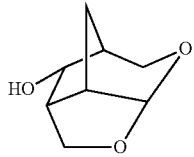

ent-15

Yield: 85%; [α]$_D$=+8.18 (c 0.44, CHCl$_3$)
Compound 16

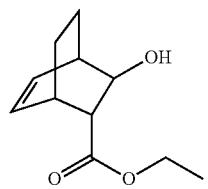

16

To an oven and flame dry two neck round bottom flask, was added a solution of oxazaborolidine 1 (0.68 mmol, 2.72 mL, 0.25 M solution in Toluene). Solvent was removed carefully under reduced pressure and the resulting residue was dissolved in 1 mL absolute CH$_2$Cl$_2$ (distilled over CaH$_2$, degassed and dried over MS 4A). It was cooled to −25° C. and a solution of Tf$_2$NH (0.54 mmol, 0.152 g in 1 mL abs. CH$_2$Cl$_2$) was added. After stirring the resulting reaction mixture for 30 min at −25° C., solvent was removed carefully under reduced pressure at the same temperature. Now a solution of vinyl boronate 8 (2.7 mmol, 0.61 g in 1.5 mL abs. CH$_2$Cl$_2$) was added to the resulting residue. Reaction mixture was cooled to −78° C. and cyclohexadiene (13.5 mmol, 1.28 mL) was added slowly drop wise and then raised the reaction temperature slowly to 23° C. After stirring for further 45 h at 23° C., reaction mixture was diluted with Et$_2$O and then filtered through celite. Filtrate was concentrated under reduced pressure and the resulting residue was purified by silica gel flash column chromatography (hexanes—8% ethyl acetate/hexanes) to obtain corresponding Diels-Alder adduct (contains some minor impurities and has been used in the next step without further purification).

To a mixture of above Diels-Alder adduct and KHCO$_3$ (5.4 mmol, 2.7 mL, 2 M aqueous solution) in THF:EtOH (10 mL, 3:1), H$_2$O$_2$ (10.8 mmol, 1.1 mL, 30% wt solution in H$_2$O) was added slowly at 0° C. The resulting reaction mixture was stirred for 4.5 h at 0° C. and then quenched with aqueous Na$_2$S$_2$O$_3$ solution. Resulting mixture was extracted with ethyl acetate and combined extracts were washed with H$_2$O & brine. Combined organic layers were dried over anhydrous Na$_2$SO$_4$, filtered and solvent was removed under reduced pressure. The resulting residue was purified by silica gel flash column chromatography (20-25% ethyl acetate/hexanes) to obtain compound 16 in 79% yield over two steps (0.42 g).

$^1$H NMR (400 MHz, CDCl$_3$) δ 6.23-6.15 (m, 2H), 4.12 (q, J=7.1 Hz, 2H), 4.02-3.96 (m, 1H), 2.90-2.84 (m, 1H), 2.65-2.57 (m, 1H), 2.26 (dd, J=4.2, 1.9 Hz, 1H), 2.09 (br, 1H), 2.03-1.96 (m, 1H), 1.72-1.61 (m, 1H), 1.36-1.28 (m, 1H), 1.24 (t, J=7.1 Hz, 3H), 1.17-1.08 (m, 1H).
$^{13}$C NMR (100 MHz, CDCl$_3$) δ 174.5, 132.9, 132.0, 71.8, 60.5, 52.3, 37.4, 32.5, 25.6, 16.2, 14.1.
[α]$_D$=−50.37 (c 0.81, CHCl$_3$)
Compound 17

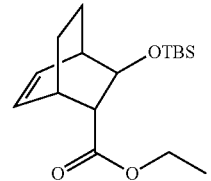

17

Yield: 89%
$^1$H NMR (400 MHz, CDCl$_3$) δ 6.18 (d, J=3.2 Hz, 1H), 6.17 (d, J=3.2 Hz, 1H), 4.10 (qd, J=7.1, 1.9 Hz, 2H), 3.99 (td, J=3.5, 1.5 Hz, 1H), 2.84-2.79 (m, 1H), 2.53-2.47 (m, 1H), 2.24 (dd, J=3.6, 2.1 Hz, 1H), 2.09-2.00 (m, 1H), 1.70-1.61 (m, 1H), 1.34-1.28 (m, 1H), 1.24 (t, J=7.1 Hz, 3H), 1.09-1.00 (m, 1H), 0.88 (s, 9H), 0.05 (s, 3H), 0.03 (s, 3H).
$^{13}$C NMR (100 MHz, CDCl$_3$) δ 174.7, 133.0, 132.1, 72.0, 60.3, 53.1, 38.2, 33.1, 25.8, 25.6, 17.9, 16.5, 14.3, −4.86, −4.9.
Compound 18

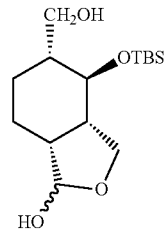

18

Yield: 61% (for 3 steps) (as mixture of diastereomers)

Compound 19

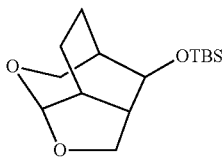

Yield: 25%

¹H NMR (300 MHz, CDCl₃) δ 5.24 (d, J=5.6 Hz, 1H), 4.11-3.98 (m, 2H), 3.76 (d, J=3.3 Hz, 1H), 3.72-3.56 (m, 2H), 2.33-2.24 (m, 1H), 2.22-2.14 (m, 1H), 2.01-1.82 (m, 4H), 1.71-1.58 (m, 1H), 0.88 (s, 9H), 0.04 (s, 3H), 0.03 (s, 3H).

Compound 19a

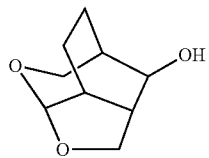

Yield: 70%

¹H NMR (400 MHz, CDCl₃) δ 5.24 (dd, J=5.5, 1.1 Hz, 1H), 4.08-4.02 (m, 2H), 3.89 (s, 1H), 3.71 (d, J=12.3 Hz, 1H), 3.62 (ddd, J=12.3, 6.6, 1.2 Hz, 1H), 2.34-2.26 (m, 1H), 2.25-2.19 (m, 1H), 2.10-2.02 (m, 1H), 2.00-1.81 (m, 4H), 1.78-1.70 (m, 1H).

Compound 20

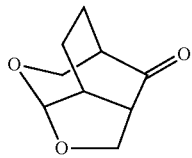

Yield: 87% (reaction time 22 h)

¹H NMR (300 MHz, CDCl₃) δ 5.53 (d, J=6.0 Hz, 1H), 4.29 (d, J=8.8 Hz, 1H), 4.05 (dd, J=8.8, 6.7 Hz, 1H), 3.91 (d, J=12.4 Hz, 1H), 3.69 (dd, J=12.4, 6.0 Hz, 1H), 2.77 (t, J=6.9 Hz, 1H), 2.65-2.56 (m, 1H), 2.56-2.48 (m, 1H), 2.31-2.20 (m, 1H), 2.20-2.08 (m, 1H), 2.07-1.94 (m, 1H), 1.94-1.81 (m, 1H).

Compound 21

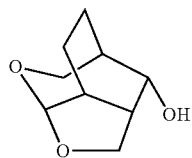

Yield: 79%

¹H NMR (400 MHz, CDCl₃) δ 5.28 (d, J=5.6 Hz, 1H), 4.74 (d, J=8.9 Hz, 1H), 4.05 (d, J=12.3 Hz, 1H), 3.95 (dd, J=8.6, 3.3 Hz, 1H), 3.81 (dd, J=8.9, 6.8 Hz, 1H), 3.45 (dd, J=12.3, 6.2 Hz, 1H), 2.64 (ABq, J=15.4, 7.8 Hz, 1H), 2.46-2.39 (m, 1H), 1.99-1.85 (m, 3H), 1.73-1.59 (m, 3H).

¹³C NMR (100 MHz, CDCl₃) δ 104.8, 69.5, 68.5, 61.0, 43.2, 41.9, 41.2, 22.0, 16.7.

Synthesis of Mixed Carbonates:

Compound 22a

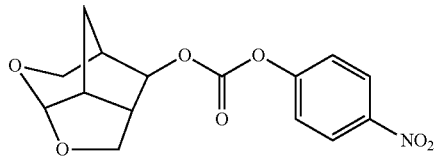

To a solution of alcohol 13 (0.061 mmol, 9.5 mg) in CH₂Cl₂ (2 mL), pyridine (0.183 mmol, 15 μL) and 4-nitrophenyl chloroformate (0.122 mmol, 24.6 mg) were added at 0° C. and the resulting reaction mixture was stirred for 1 h at 23° C. Solvent was removed under reduced pressure and the resulting residue was purified by silica gel flash column chromatography (35% ethyl acetate/hexanes) to obtain corresponding mixed carbonate 22a in 90% yield (17.6 mg).

¹H NMR (400 MHz, CDCl₃) δ 8.28 (d, J=9.2 Hz, 2H), 7.38 (d, J=9.2 Hz, 2H), 5.45 (d, J=6.7 Hz, 1H), 4.78 (s, 1H), 4.28 (d, J=9.4 Hz, 1H), 4.03 (dd, J=9.3, 6.6 Hz, 1H), 3.95 (dd, J=11.7, 8.6 Hz, 1H), 3.66 (d, J=11.7 Hz, 1H), 2.87-2.81 (m, 1H), 2.73 (t, J=6.8 Hz, 1H), 2.49-2.43 (m, 1H), 2.03-1.95 (m, 2H).

¹³C NMR (100 MHz, CDCl₃) δ 155.3, 152.0, 145.4, 125.3, 121.6, 103.8, 92.2, 72.6, 63.8, 49.5, 45.2, 41.2, 25.9.

Compound 22b

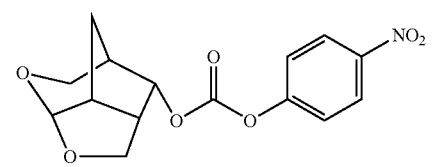

To a solution of alcohol 15 (0.484 mmol, 75.6 mg) in CH₂Cl₂ (4 mL), pyridine (2.2 mmol, 0.18 mL) and 4-nitrophenyl chloroformate (1.45 mmol, 0.292 g) were added at 0° C. and the resulting reaction mixture was stirred for 2 h at 23° C. Solvent was removed under reduced pressure and the resulting residue was purified by silica gel flash column chromatography (20-30% ethyl acetate/hexanes) to obtain respective mixed carbonate 22b in 94% yield (140 mg).

¹H NMR (400 MHz, CDCl₃) δ 8.29 (d, J=9.2 Hz, 2H), 7.39 (d, J=9.2 Hz, 2H), 5.52 (d, J=6.8 Hz, 1H), 5.02 (dd, J=9.2, 5.7 Hz, 1H), 4.28 (d, J=9.5 Hz, 1H), 4.05 (d, J=11.6 Hz, 1H), 3.86 (dd, J=9.4, 6.6 Hz, 1H), 3.74 (dd, J=11.6, 7.9 Hz, 1H), 2.96 (dd, J=15.7, 7.1 Hz, 1H), 2.82-2.75 (m, 1H), 2.62-2.54 (m, 1H), 1.95 (d, J=12.2 Hz, 1H), 1.56 (dt, J=12.2, 4.2 Hz, 1H).

¹³C NMR (100 MHz, CDCl₃) δ 155.3, 152.0, 145.5, 125.3, 121.7, 104.4, 79.7, 68.3, 59.5, 44.9, 41.8, 37.3, 23.5.

Compound Ent-22a

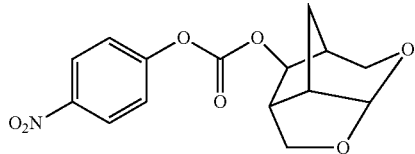

To a solution of ent-13 (0.07 mmol, 10.9 mg) in CH$_2$Cl$_2$ (2 mL), NMM (0.21 mmol, 23 µL) and 4-nitrophenyl chloroformate (0.14 mmol, 28.2 mg) were added at 0° C. and the resulting reaction mixture was stirred for 1 h at 23° C. Solvent was removed under reduced pressure and the resulting residue was purified by silica gel flash column chromatography (25-35% ethyl acetate/hexanes) to obtain mixed carbonate ent-22a in 95% yield (21.3 mg).

Compound Ent-22b

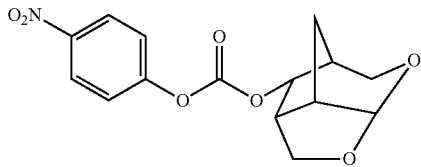

Yield: 83%

Compound 22c

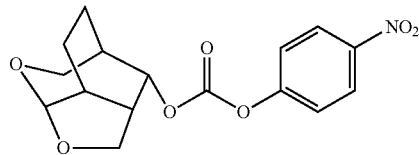

Yield: 93% (reaction time 8 h)
$^1$H NMR (400 MHz, CDCl$_3$) δ 8.30 (d, J=9.2 Hz, 2H), 7.39 (d, J=9.2 Hz, 2H), 5.36 (d, J=5.6 Hz, 1H), 4.90 (ddd, J=8.8, 3.5, 0.8 Hz, 1H), 4.55 (d, J=9.3 Hz, 1H), 4.08 (d, J=12.6 Hz, 1H), 3.93 (dd, J=9.3, 6.6 Hz, 1H), 3.56 (ddd, J=12.6, 6.1, 0.9 Hz, 1H), 2.94 (ABq, J=15.1, 7.8 Hz, 1H), 2.56-2.48 (m, 1H), 2.30-2.23 (m, 1H), 2.09-1.92 (m, 2H), 1.85-1.66 (m, 2H).

Synthesis of Inhibitors:

Inhibitor A:

To a solution of amine 23 (0.059 mmol, 24 mg) and DiPEA (0.24 mmol, 42 µL) in CH$_3$CN (2 mL), mixed carbonate 22a (0.054 mmol, 17.3 mg) was added at 23° C. Resulting reaction mixture was stirred for 5.5 days at 23° C. Solvent was removed under reduced pressure and the resulting residue was purified by silica gel flash column chromatography (30-50% ethyl acetate/hexanes) to obtain inhibitor A in 83% yield (26.3 mg).

$^1$H NMR (400 MHz, CDCl$_3$) δ 7.70 (d, J=8.6 Hz, 2H), 7.32-7.26 (m, 2H), 7.24-7.19 (m, 3H), 6.97 (d, J=8.8 Hz, 2H), 5.38 (d, J=6.6 Hz, 1H), 4.88 (d, J=8.1 Hz, 1H), 4.51 (s, 1H), 4.19 (d, J=9.0 Hz, 1H), 3.99-3.92 (m, 1H), 3.87 (s, 3H), 3.85-3.75 (m, 4H), 3.55 (d, J=11.5 Hz, 1H), 3.12 (dd, J=15.1, 8.2 Hz, 1H), 3.05-2.92 (m, 3H), 2.90-2.82 (m, 1H), 2.78 (dd, J=13.4, 6.7 Hz, 1H), 2.73-2.65 (m, 1H), 2.46 (t, J=6.0 Hz, 1H), 2.02 (brs, 1H), 1.87-1.78 (m, 2H), 1.76-1.68 (m, 1H), 0.91 (d, J=6.6 Hz, 3H), 0.86 (d, J=6.5 Hz, 3H).

$^{13}$C NMR (100 MHz, CDCl$_3$) δ 163.0, 155.9, 137.6, 129.7, 129.4, 128.4, 126.5, 114.3, 103.8, 87.8, 72.9, 72.6, 64.2, 58.7, 55.6, 54.9, 53.7, 49.3, 45.1, 41.1, 35.4, 27.2, 25.7, 20.1, 19.8.

Inhibitor B:

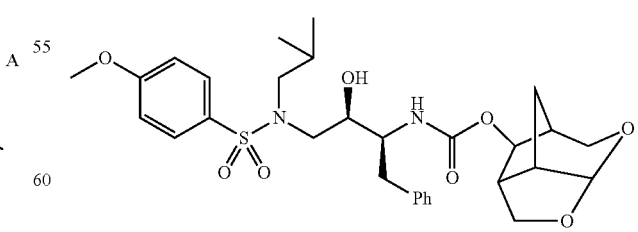

$^1$H NMR (500 MHz, CDCl$_3$) δ 7.74 (d, J=8.6 Hz, 2H), 7.37-7.30 (m, 2H), 7.29-7.21 (m, 3H), 7.01 (d, J=8.6 Hz, 2H), 5.45 (d, J=6.5 Hz, 1H), 5.16 (d, J=8.1 Hz, 1H), 4.82 (dd, J=8.5, 5.9 Hz, 1H), 3.99-3.86 (m, 6H), 3.77 (d, J=9.2 Hz, 1H), 3.66-3.54 (m, 2H), 3.17 (dd, J=14.8, 8.2 Hz, 1H), 3.12-2.95 (m, 3H), 2.92-2.79 (m, 2H), 2.78-2.64 (m, 2H), 2.36 (brs, 1H), 1.93-1.80 (m, 2H), 1.52-1.43 (m, 1H), 0.95 (d, J=6.5 Hz, 3H), 0.90 (d, J=6.5 Hz, 3H).

$^{13}$C NMR (125 MHz, CDCl$_3$) δ 163.1, 155.7, 137.6, 129.8, 129.5, 129.4, 128.6, 126.6, 114.4, 104.3, 75.0, 72.7, 68.4, 59.8, 58.8, 55.6, 55.1, 53.7, 44.8, 41.9, 37.4, 35.4, 27.3, 23.5, 20.1, 19.9.

Inhibitor C:

$^1$H NMR (400 MHz, CDCl$_3$) δ 7.70 (d, J=8.8 Hz, 2H), 7.33-7.26 (m, 2H), 7.25-7.19 (m, 3H), 6.97 (d, J=8.9 Hz, 2H), 5.38 (d, J=6.8 Hz, 1H), 4.83 (d, J=7.8 Hz, 1H), 4.50 (s, 1H), 4.16 (d, J=9.2 Hz, 1H), 3.91 (dd, J=8.8, 2.0 Hz, 1H), 3.87 (s, 3H), 3.86-3.80 (m, 4H), 3.57 (d, J=11.5 Hz, 1H), 3.11 (dd, J=15.1, 8.3 Hz, 1H), 3.06-2.92 (m, 3H), 2.90-2.82 (m, 1H), 2.79 (dd, J=13.4, 6.7 Hz, 1H), 2.69-2.61 (m, 1H), 2.24-2.13 (m, 2H), 1.90-1.73 (m, 3H), 0.91 (d, J=6.6 Hz, 3H), 0.86 (d, J=6.6 Hz, 3H).

$^{13}$C NMR (100 MHz, CDCl$_3$) δ 163.0, 156.0, 137.6, 129.7, 129.5, 129.4, 128.4, 126.4, 114.3, 103.8, 87.9, 72.9, 72.7, 64.3, 58.8, 55.6, 55.0, 53.7, 49.4, 45.0, 41.1, 35.5, 27.2, 25.8, 20.1, 19.9.

Inhibitor D:

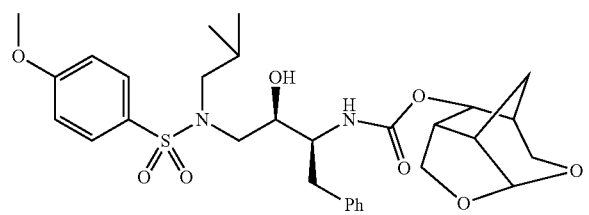

D

$^1$H NMR (400 MHz, CDCl$_3$) δ 7.71 (d, J=8.9 Hz, 2H), 7.33-7.26 (m, 2H), 7.24-7.17 (m, 3H), 6.98 (d, J=8.9 Hz, 2H), 5.43 (d, J=6.7 Hz, 1H), 5.13 (d, J=8.5 Hz, 1H), 4.78 (dd, J=9.1, 5.7 Hz, 1H), 4.10 (d, J=7.2 Hz, 1H), 3.91-3.82 (m, 5H), 3.79 (d, J=11.4 Hz, 1H), 3.68 (dd, J=8.5, 7.1 Hz, 1H), 3.54 (dd, J=11.4, 7.9 Hz, 1H), 3.13 (dd, J=15.0, 8.4 Hz, 1H), 3.07-2.92 (m, 3H), 2.89-2.71 (m, 3H), 2.69-2.61 (m, 1H), 2.28-2.18 (m, 1H), 1.90-1.75 (m, 2H), 1.43 (dt, J=12.1, 4.1 Hz, 1H), 0.91 (d, J=6.6 Hz, 3H), 0.88 (d, J=6.6 Hz, 3H).

$^{13}$C NMR (100 MHz, CDCl$_3$) δ 163.0, 155.6, 137.6, 129.8, 129.4, 129.38, 128.4, 126.5, 114.3, 104.3, 74.8, 72.6, 68.5, 59.8, 58.7, 55.6, 55.1, 53.7, 44.8, 41.8, 37.3, 35.5, 27.2, 23.5, 20.1, 19.8.

Inhibitor E:

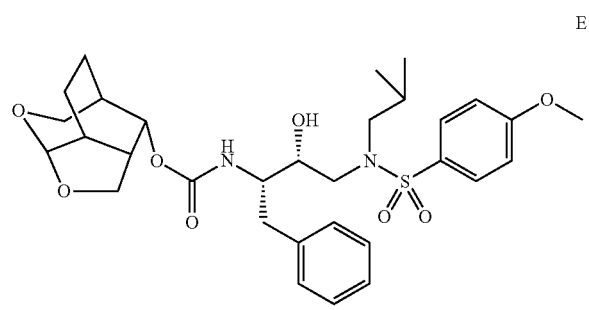 [SMILES: COc1ccc(S(=O)(=O)N(CC(C)C)C[C@@H](O)[C@H](Cc2ccccc2)NC(=O)OC2C3CCC4C(OC3)OCC42)cc1]

E

$^1$H NMR (400 MHz, CDCl$_3$) δ 7.71 (d, J=8.8 Hz, 2H), 7.35-7.26 (m, 2H), 7.23 (d, J=7.1 Hz, 3H), 6.98 (d, J=8.7 Hz, 2H), 5.25 (d, J=5.6 Hz, 1H), 4.97 (d, J=8.2 Hz, 1H), 4.61 (dd, J=8.4, 2.4 Hz, 1H), 3.98 (d, J=9.1 Hz, 1H), 3.91 (d, J=9.8 Hz, 1H), 3.87 (s, 3H), 3.86-3.76 (m, 2H), 3.56 (dd, J=8.9, 6.8 Hz, 1H), 3.41 (dd, J=12.2, 5.9 Hz, 1H), 3.15 (dd, J=15.1, 8.3 Hz, 1H), 3.10-2.92 (m, 3H), 2.87-2.76 (m, 2H), 2.66 (ABq, J=15.0, 7.5 Hz, 1H), 2.40-2.32 (m, 1H), 2.00-1.93 (m, 1H), 1.93-1.77 (m, 3H), 1.73-1.56 (m, 3H), 0.92 (d, J=6.5 Hz, 3H), 0.87 (d, J=6.5 Hz, 3H).

$^{13}$C NMR (100 MHz, CDCl$_3$) δ 163.0, 155.5, 137.6, 129.8, 129.5, 129.4, 128.5, 126.6, 114.3, 104.7, 72.8, 72.1, 70.0, 61.8, 58.8, 55.6, 55.1, 53.7, 43.3, 39.8, 38.7, 35.5, 27.3, 21.7, 20.1, 19.9, 16.5.

Inhibitor F:

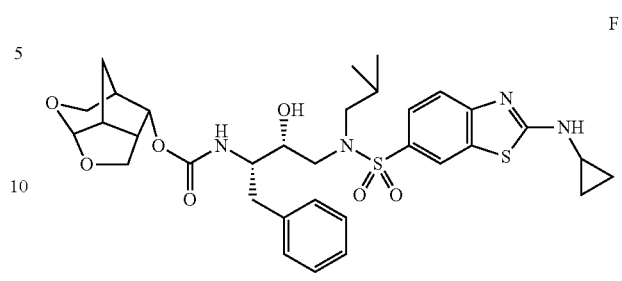

F

$^1$H NMR (400 MHz, CDCl$_3$) δ 8.07 (s, 1H), 7.68 (dd, J=8.6, 1.4 Hz, 1H), 7.65-7.60 (br, 1H), 7.54 (d, J=8.6 Hz, 1H), 7.33-7.25 (m, 2H), 7.25-7.15 (m, 3H), 5.40 (d, J=6.6 Hz, 1H), 5.33 (d, J=8.9 Hz, 1H), 4.78 (dd, J=8.6, 5.8 Hz, 1H), 3.97-3.81 (m, 3H), 3.72 (d, J=9.3 Hz, 1H), 3.62-3.48 (m, 2H), 3.19 (dd, J=14.8, 8.3 Hz, 1H), 3.11-2.94 (m, 3H), 2.89-2.78 (m, 2H), 2.78-2.72 (m, 1H), 2.72-2.60 (m, 2H), 2.35-2.25 (m, 1H), 1.90-1.82 (m, 1H), 1.79 (d, J=12.2 Hz, 1H), 1.46-1.37 (m, 1H), 0.97-0.89 (m, 5H), 0.87 (d, J=6.6 Hz, 3H), 0.81-0.76 (m, 2H).

$^{13}$C NMR (100 MHz, CDCl$_3$) δ 173.2, 155.7, 155.5, 137.7, 131.1, 130.3, 129.3, 128.5, 126.6, 125.4, 120.9, 118.4, 104.3, 75.0, 72.7, 68.4, 59.8, 58.7, 55.2, 53.6, 44.8, 41.9, 37.3, 35.4, 27.3, 26.6, 23.5, 20.1, 19.9, 7.9.

Inhibitor G:

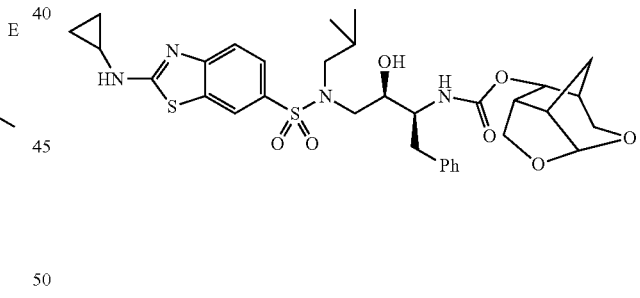

G

$^1$H NMR (400 MHz, CDCl$_3$) δ 8.08 (s, 1H), 7.68 (dd, J=8.3, 1.4 Hz, 1H), 7.57 (d, J=8.5 Hz, 1H), 7.33-7.25 (m, 2H), 7.25-7.16 (m, 3H), 7.08 (br, 1H), 5.43 (d, J=6.7 Hz, 1H), 5.15 (d, J=8.5 Hz, 1H), 4.79 (dd, J=9.1, 5.6 Hz, 1H), 4.10 (d, J=8.8 Hz, 1H), 3.94-3.82 (m, 3H), 3.78 (d, J=11.4 Hz, 1H), 3.69 (dd, J=8.7, 6.8 Hz, 1H), 3.53 (dd, J=11.2, 7.9 Hz, 1H), 3.18 (dd, J=15.0, 8.5 Hz, 1H), 3.09-2.96 (m, 3H), 2.91-2.71 (m, 4H), 2.68-2.61 (m, 1H), 2.28-2.21 (m, 1H), 1.91-1.82 (m, 1H), 1.80 (d, J=12.0 Hz, 1H), 1.43 (dt, J=12.0, 4.0 Hz, 1H), 0.98-0.90 (m, 5H), 0.88 (d, J=6.6 Hz, 3H), 0.82-0.77 (m, 2H).

$^{13}$C NMR (100 MHz, CDCl$_3$) δ 172.9, 155.7, 137.6, 130.5, 129.4, 128.5, 126.6, 125.4, 120.9, 118.6, 104.3, 74.9, 72.6, 68.5, 59.8, 58.9, 55.2, 53.8, 44.8, 41.9, 37.3, 35.5, 27.3, 26.7, 23.5, 20.1, 19.9, 8.0.

Inhibitor H:

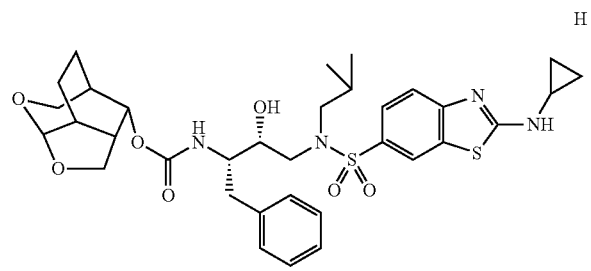 [SMILES: CC(C)CN(C[C@@H](O)[C@H](Cc1ccccc1)NC(=O)OC1C2CCC3C(OC2)OCC31)S(=O)(=O)c1ccc2nc(NC3CC3)sc2c1]

$^1$H NMR (400 MHz, CDCl$_3$) δ 8.08 (s, 1H), 7.68 (dd, J=8.5, 1.8 Hz, 1H), 7.56 (d, J=8.5 Hz, 1H), 7.33-7.26 (m, 2H), 7.23 (d, J=7.4 Hz, 3H), 7.15 (brs, 1H), 5.24 (d, J=5.6 Hz, 1H), 5.06 (d, J=8.6 Hz, 1H), 4.61 (dd, J=8.6, 2.9 Hz, 1H), 3.98 (d, J=9.3 Hz, 1H), 3.93-3.79 (m, 4H), 3.56 (dd, J=8.9, 6.8 Hz, 1H), 3.41 (dd, J=12.2, 5.9 Hz, 1H), 3.19 (dd, J=15.0, 8.2 Hz, 1H), 3.12-2.96 (m, 3H), 2.89-2.79 (m, 2H), 2.79-2.72 (m, 1H), 2.66 (ABq, J=15.1, 7.7 Hz, 1H), 2.39-2.31 (m, 1H), 1.98-1.93 (m, 1H), 1.92-1.80 (m, 3H), 1.72-1.57 (m, 2H), 0.99-0.91 (m, 5H), 0.88 (d, J=6.6 Hz, 3H), 0.82-0.77 (m, 2H).

$^{13}$C NMR (100 MHz, CDCl$_3$) δ 172.9, 155.6, 155.5, 137.6, 131.2, 130.4, 129.4, 128.5, 126.6, 125.4, 120.9, 118.6, 104.7, 72.8, 72.1, 70.0, 61.8, 58.8, 55.1, 53.7, 43.3, 39.8, 38.7, 35.5, 27.3, 26.7, 21.7, 20.1, 19.9, 16.5, 8.0.

Inhibitor I:

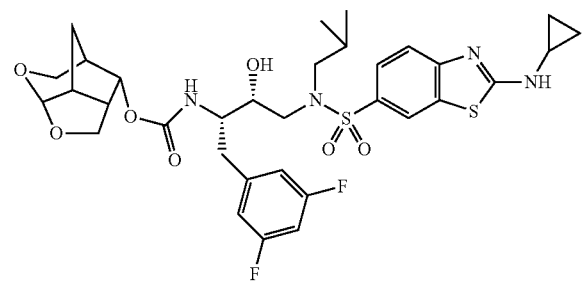

H$^1$-NMR, 400 MHz: 8.09 (s, 1H), 7.69 (d, 1H, J=8.4 Hz), 7.51-7.61 (m, 2H [it contain 1H, multiplet and 1H doublet at 7.55 {d, 1H, J=8.4 Hz}]), 6.77 (d, 2H, J=6.4 Hz), 6.61-6.70 (m, 1H), 5.48 (d, 1H, J=9.2 Hz), 5.42 (d, 1H, J=6.8 Hz), 4.83 (dd, 1H, J=8.8 Hz, 5.6 Hz), 3.96-4.06 (m, 1H), 3.91-3.96 (m, 1H), 3.80-3.91 (m, 3H), 3.54-3.66 (m, 2H), 3.07-3.18 (m, 2H), 3.03-3.07 (m, 1H), 2.96-3.02 (m, 1H), 2.80-2.91 (m, 2H), 2.70-2.80 (m, 2H), 2.62-2.69 (m, 1H), 2.29-2.37 (m, 1H), 1.78-1.90 (m, 2H), 1.44 (dt, 1H, J=12.0 Hz, 3.6 Hz), 0.92 (d, 6H, J=6.8 Hz), 0.86-0.91 (m, 2H), 0.77-0.82 (m, 2H).

Inhibitor J:

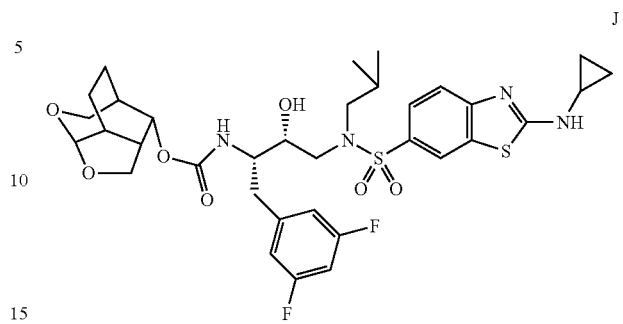

H$^1$-NMR, 400 MHz: 8.09 (s, 1H), 7.70 (d, 1H, J=8.0 Hz), 7.57 (d, 1H, J=8.0 Hz), 6.96-7.06 (b s, 1H), 6.78 (d, 2H, J=6.0 Hz), 6.62-6.70 (m, 1H), 5.26 (d, 1H, J=5.6 Hz), 5.15 (d, 1H, J=9.2 Hz), 4.66 (dd, 1H, J=8.8 Hz, 2.8 Hz), 4.12-4.15 (m, 1H), 3.80-3.97 (m, 3H), 3.66 (dd, 1H, J=8.8 Hz, 6.0 Hz), 3.41 (q, 1H, J=6.0 Hz), 3.11-3.18 (m, 1H), 3.08 (d, 1H, J=3.2 Hz), 3.02-3.07 (m, 1H), 2.96-3.02 (m, 1H), 2.80-2.91 (m, 2H), 2.74-2.80 (m, 1H), 2.70 (q, 1H, J=7.6 Hz), 2.35-2.43 (m, 1H), 1.94-2.01 (m, 1H), 1.78-1.94 (m, 3H), 1.58-1.76 (m, 3H), 0.93 (d, 6H, J=6.8 Hz), 0.86-0.91 (m, 2H), 0.78-0.82 (m, 2H).

The present invention provides for the following exemplary embodiments, the numbering of which is not to be construed as designating levels of importance:

Embodiment 1 relates to a compound of the formula (I):

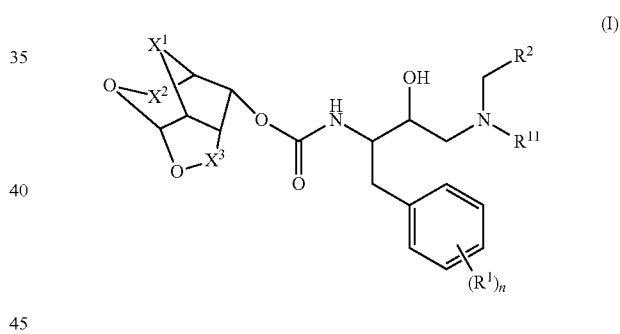

(I)

or a pharmaceutically acceptable salt, polymorph, prodrug, solvate or clathrate thereof, wherein: X$^1$ is alkylene, —O—, —CH$_2$NR$^4$— or —NHR$^4$—; X$^2$ and X$^3$ are each, independently alkylene; n is an integer from 0 to 3; R$^1$ is alkoxy, hydroxyalkyl, halo or heterocyclylalkyloxy; R$^2$ is alkyl, haloalkyl, aryl, arylalkyl, cycloalkylalkyl, heterocyclylcarbonyl, heterocyclyl, heterocyclylalkyl or —C(R$^7$R$^8$)-alkylene-R$^9$; R$^{11}$ is —SO$_2$R$^3$, —N(R$^{12}$)SO$_2$R$^3$, —N(R$^{12}$)C(O)R$^3$, —N(R$^{12}$)C(O)CH(R$^{12}$)N(R$^{12}$)C(O)R$^{13}$, —C(O)N(R$^{12}$)$_2$, —C(O)-alkylene-X$^4$—R$^{10}$ (wherein X$^4$ is S, O or NR$^6$, wherein R$^6$ is H, alkyl, cycloalkyl or alkylaryl) or —C(O)R$^{10}$; R$^3$ is aryl or heteroaryl; R$^4$ is alkyl, aryl or heteroaryl; R$^7$ and R$^8$ are each, independently hydrogen, alkyl, aryl, arylalky, heteroaryl, heteroarylalkyl or, R$^7$ and R$^8$, together with the carbon atom to which they are attached, form a cycloalkyl or a heterocyclyl group; R$^9$ is hydrogen, OR$^{10}$, OC(O)N(R$^{10}$)$_2$, CN, NO$_2$, CF$_3$, OCF$_3$, N(R$^{10}$)$_2$, SR$^{10}$, SOR$^{10}$, SO$_2$R$^{10}$, SO$_2$N(R$^{10}$)$_2$, SO$_3$R, C(O)R$^{10}$, C(O)OR$^{10}$, OC(O)R$^{10}$, C(O)N(R$^{10}$)$_2$, (CH$_2$)$_{0-2}$N(R$^{10}$)C(O)R$^{10}$ or (CH$_2$)$_{0-2}$N(R$^{10}$)C(O)OR$^{10}$; R$^{10}$ is hydrogen, alkyl, acyl, cycloalkyl, aryl, aralkyl, heterocyclyl, heteroaryl, or heteroarylalkyl; $R^{12}$ is hydrogen, alkyl, alkylaryl, heterocyclyl or the two $R^{12}$ groups on an $N(R^{12})_2$, together with the nitrogen atom to which they are attached, form a heterocyclyl group; and $R^{13}$ is hydrogen, alkyl, $-N(R^{12})_2$ or $-OR^{12}$; or $R^2$ and $R^{11}$, together with the $-CH_2N-$ that connects them, form a heterocyclyl or substituted heterocyclyl group.

Embodiment 2 relates to a compound of Embodiment 1 having the formula (II):

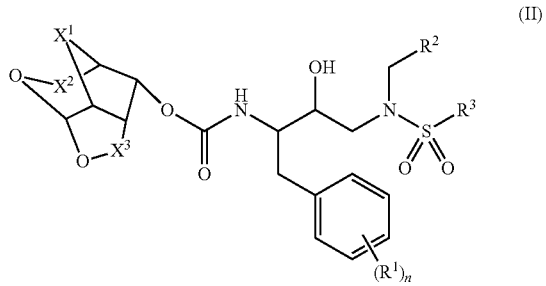

(II)

or a pharmaceutically acceptable salt, polymorph, prodrug, solvate or clathrate thereof, wherein: n is an integer from 1 to 3; $R^1$ is alkoxy, hydroxyalkyl, halo or heterocyclylalkyloxy; $R^2$ is alkyl, haloalkyl, arylalkyl, cycloalkylalkyl, heterocyclylcarbonyl or heterocyclylalkyl; $R^3$ is substituted aryl or substituted heteroaryl; $X^1$ is alkylene, $-O-$, $-CH_2NR^4-$ or $-NHR^4-$, wherein $R^4$ is alkyl, aryl or heteroaryl; and $X^2$ and $X^3$ are each, independently alkylene.

Embodiment 3 relates to the compound of Embodiments 1-2, wherein $X^1$ is alkylene.

Embodiment 4 relates to the compound of Embodiments 1-3, wherein the alkylene is $C_1$-$C_4$ alkylene.

Embodiment 5 relates to the compound of Embodiments 1-4, wherein $X^2$ is $C_1$-$C_4$ alkylene.

Embodiment 6 relates to the compound of Embodiments 1-5, wherein $X^3$ is $C_1$-$C_4$ alkylene.

Embodiment 7 relates to the compound of Embodiments 1-6, wherein $R^1$ is $C_1$-$C_6$ alkoxy, hydroxy-$C_1$-$C_6$-alkyl, halo or $C_3$-$C_6$-heterocyclyl-$C_1$-$C_6$-alkyloxy.

Embodiment 8 relates to the compound of Embodiments 1-7, wherein $R^2$ is $C_1$-$C_6$ alkyl, halo-$C_1$-$C_6$-alkyl, $C_6$-$C_{10}$-aryl-$C_1$-$C_6$-alkyl, $C_3$-$C_6$-cycloalkyl-$C_1$-$C_6$-alkyl, $C_3$-$C_6$-heterocyclylcarbonyl or $C_3$-$C_6$-heterocyclyl-$C_1$-$C_6$-alkyl.

Embodiment 9 relates to the compound of Embodiments 1-8, wherein $R^3$ is substituted $C_6$-$C_{10}$ aryl.

Embodiment 10 relates to the compound of Embodiment 9, wherein $R^3$ is substituted phenyl.

Embodiment 12 relates to the compound of Embodiment 9, wherein the substituted phenyl is phenyl substituted with at least one of amino, $C_1$-$C_6$ alkoxy, hydroxy-$C_1$-$C_6$-alkyl and halo.

Embodiment 13 relates to the compound of Embodiment 9, wherein the substituted phenyl is a group having the formula:

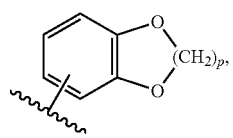

wherein p is an integer from 1 to 2.

Embodiment 14 relates to the compound of Embodiments 1-8, wherein $R^3$ is substituted $C_6$-$C_8$ heteroaryl.

Embodiment 15 relates to the compound of Embodiment 14, wherein the substituents on the $C_6$-$C_8$ heteroaryl are alkyl, $C_1$-$C_6$ alkyl-O$-$, $C_6$-$C_{10}$ aryl-O$-$, or halo.

Embodiment 16 relates to the compound of Embodiment 14, wherein the substituted $C_6$-$C_8$ heteroaryl is a group having the formula:

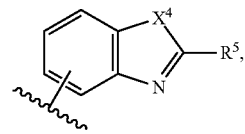

wherein $R^5$ is $C_1$-$C_6$ alkylamino, $C_3$-$C_6$ cycloalkyl-$C_3$-$C_6$ heterocycloamino;

and $X^2$ is S, O or $NR^6$, wherein $R^6$ is H, alklyl, cycloalkyl or alkylaryl.

Embodiment 17 relates to the compound of Embodiment 2, wherein the compound of the formula (II) is a compound of the formula (IIa) or (IIb):

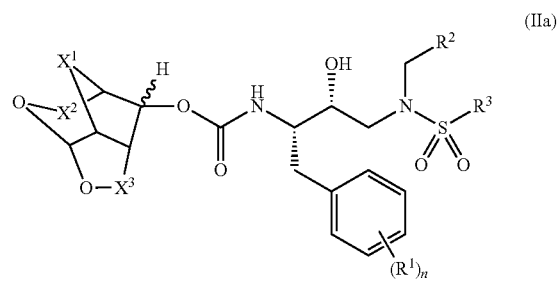

(IIa)

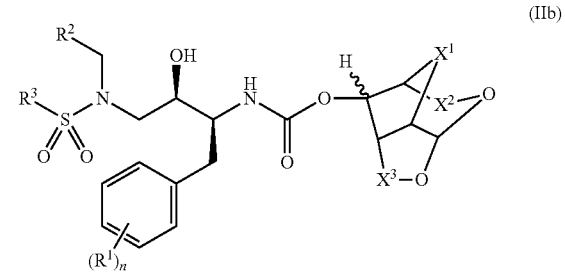

(IIb)

or a pharmaceutically acceptable salt, polymorph, prodrug, solvate or clathrate thereof.

Embodiment 18 relates to the compound of Embodiments 1-17 which is:
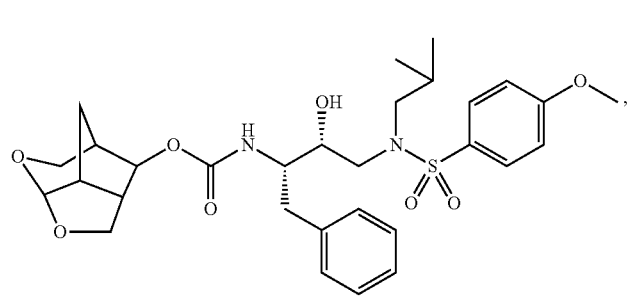
A
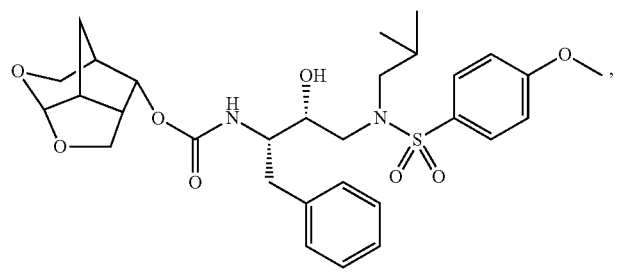
B
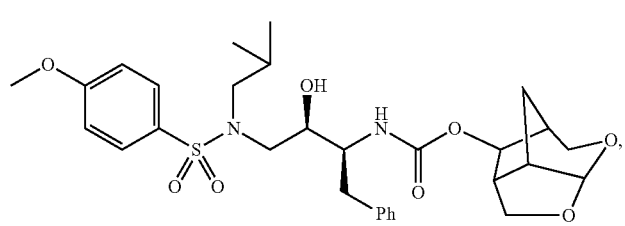
C
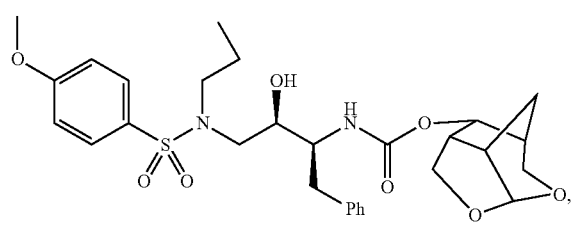
D
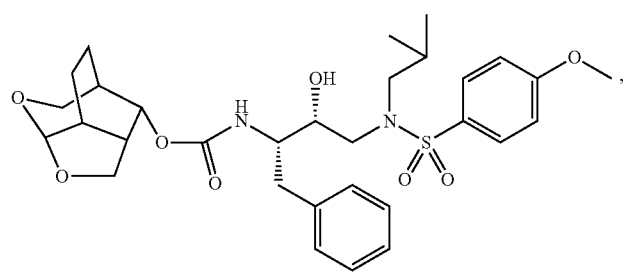
E
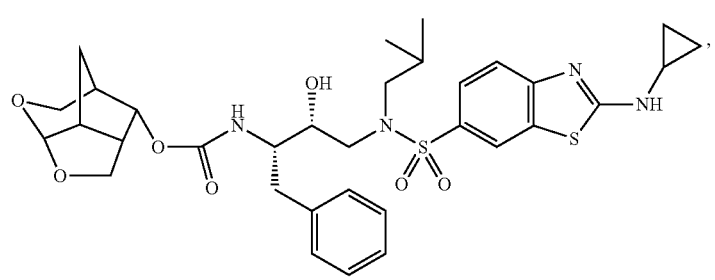
F -continued
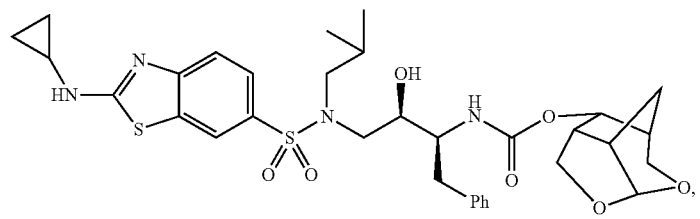
G
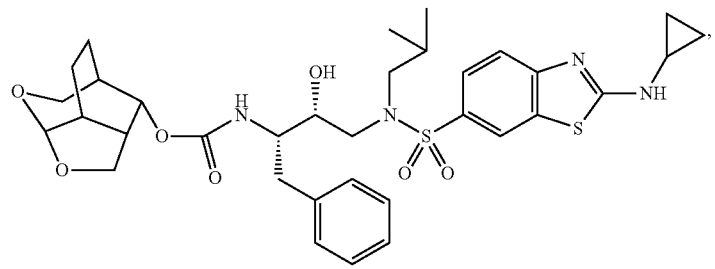
H
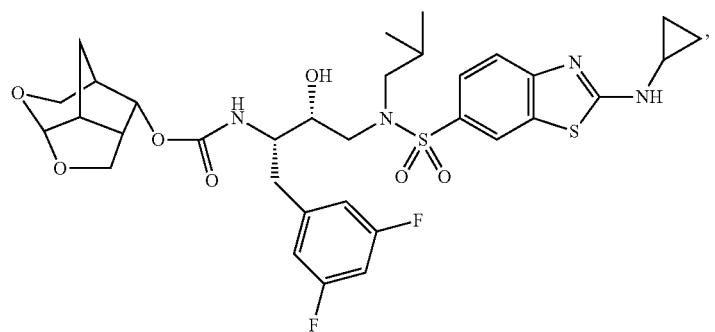
I
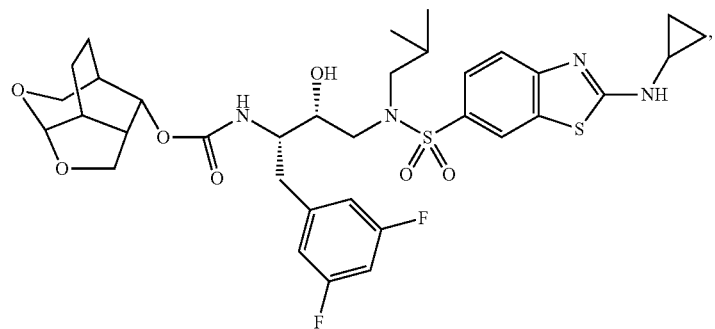
J
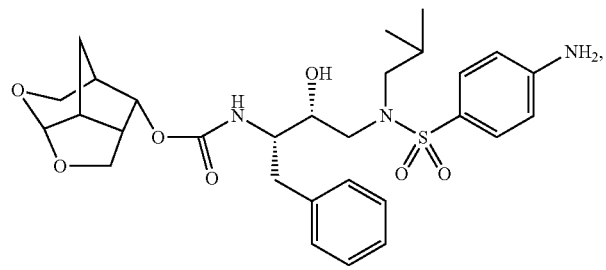
K

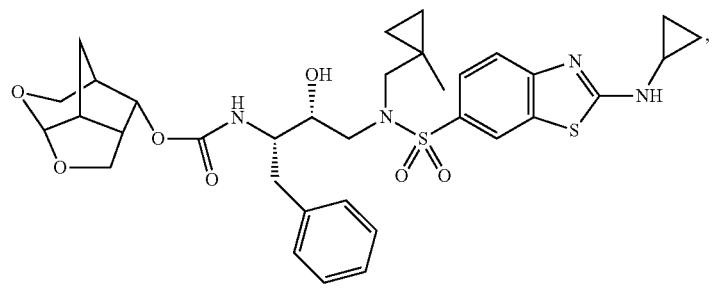
L
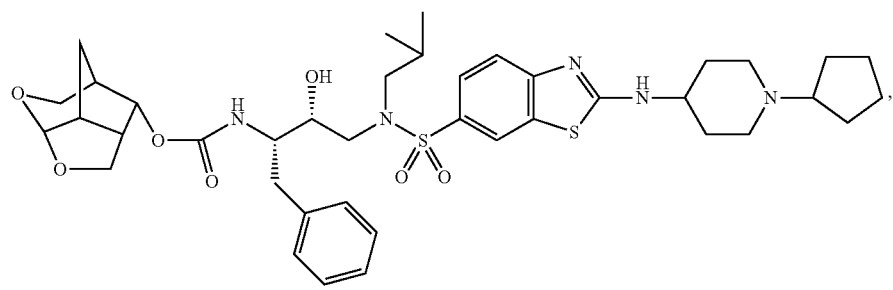
M
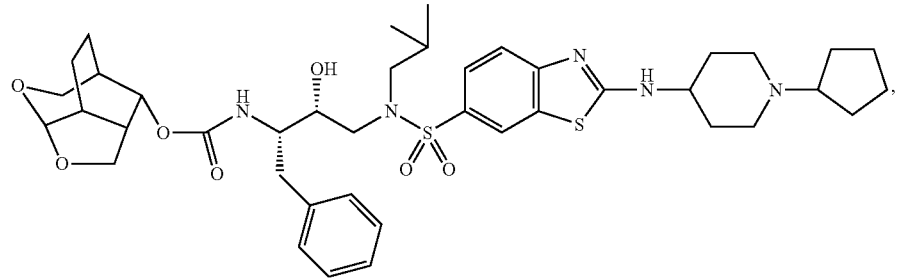
N
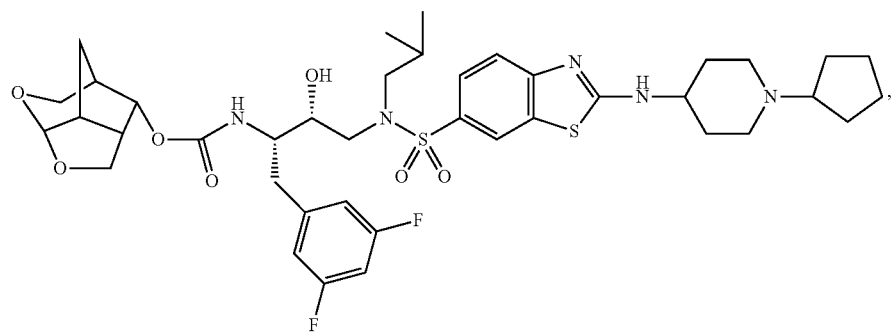
O
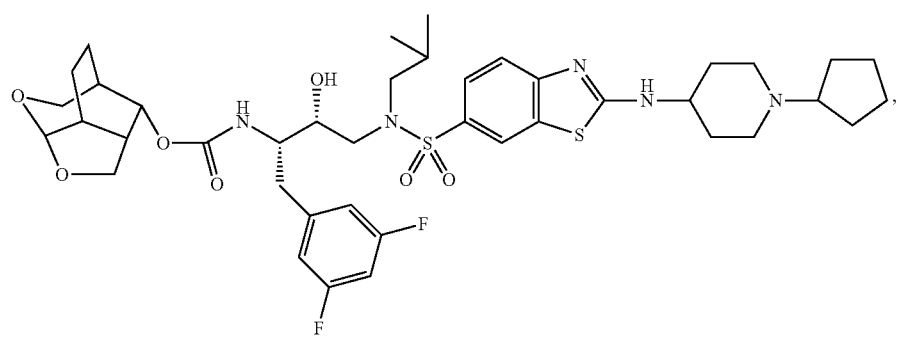
P

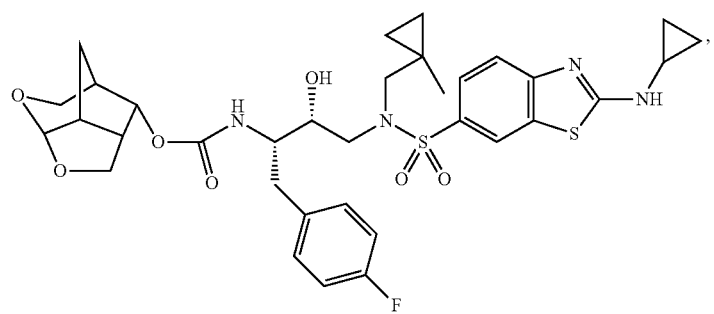
Q
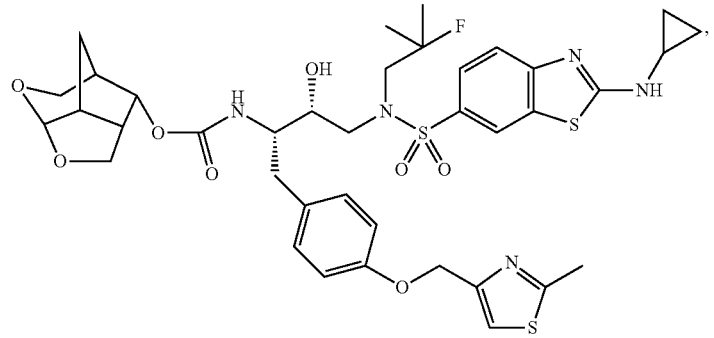
R
S
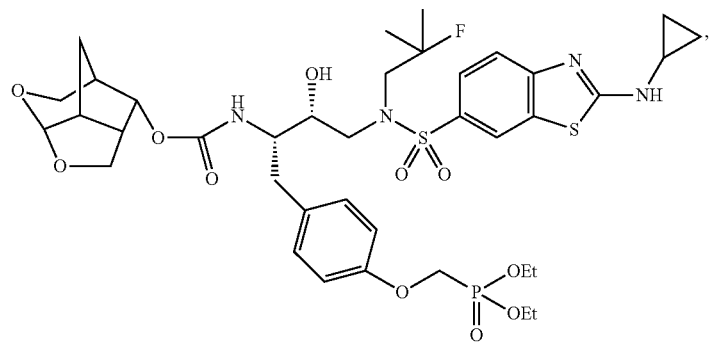
T
U

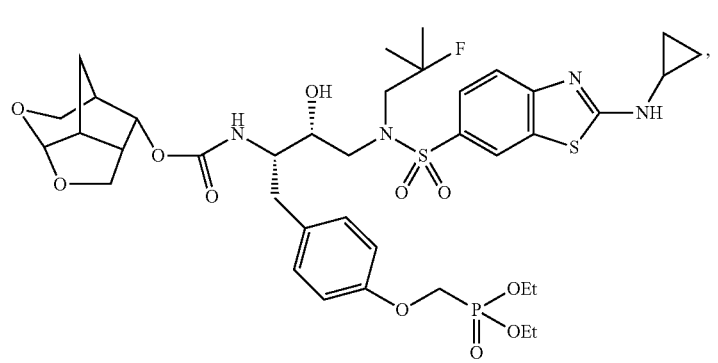
V
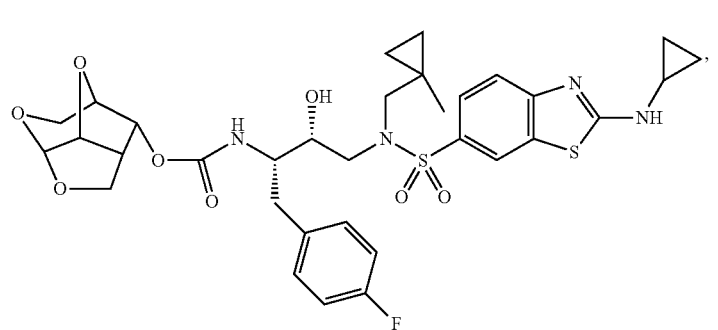
W
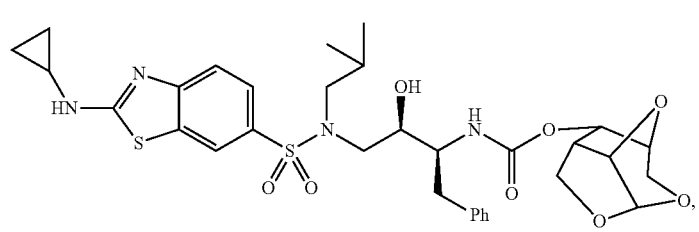
X
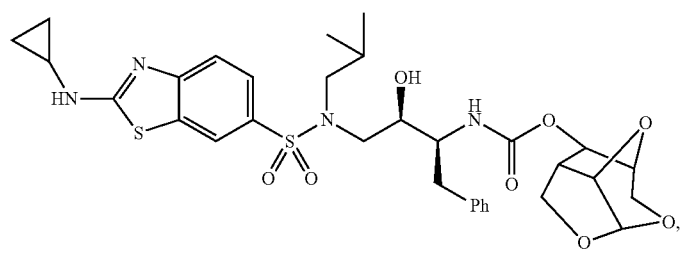
Y
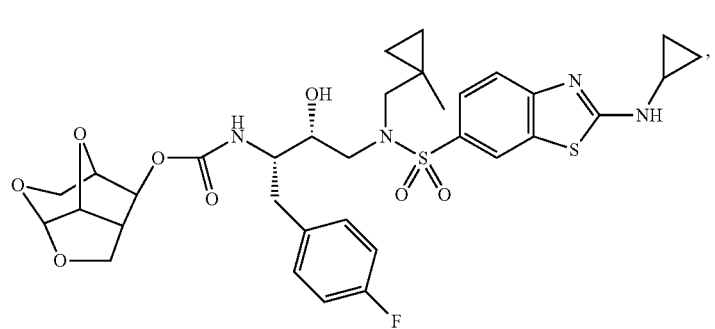
Z

-continued
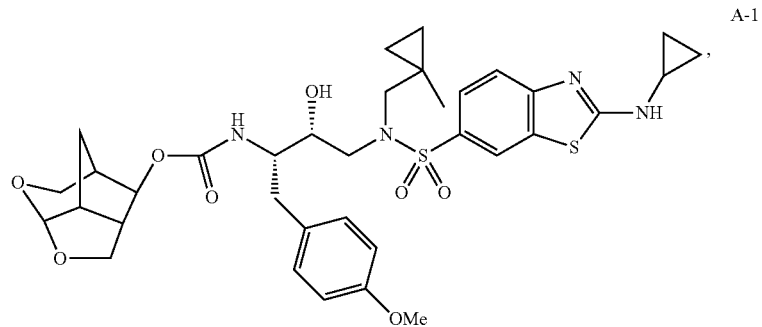
A-1
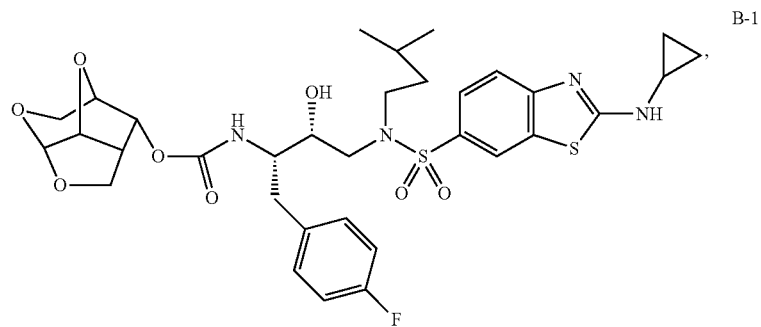
B-1
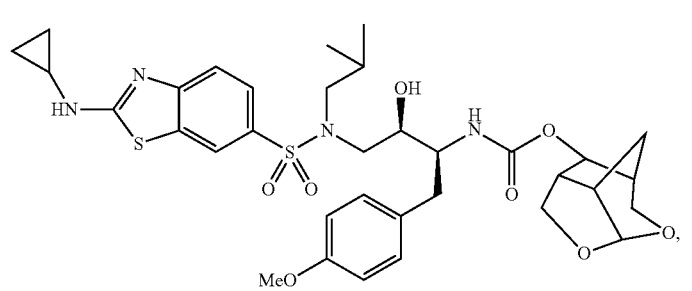
C-1
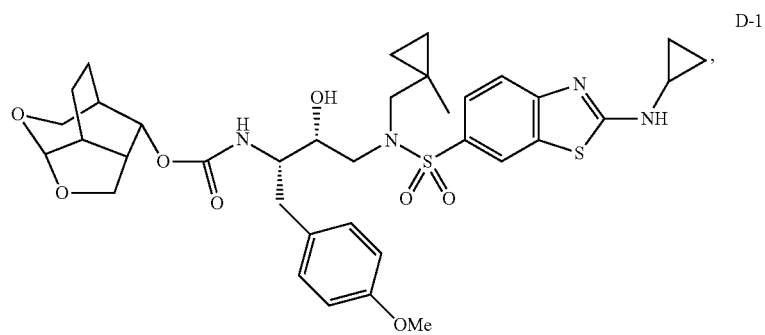
D-1
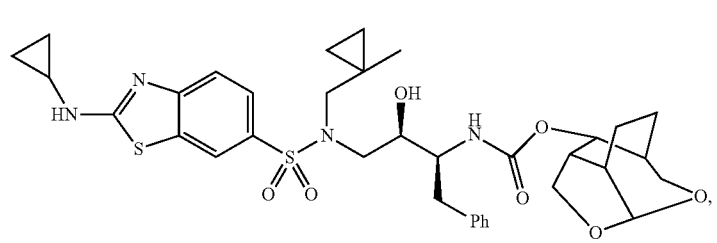
E-1

-continued
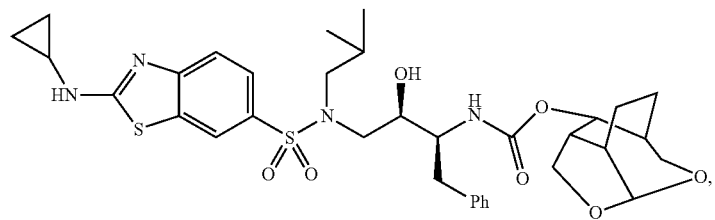
F-1
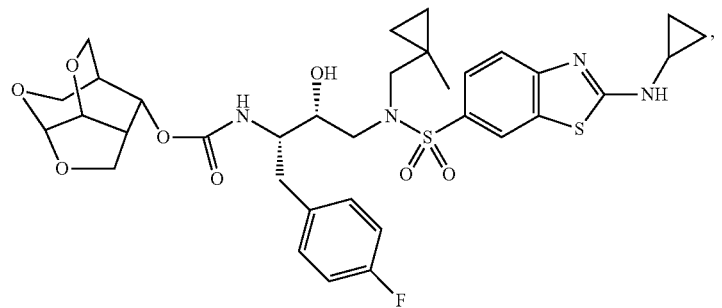
G-1
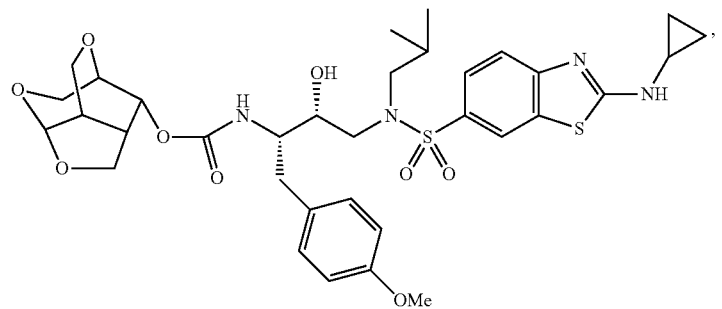
H-1
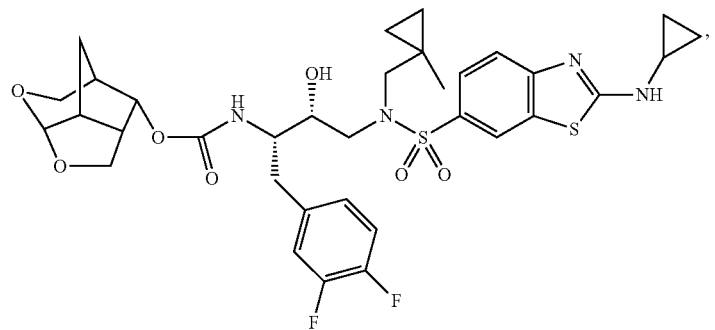
I-1
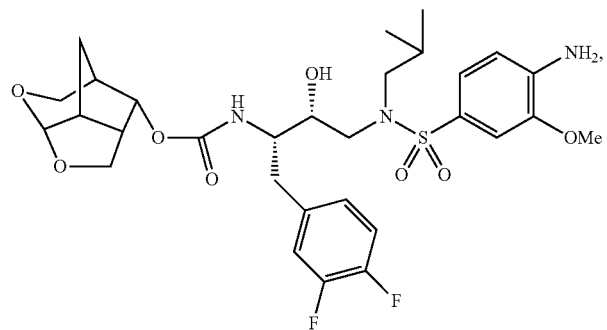
J-1

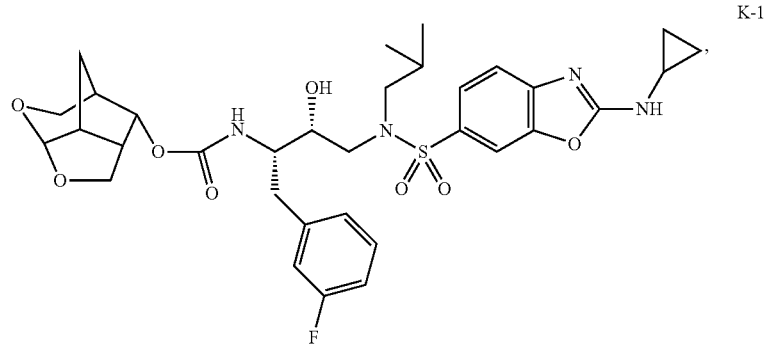
K-1
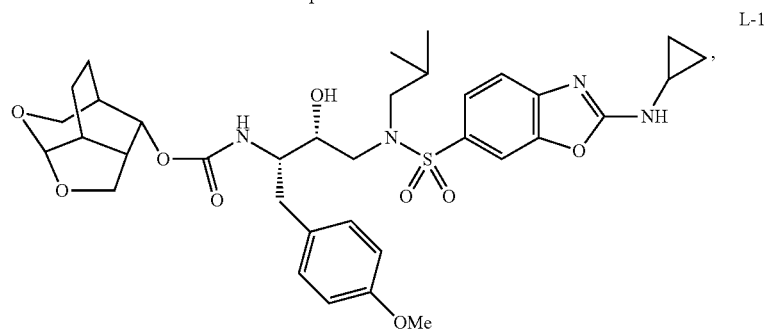
L-1
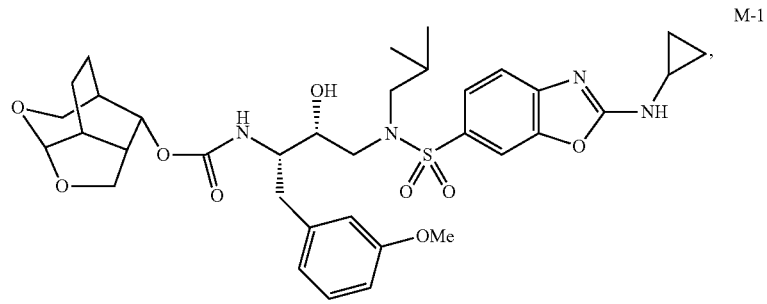
M-1
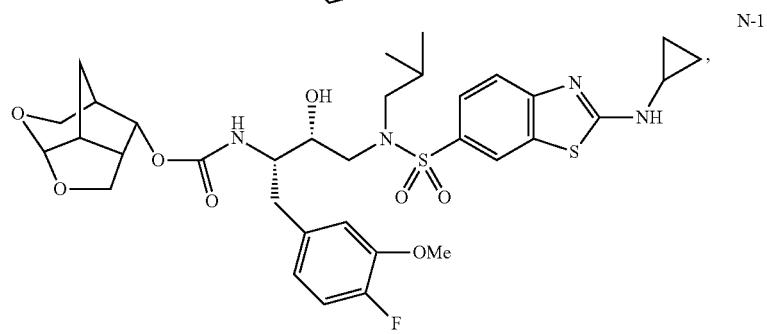
N-1
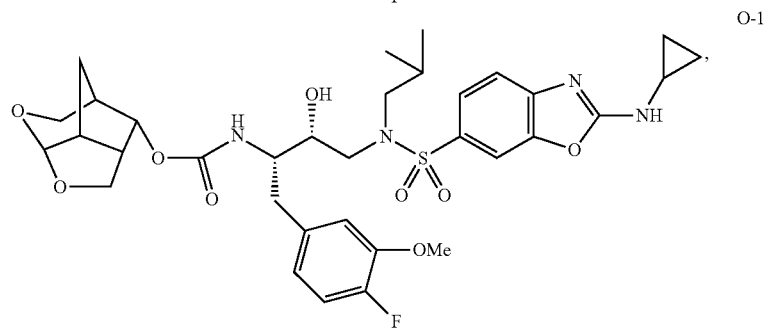
O-1
or a pharmaceutically acceptable salt, polymorph, prodrug, solvate or clathrate thereof.

Embodiment 19 relates to the compound of Embodiment 1, wherein $R^2$ is aryl, a heterocyclyl group or —C($R^7R^8$)-alkylene-$R^9$.

Embodiment 20 relates to a compound of Embodiment 19, wherein the heterocyclyl group is a pyrrolidinyl or an azetidinyl group.

Embodiment 21 relates to a compound of Embodiments 19-20 wherein the heterocyclyl group is substituted with alkyl.

Embodiment 22 relates to a compound of Embodiment 19, wherein the alkylene is a $C_1$-$C_5$ alkylene.

Embodiment 23 relates to a compound of Embodiments 19 or 22, wherein $R^9$ is —OC(O)N($R^{10}$)$_2$ or —(CH$_2$)$_{0-2}$N($R^{10}$)C(O)O$R^{10}$, wherein $R^{10}$ is hydrogen, alkyl, acyl, cycloalkyl, aryl, aralkyl, heterocyclyl, heteroaryl or heteroarylalkyl.

Embodiment 24 relates to a compound of Embodiment 19, wherein the aryl group is substituted with a heterocyclyl group.

Embodiment 25 relates to a compound of Embodiment 1, wherein $R^3$ is aryl substituted with an alkenyl group, a cycloalkyl group or a heterocyclyl group.

Embodiment 26 relates to a compound of Embodiment 25, wherein the heterocyclyl group is 4,5-dihydrooxazolyl, oxaxolyl, oxadiazolyl, indolyl or isoindolyl.

Embodiment 27 relates to a compound of Embodiments 25-26, wherein the heterocyclyl group is substituted with one or more groups selected from the group consisting of alkyl, —C(O)R, —CF$_3$, -alkylene-NR$_2$, —NR$_2$, and —OR, wherein R is defined herein.

Embodiment 28 relates to a compound of Embodiment 25, wherein the cycloalkyl group is cyclopropyl, cyclobutyl or cyclopentyl.

Embodiment 29 relates to a compound of Embodiment 28, wherein the cycloalkyl group is substituted with one or more groups selected from the group consisting of —CN, —OR, -alkylene-NR$_2$, —NR$_2$, and —C(O)N(R)$_2$, wherein R is defined herein.

Embodiment 30 relates to a compound of Embodiment 25, wherein the alkenyl group is substituted with one or more groups selected from the group consisting of alkyl, -alkyl-NR$_2$, and C(O)N(R)$_2$.

Embodiment 31 relates to a compound of Embodiment 1, wherein $R^{11}$ is —N($R^{12}$)C(O)CH($R^{12}$)N($R^{12}$)C(O)$R^{13}$, —N($R^{12}$)SO$_2$$R^3$ or —N($R^{12}$)C(O)$R^3$, wherein $R^3$, $R^{12}$, and $R^{13}$ are defined herein.

Embodiment 32 relates to a compound of Embodiment 31, wherein each $R^{12}$ is hydrogen.

Embodiment 33 relates to a compound of Embodiments 31-32, wherein $R^{13}$ is O$R^{12}$, wherein $R^{12}$ is alkyl or heterocyclyl.

Embodiment 34 relates to a compound of Embodiment 31, wherein $R^{12}$ is hydrogen or alkyl.

Embodiment 35 relates to a compound of Embodiment 31, wherein $R^{11}$ is —C(O)N($R^{12}$)$_2$, wherein each $R^{12}$ is, independently, hydrogen, alkyl, aryl, heterocyclyl or the two $R^{12}$ groups, together with the nitrogen atom to which they are attached, form a heterocyclyl group.

Embodiment 36 relates to the compound of Embodiments 1-35, wherein the compound has an HIV-1 protease inhibition constant (K) of from about 1 fM to about 200 nM.

Embodiment 37 relates to the compound of Embodiments 1-35, wherein the compound has an antiviral activity in vitro against a wild-type laboratory strain, HIV-1$_{LAI}$ with half-maximal inhibitory concentration (IC$_{50}$) of from about 1 fM to about 200 nM.

Embodiment 38 relates to a pharmaceutical composition comprising a compound of Embodiments 1-35 and one or more pharmaceutically acceptable excipients.

Embodiment 39 relates to a method for treating an HIV infection comprising administering a therapeutically effective amount of one or more compounds of Embodiments 1-35, or a pharmaceutical composition of Embodiment 37 comprising a therapeutically effective amount of one or more compounds of Embodiments 1-35, to a patient in need thereof.

Embodiment 40 relates to a compound of Embodiments 1-35 for use as a medicament for treating a patient in need of relief from an HIV infection.

What is claimed is:

1. A compound of the formula (I):

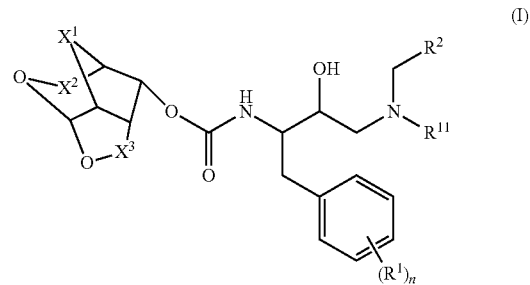

or a pharmaceutically acceptable salt, polymorph, prodrug, solvate or clathrate thereof, wherein:

$X^1$ is alkylene, —O—, —CH$_2$N$R^4$— or —NH$R^4$—;

$X^2$ and $X^3$ are each, independently alkylene;

n is an integer from 0 to 3;

$R^1$ is alkoxy, hydroxyalkyl, halo or heterocyclylalkyloxy;

$R^2$ is alkyl, haloalkyl, aryl, arylalkyl, cycloalkylalkyl, heterocyclylcarbonyl, heterocyclyl, heterocyclylalkyl or —C($R^7R^8$)-alkylene-$R^9$;

$R^{11}$ is —SO$_2$$R^3$, —N($R^{12}$)SO$_2$$R^3$, —N($R^{12}$)C(O)$R^3$, —N($R^{12}$)C(O)CH($R^{12}$)N($R^{12}$)C(O)$R^{13}$, —C(O)N($R^{12}$)$_2$, —C(O)-alkylene-$X^4$—$R^{10}$ (wherein $X^4$ is S, O or N$R^6$, wherein $R^6$ is H, alklyl, cycloalkyl or alkylaryl) or —C(O)$R^{10}$;

$R^3$ is aryl or heteroaryl;

$R^4$ is alkyl, aryl or heteroaryl;

$R^7$ and $R^8$ are each, independently hydrogen, alkyl, aryl, arylalky, heteroaryl, heteroarylalkyl or, $R^7$ and $R^8$, together with the carbon atom to which they are attached, form a cycloalkyl or a heterocyclyl group;

$R^9$ is hydrogen, O$R^{10}$, OC(O)N($R^{10}$)$_2$, CN, NO$_2$, CF$_3$, OCF$_3$, N($R^{10}$)$_2$, S$R^{10}$, SO$R^{10}$, SO$_2$$R^{10}$, SO$_2$N($R^{10}$)$_2$, SO$_3$R, C(O)$R^{10}$, C(O)O$R^{10}$, OC(O)$R^{10}$, C(O)N($R^{10}$)$_2$, (CH$_2$)$_{0-2}$N($R^{10}$)C(O)$R^{10}$ or (CH$_2$)$_{0-2}$N($R^{10}$)C(O)O$R^{10}$;

$R^{10}$ is hydrogen, alkyl, acyl, cycloalkyl aryl, aralkyl, heterocyclyl, heteroaryl, or heteroarylalkyl;

$R^{12}$ is hydrogen, alkyl, alkylaryl, heterocyclyl or the two $R^{12}$ groups on an N($R^{12}$)$_2$, together with the nitrogen atom to which they are attached, form a heterocyclyl group; and $R^{13}$ is hydrogen, alkyl, —N($R^{12}$)$_2$ or —O$R^{12}$; or $R^2$ and $R^{11}$, together with the —CH$_2$N— that connects them, form a heterocyclyl or substituted heterocyclyl group.

2. The compound of claim 1 having the formula (II):

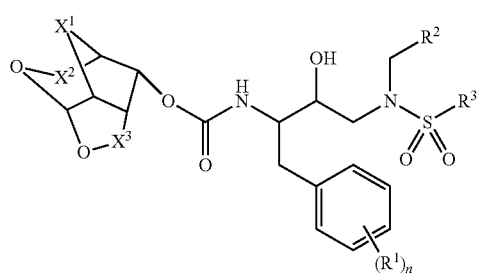
(II)

or a pharmaceutically acceptable salt, polymorph, prodrug, solvate or clathrate thereof, wherein:

n is an integer from 1 to 3;
$R^1$ is alkoxy, hydroxyalkyl, halo or heterocyclylalkyloxy;
$R^2$ is alkyl, haloalkyl, arylalkyl, cycloalkylalkyl, heterocyclylcarbonyl or heterocyclylalkyl:
$R^3$ is substituted aryl or substituted heteroaryl;
$X^1$ is alkylene, —O—, —CH$_2$NR$^4$— or —NHR$^4$—, wherein $R^4$ is alkyl, aryl or heteroaryl; and
$X^2$ and $X^3$ are each, independently alkylene.

3. The compound of claim 1, wherein $X^1$, $X^2$ or $X^3$ is $C_1$-$C_4$ alkylene.

4. The compound of claim 1, wherein $R^1$ is $C_1$-$C_6$ alkoxy, hydroxy-$C_1$-$C_6$-alkyl, halo or $C_3$-$C_6$-heterocyclyl-$C_1$-$C_6$-alkyloxy.

5. The compound of claim 1, wherein $R^2$ is $C_1$-$C_6$ alkyl, halo-$C_1$-$C_6$-alkyl, $C_6$-$C_{10}$-aryl-$C_1$-$C_6$-alkyl, $C_3$-$C_6$-cycloalkyl-$C_1$-$C_6$-alkyl, $C_3$-$C_6$-heterocyclylcarbonyl or $C_3$-$C_6$-heterocyclyl-$C_1$-$C_6$-alkyl.

6. The compound of claim 1, wherein $R^3$ is substituted $C_6$-$C_{10}$ aryl or substituted $C_6$-$C_8$ heteroaryl.

7. The compound of claim 2, wherein the compound of the formula (II) is a compound of the formula (IIa) or (IIb):

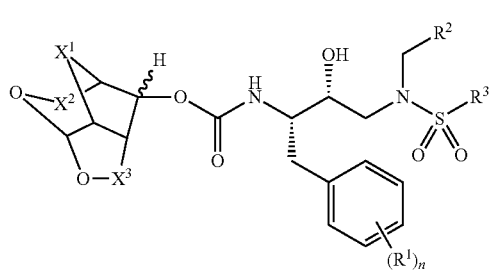
Ia

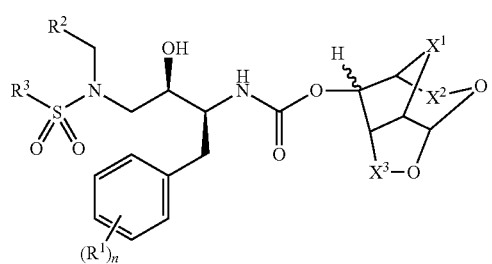
Ib or a pharmaceutically acceptable salt, polymorph, prodrug, solvate or clathrate thereof.

8. The compound of claim 1 which is:

A
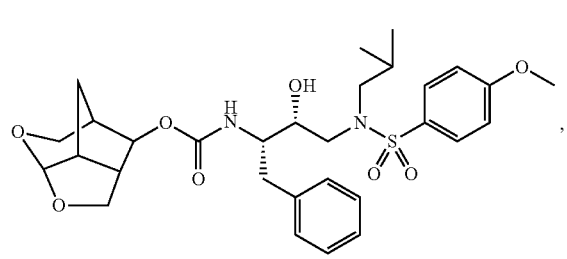
,

B
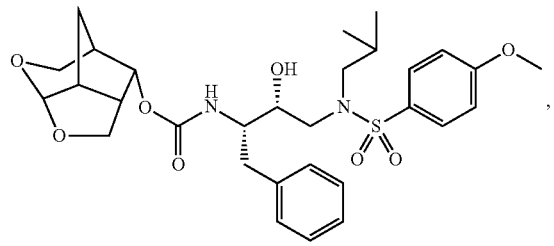
,

C
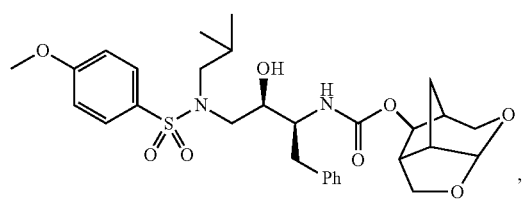
,

D
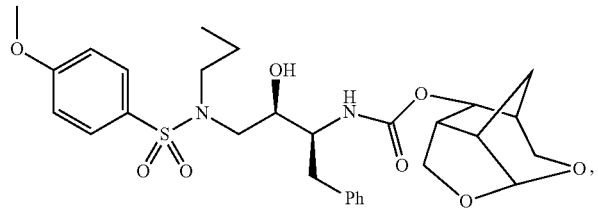
,

E
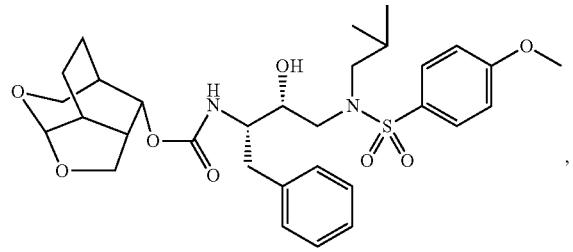
,

F
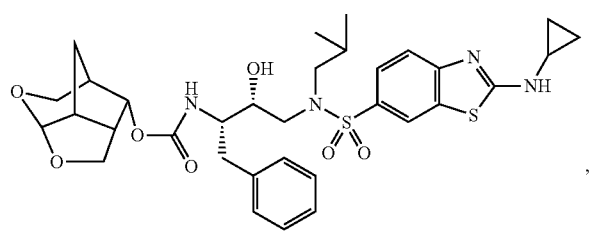
,

-continued
G
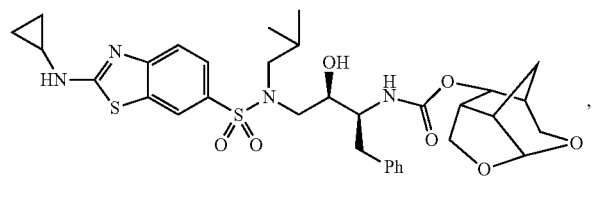,
H
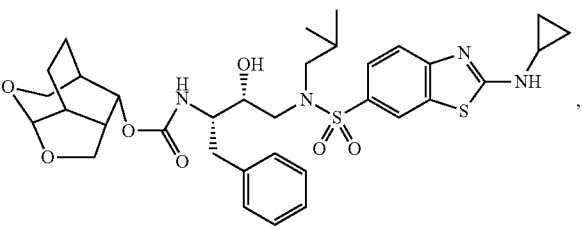,
I
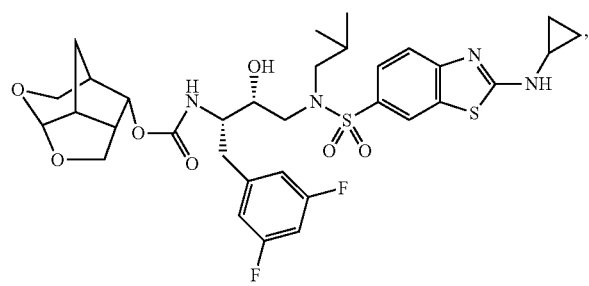,
J
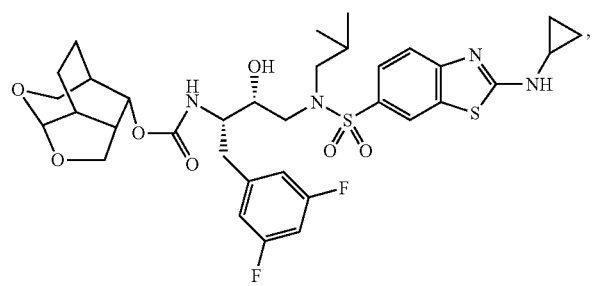,
K
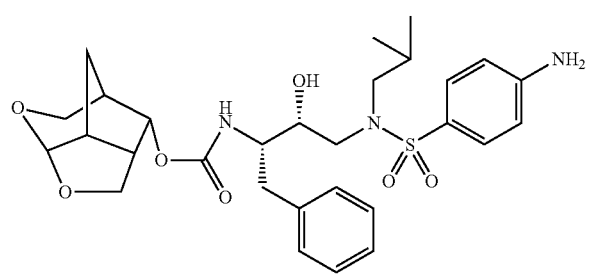,
L
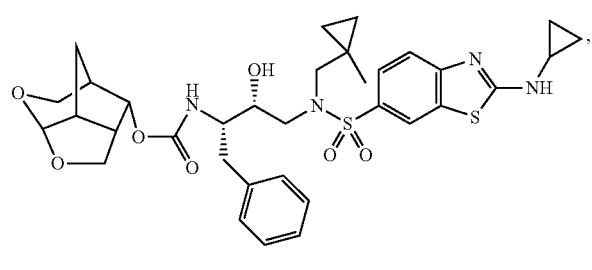,
M
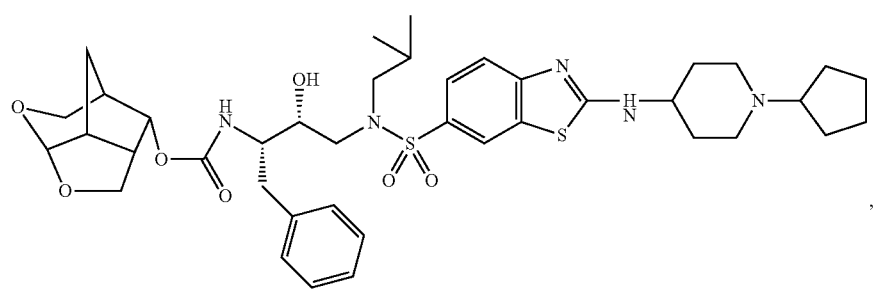,
N
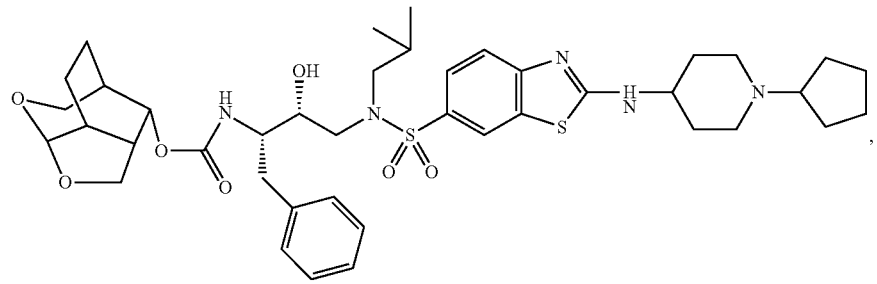,

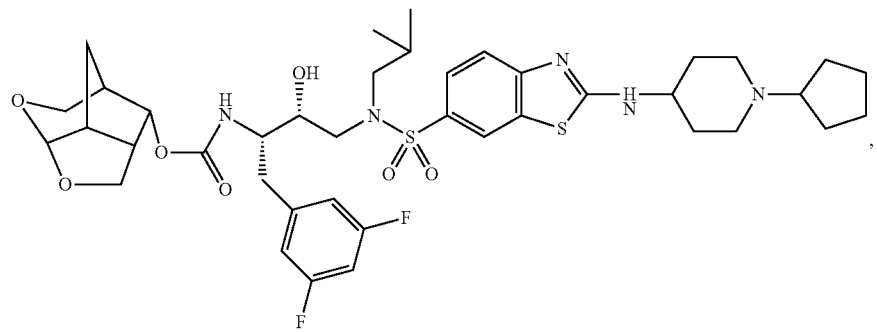
O
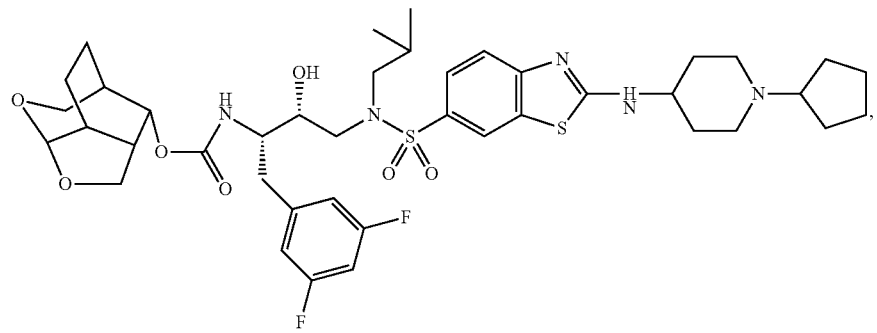
P
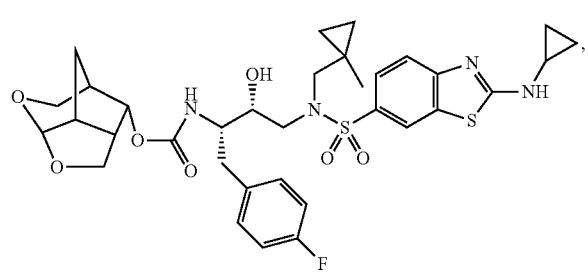
Q
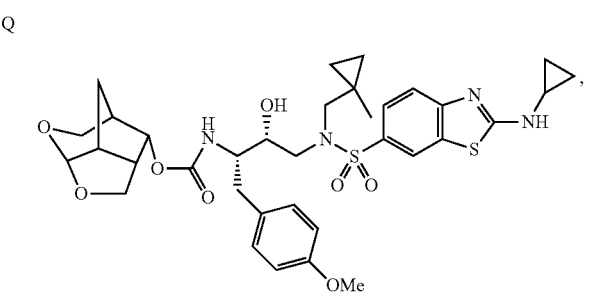
R
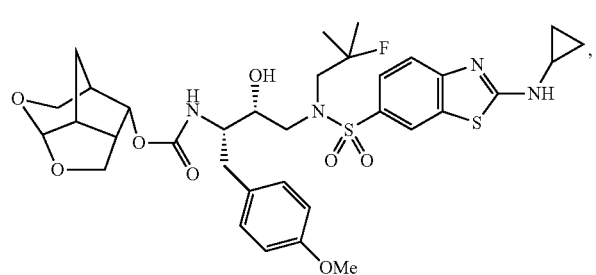
S
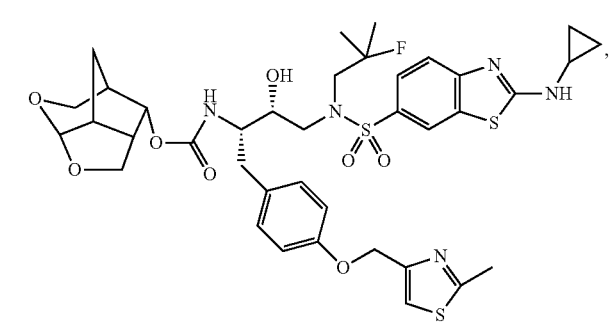
T
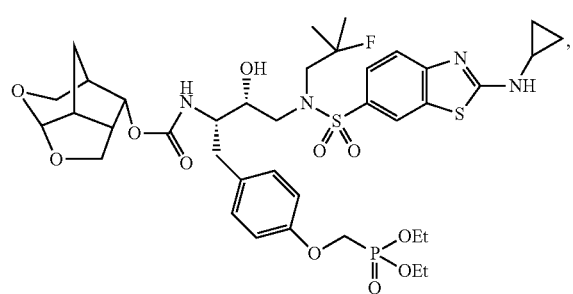
U
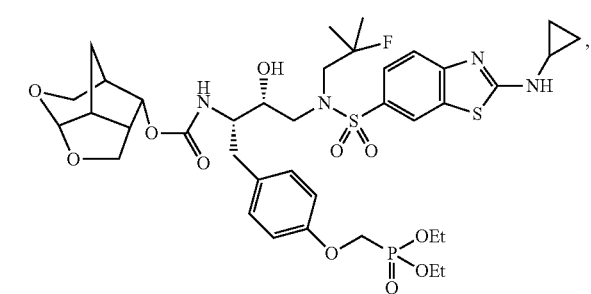
V -continued
W
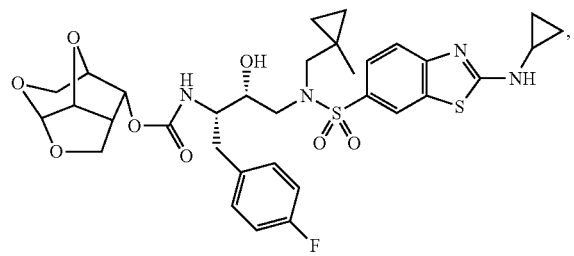
X
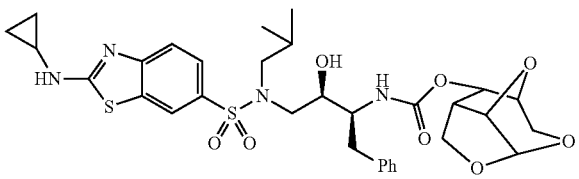
Y
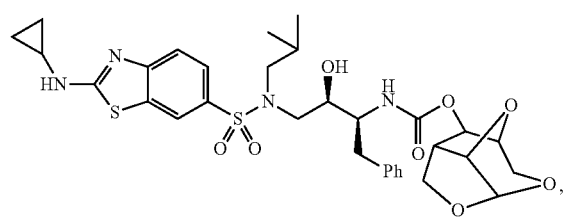
Z
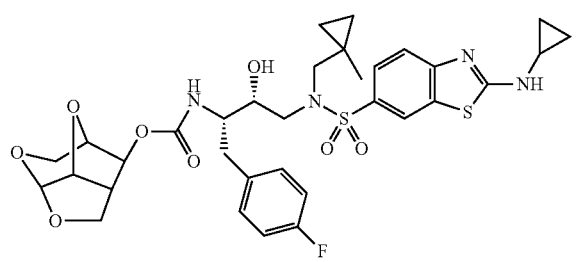
A-1
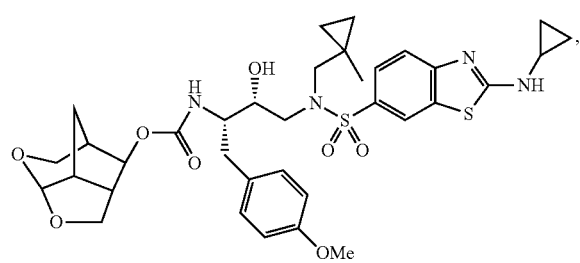
B-1
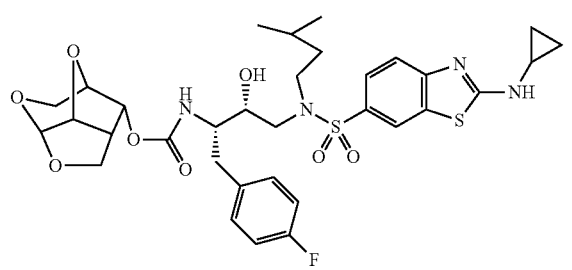
C-1
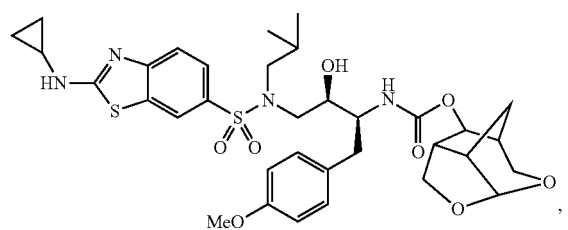
D-1
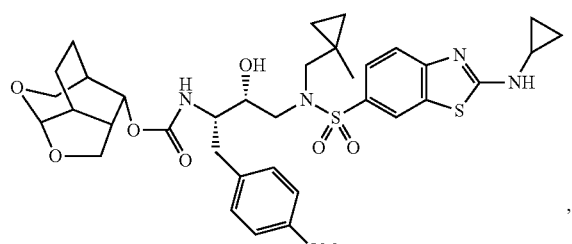
E-1
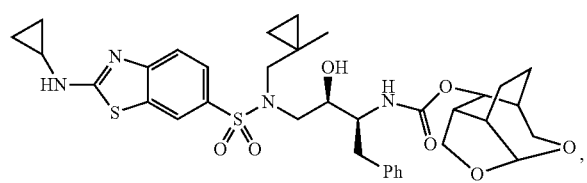
F-1
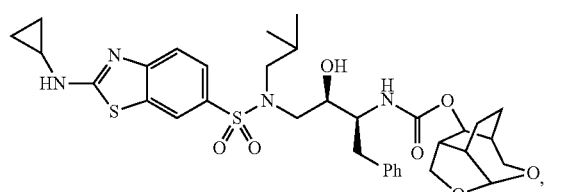
G-1
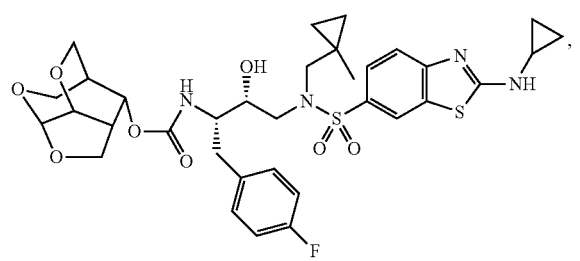
H-1
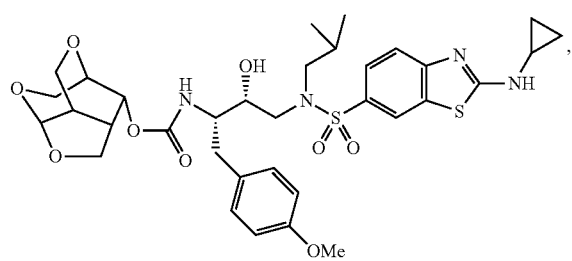

-continued
I-1
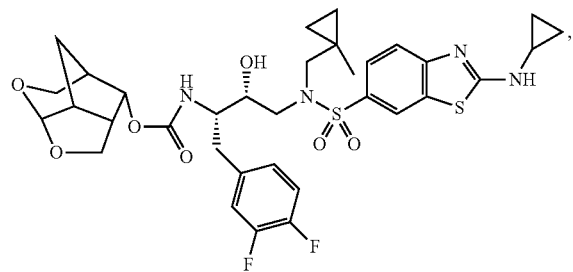
J-1
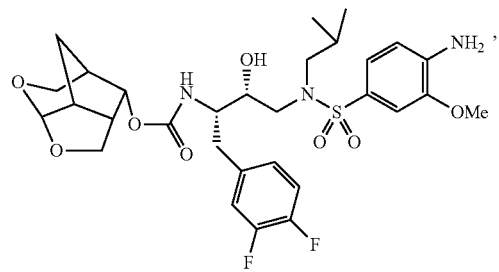
K-1
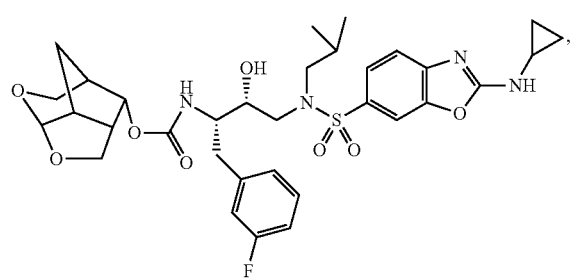
L-1
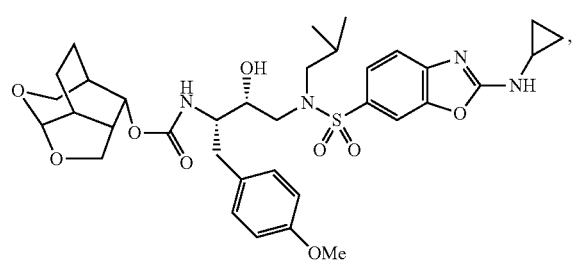
M-1
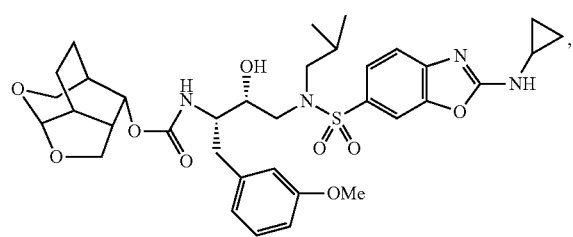
N-1
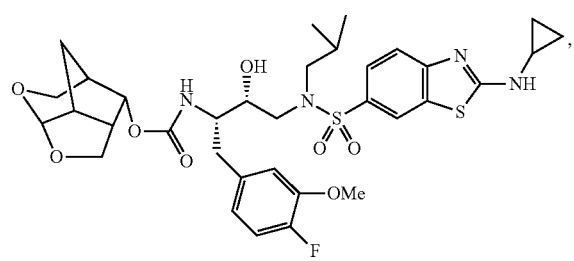
O-1
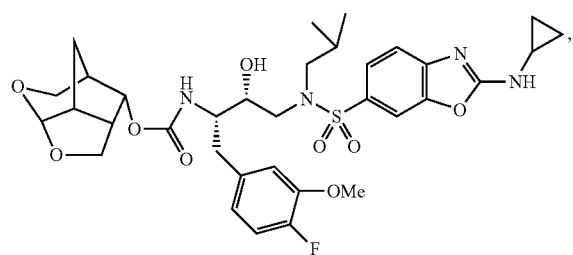
or a pharmaceutically acceptable salt, polymorph, prodrug, solvate or clathrate thereof.

9. The compound of claim 1 which is:
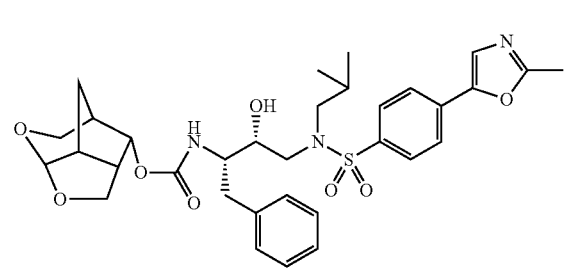
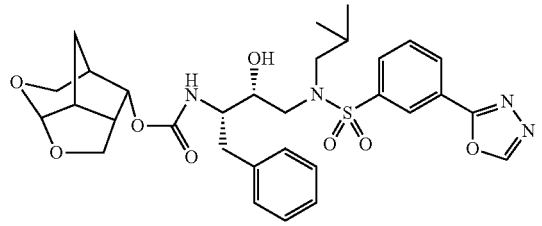
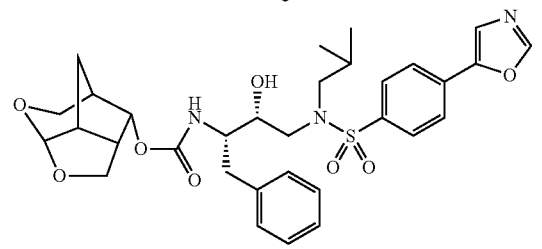
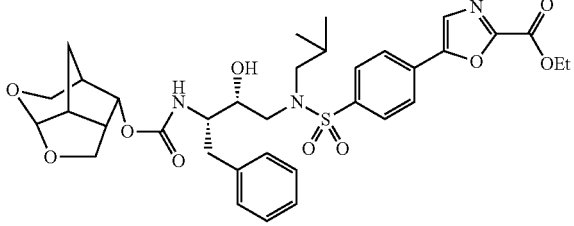
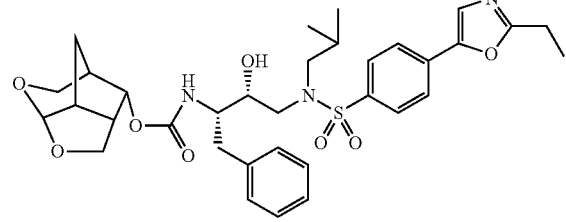
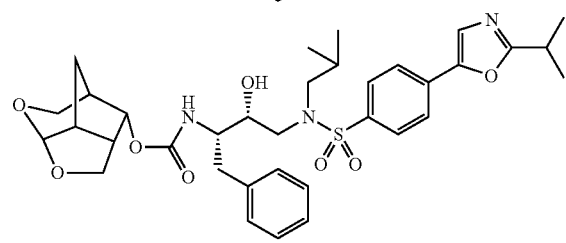
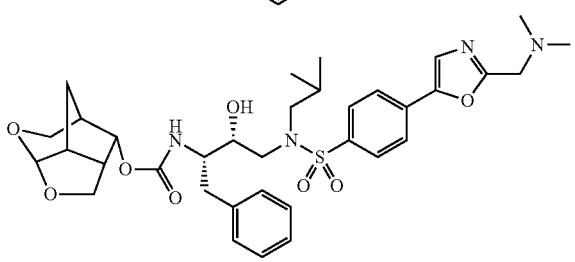
-continued
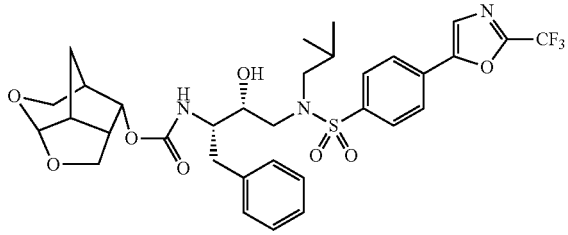
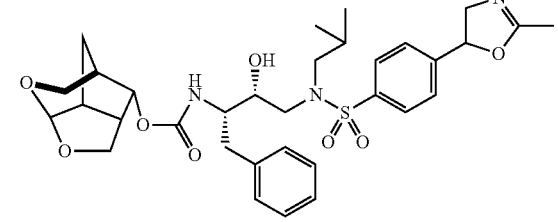
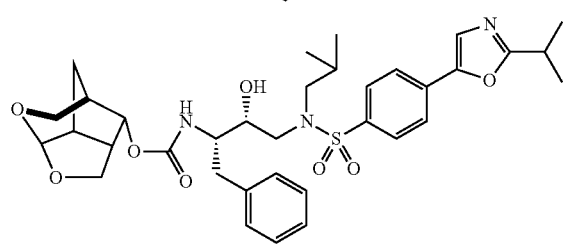
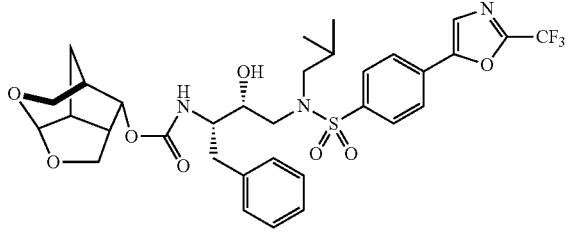
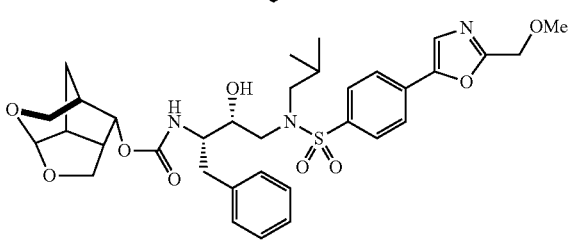
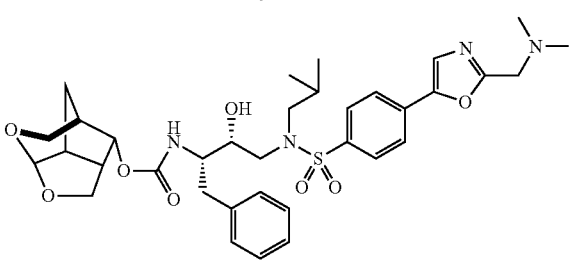
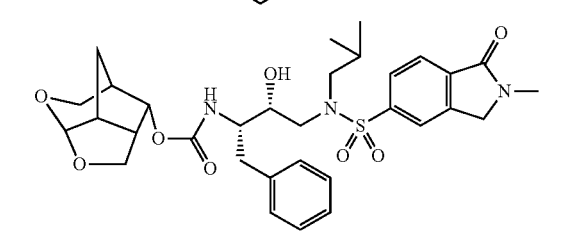

111
-continued
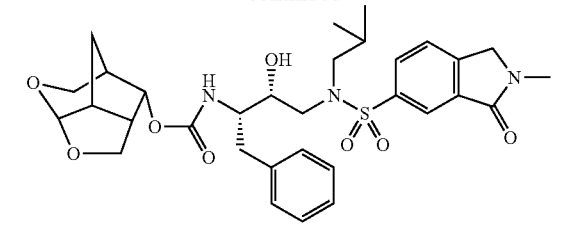
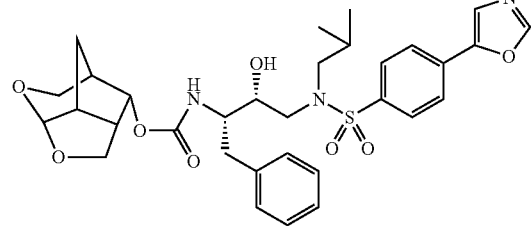
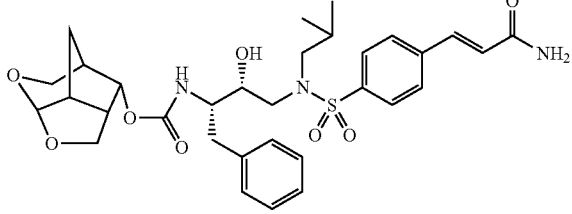
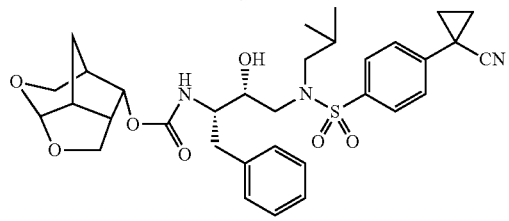
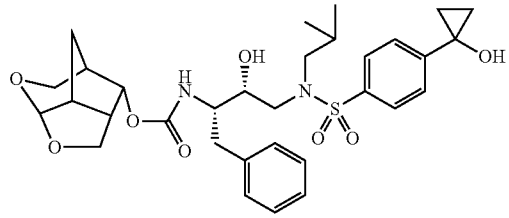
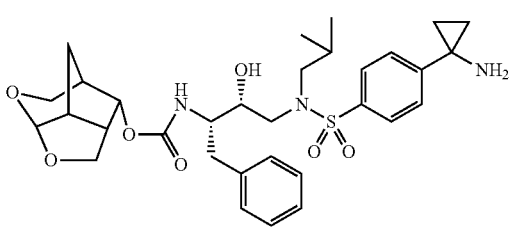
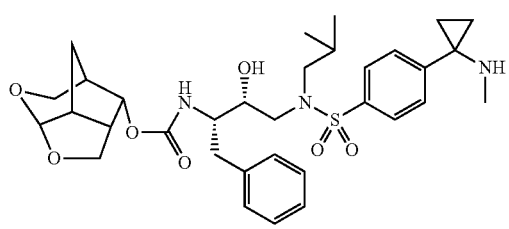
112
-continued
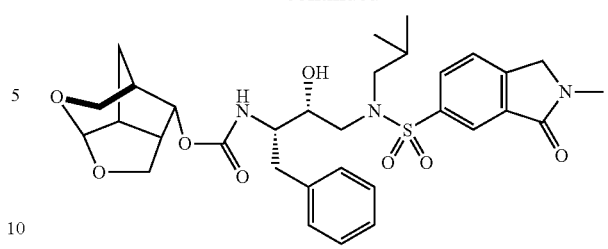
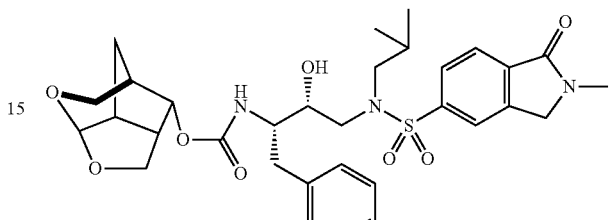
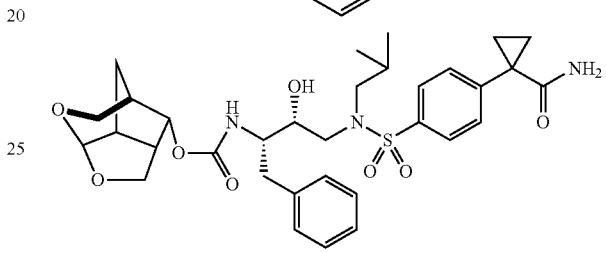
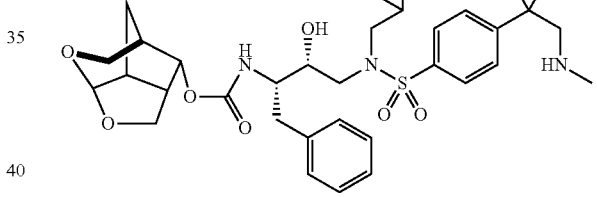
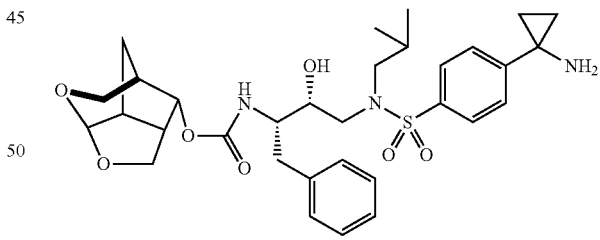
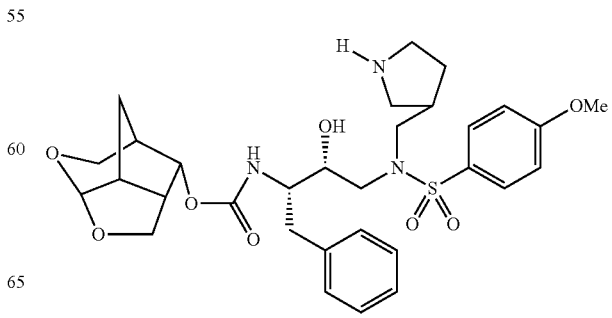

113
-continued
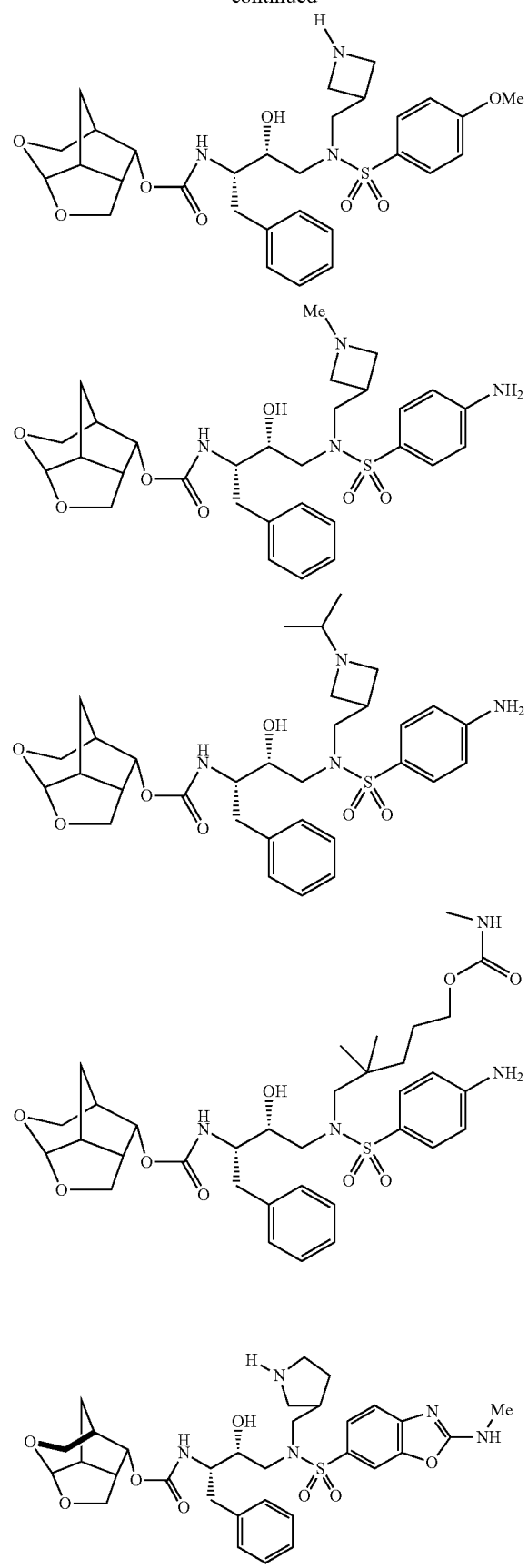
114
-continued
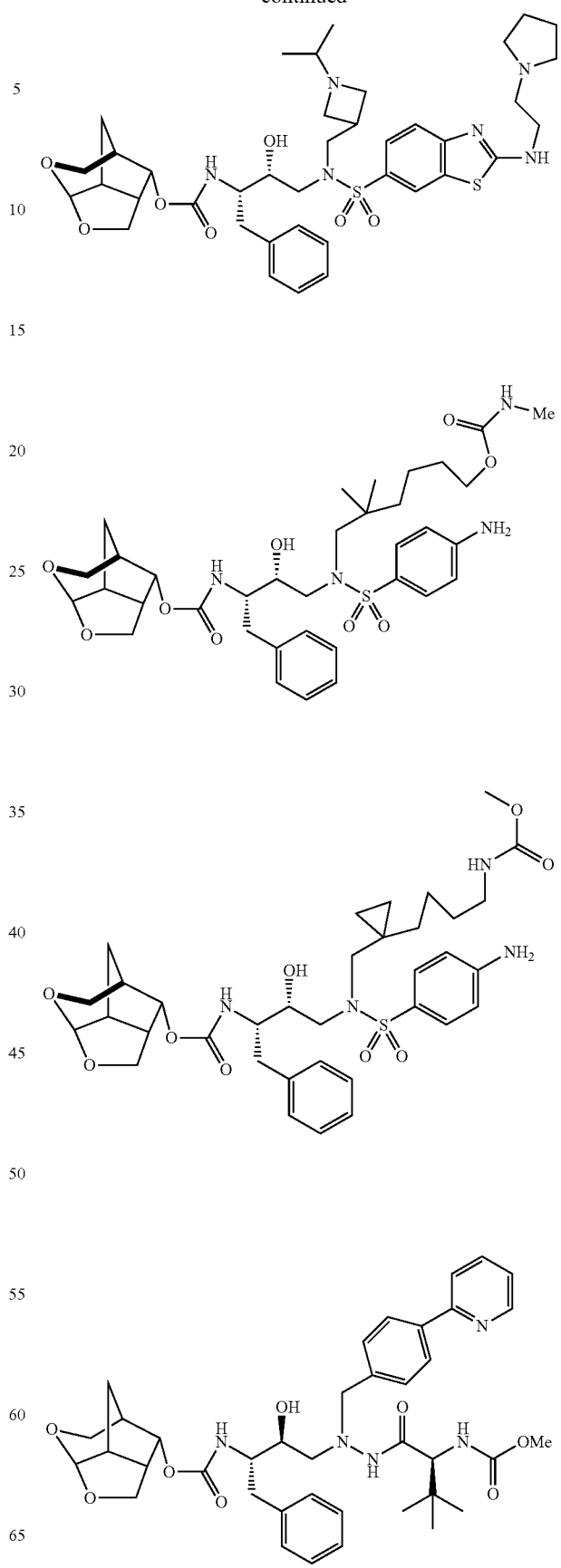

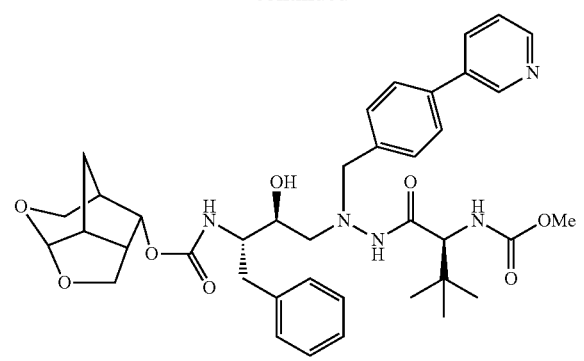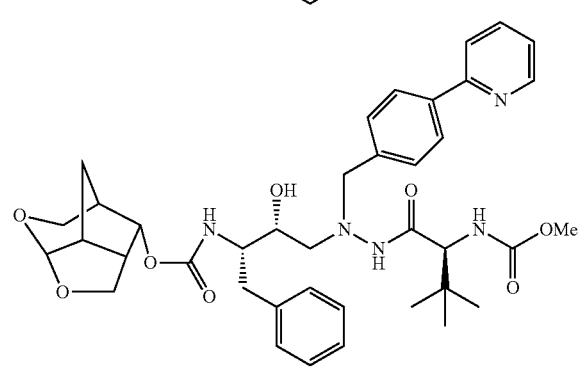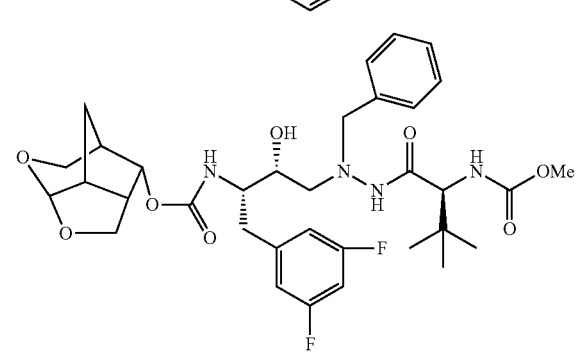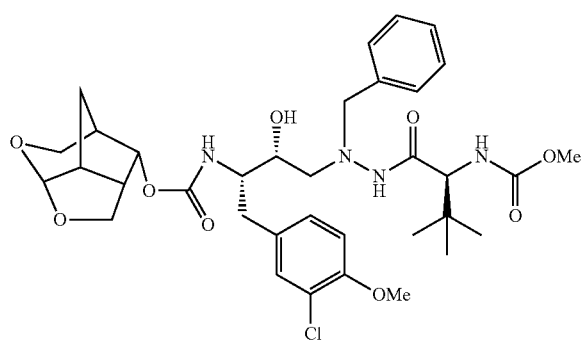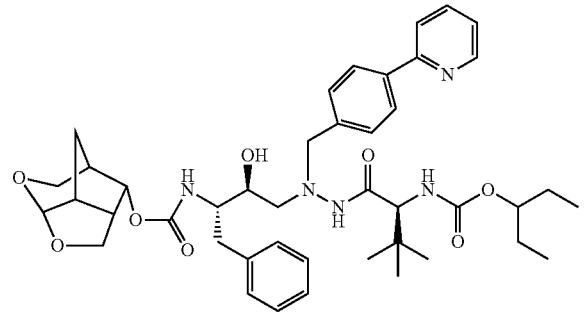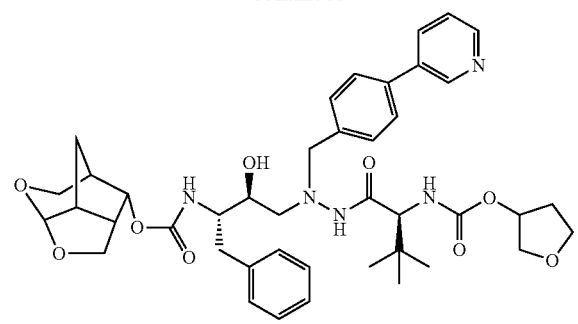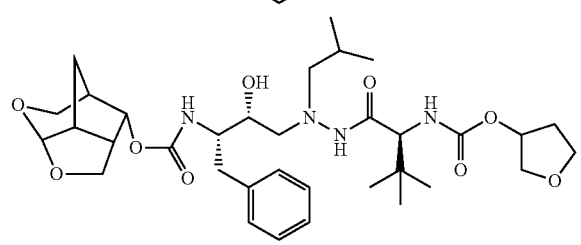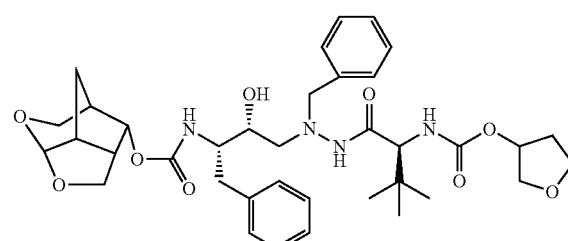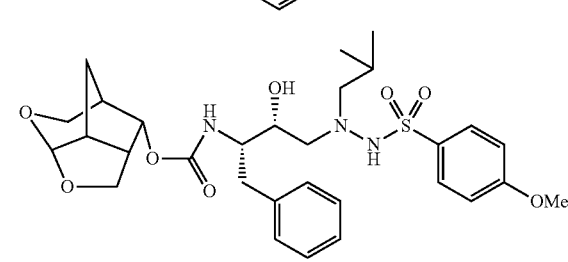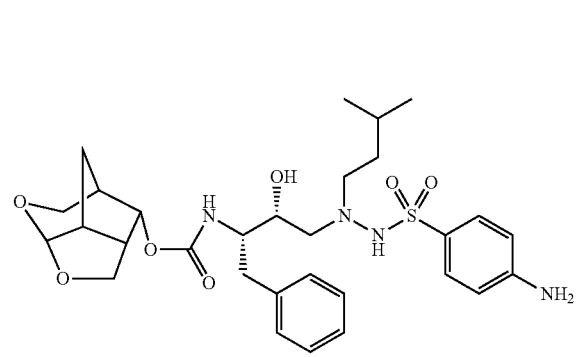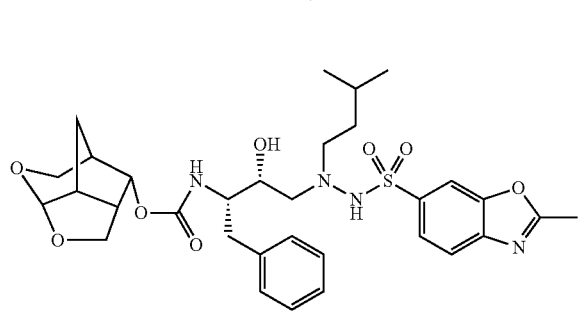

117
-continued
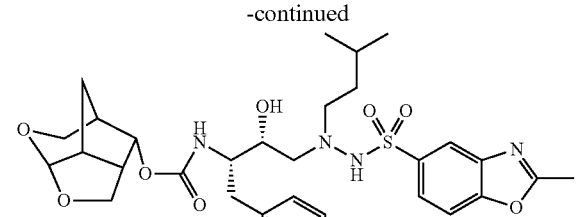
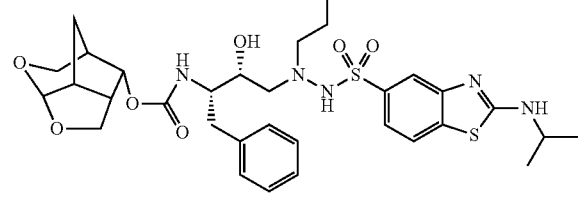
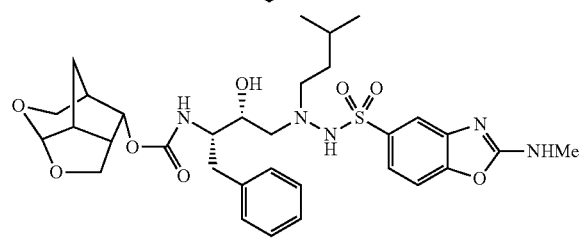
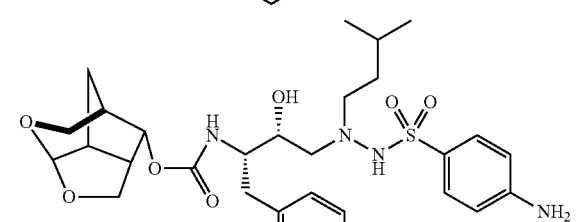
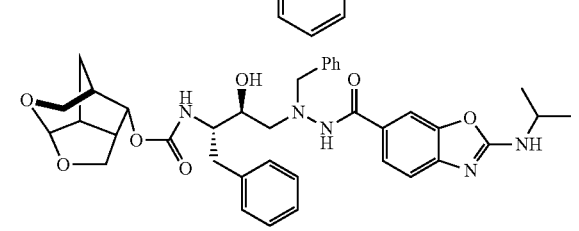
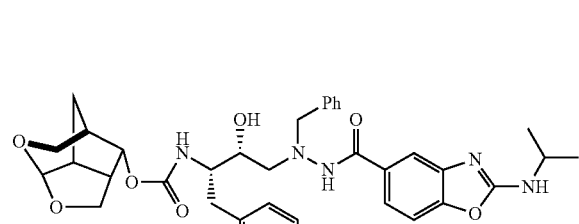
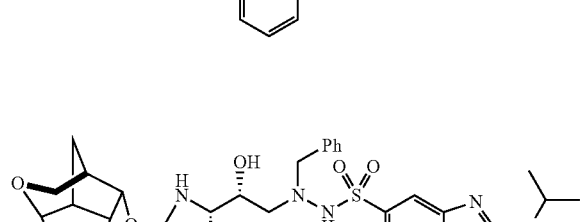
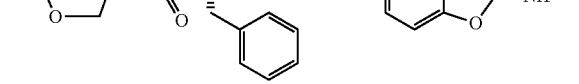
118
-continued
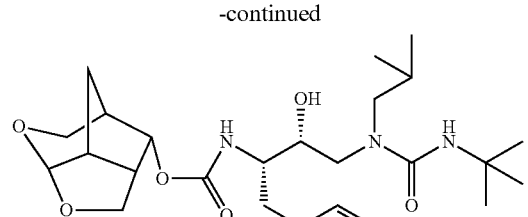
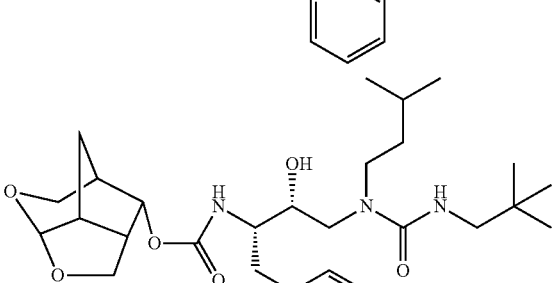
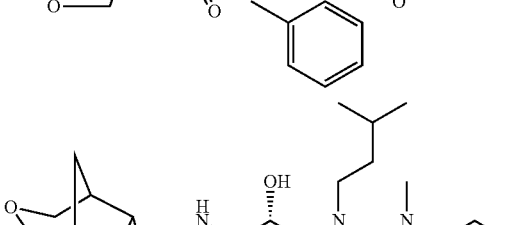
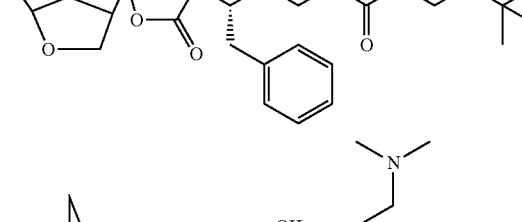
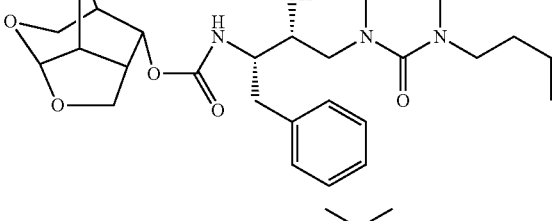
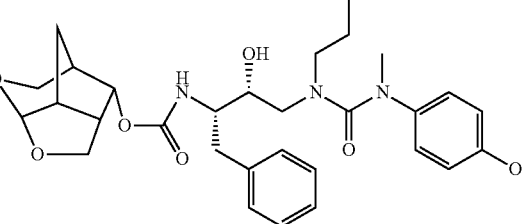
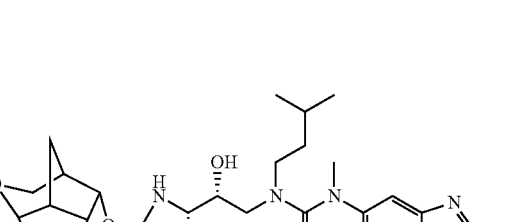
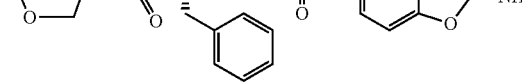

-continued

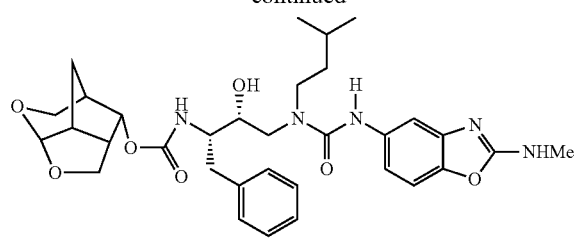

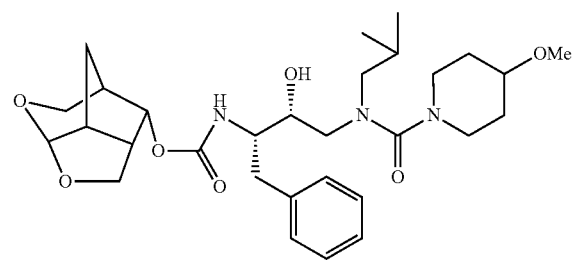

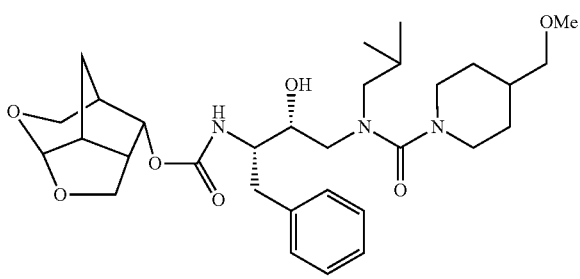

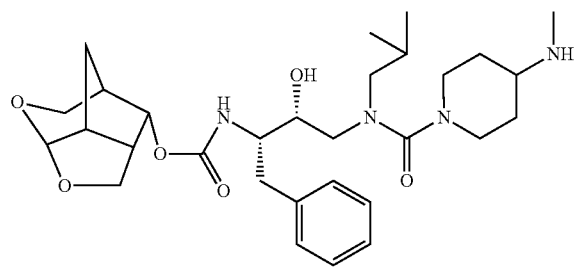

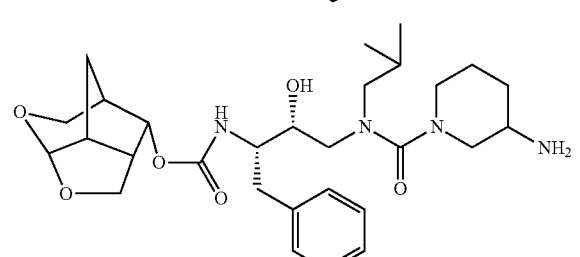

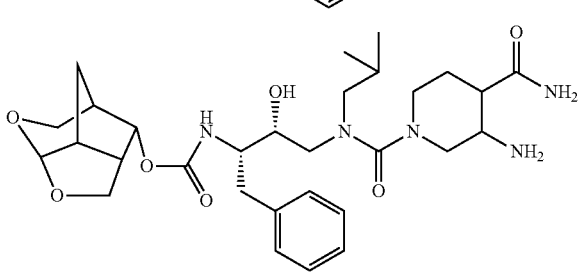

-continued

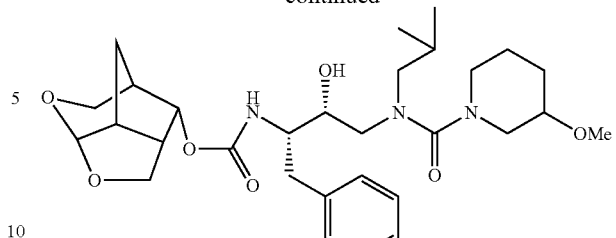

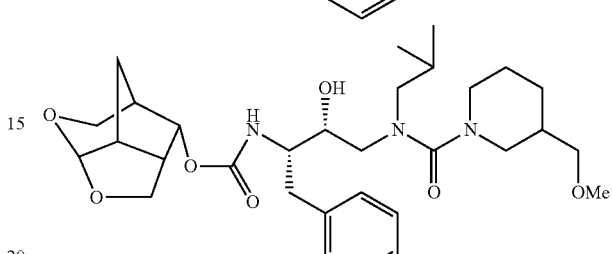

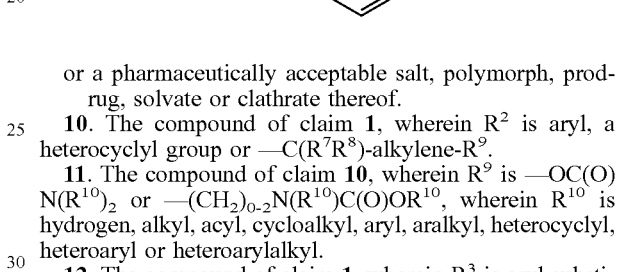

or a pharmaceutically acceptable salt, polymorph, prodrug, solvate or clathrate thereof.

10. The compound of claim 1, wherein $R^2$ is aryl, a heterocyclyl group or —C($R^7R^8$)-alkylene-$R^9$.

11. The compound of claim 10, wherein $R^9$ is —OC(O)N($R^{10}$)$_2$ or —(CH$_2$)$_{0-2}$N($R^{10}$)C(O)O$R^{10}$, wherein $R^{10}$ is hydrogen, alkyl, acyl, cycloalkyl, aryl, aralkyl, heterocyclyl, heteroaryl or heteroarylalkyl.

12. The compound of claim 1, wherein $R^3$ is aryl substituted with an alkenyl group, a cycloalkyl group or a heterocyclyl group.

13. The compound of claim 12, wherein the heterocyclyl group is 4,5-dihydrooxazolyl, oxaxolyl, oxadiazolyl, indolyl or isoindolyl.

14. The compound of claim 12, wherein the alkenyl group is substituted with one or more groups selected from the group consisting of alkyl, -alkyl-NR$_2$, and C(O)N(R)$_2$, wherein R is hydrogen, alkyl, acyl, cycloalkyl, aryl, aralkyl, heterocyclyl, heteroaryl or heteroarylalkyl.

15. The compound of claim 1, wherein $R^{11}$ is —N($R^{12}$)C(O)CH($R^{12}$)N($R^{12}$)C(O)$R^{13}$, —N($R^{12}$)SO$_2R^3$ or —N($R^2$)C(O)$R^3$.

16. The compound of claim 1, wherein $R^{11}$ is —C(O)N($R^{12}$)$_2$, wherein each $R^{12}$ is, independently, hydrogen, alkyl, aryl, heterocyclyl or the two $R^{12}$ groups, together with the nitrogen atom to which they are attached, form a heterocyclyl group.

17. The compound of claim 1, wherein the compound has an HIV-1 protease inhibition constant ($K_i$) of from about 1 fM to about 200 nM.

18. The compound of claim 1, wherein the compound has an antiviral activity in vitro against a wild-type laboratory strain, HIV-1$_{LAI}$ with half-maximal inhibitory concentration (IC$_{50}$) of from about 1 fM to about 200 nM.

19. A pharmaceutical composition comprising a compound of claim 1 and one or more pharmaceutically acceptable excipients.

20. A method for treating an HIV infection comprising administering a therapeutically effective amount of one or more compounds as in of claim 1 to a patient in need thereof.

* * * * *